United States Patent
Hodges et al.

(10) Patent No.: US 10,874,745 B2
(45) Date of Patent: Dec. 29, 2020

(54) ANTIMICROBIAL PEPTIDES AND METHODS OF TREATING GRAM-NEGATIVE PATHOGENS: POLAR AND NON-POLAR FACE ANALOGS

(71) Applicant: THE REGENTS OF THE UNIVERSITY OF COLORADO, A BODY CORPORATE, Denver, CO (US)

(72) Inventors: Robert S. Hodges, Aurora, CO (US); Ziqing Jiang, Denver, CO (US); Lajos Gera, Denver, CO (US); Colin T. Mant, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 16/606,454

(22) PCT Filed: Apr. 19, 2018

(86) PCT No.: PCT/US2018/028398
§ 371 (c)(1),
(2) Date: Oct. 18, 2019

(87) PCT Pub. No.: WO2018/195329
PCT Pub. Date: Oct. 25, 2018

(65) Prior Publication Data
US 2020/0129634 A1  Apr. 30, 2020

Related U.S. Application Data

(60) Provisional application No. 62/487,361, filed on Apr. 19, 2017.

(51) Int. Cl.
| | |
|---|---|
| A61K 47/68 | (2017.01) |
| A61K 47/62 | (2017.01) |
| A61P 31/04 | (2006.01) |
| C07K 14/46 | (2006.01) |
| A61K 38/00 | (2006.01) |

(52) U.S. Cl.
CPC .......... *A61K 47/6811* (2017.08); *A61K 47/62* (2017.08); *A61P 31/04* (2018.01); *C07K 14/461* (2013.01); *C07K 14/463* (2013.01); *A61K 38/00* (2013.01)

(58) Field of Classification Search
CPC .... A61P 31/04; F02P 7/00; F02P 1/005; F02P 7/10; A61K 38/00; A61K 47/62; A61K 47/6811
See application file for complete search history.

(56) References Cited

U.S. PATENT DOCUMENTS

| | | |
|---|---|---|
| 6,358,921 B1 | 3/2002 | Kondejewski et al. |
| 2010/0099614 A1 | 4/2010 | Hodges et al. |
| 2011/0028386 A1 | 2/2011 | Hodges et al. |
| 2013/0035469 A1 | 2/2013 | Hodges et al. |
| 2016/0333062 A1 | 11/2016 | Jiang et al. |

FOREIGN PATENT DOCUMENTS

| | | |
|---|---|---|
| WO | WO 2010/141760 | 12/2010 |
| WO | WO 2015/112980 | 7/2015 |
| WO | WO 2018/175410 | 9/2018 |
| WO | WO 2018/217880 | 11/2018 |

OTHER PUBLICATIONS

International Search Report and Written Opinion prepared by the ISA/US dated Aug. 8, 2018, for International Application No. PCT/US2018/028398.
Mant et al., "Design of Novel Amphipathic α-Helical Antimicrobial Peptides with No Toxicity as Therapeutics against the Antibiotic-Resistant Gram-Negative Bacterial Pathogen, *Acinetobacter baumannii*" Journal of Medicinal Chemistry and Drug Design, May 30, 2019, vol. 2, No. 2, 2019, 10 pages.
Mant et al., "De Novo Designed Amphipathic α-Helical Antimicrobial Peptides Incorporating Dab and Dap Residues on the Polar Face to Treat the Gram-Negative Pathogen, *Acinetobacter baumannii*" Journal of Medicinal Chemistry, vol. 62, 2019, 13 pages.
"No ESKAPE! New Drugs Against MRSA, Other Superbugs Still Lacking," Infectious Diseases Society of America in Science Daily, Dec. 9, 2008, retrieved from https://www.sciencedaily.com/releases/2008/12/081201105706.htm, 2 pages.
Biswas et al., "Colistin: an update of the antibiotic of the 21st century," Expert Review of Anti-infective Therapy, vol. 10, No. 8, 2012, 17 pages.
Bland et al., "All-D-cecropin B: Synthesis, conformation, lipopolysaccharide binding, and antibacterial activity," Molecular and Cellular Biochemistry, vol. 218, 2001, pp. 105-111.
Chen et al., "Comparison of Biophysical and Biologic Properties of α-Helical Enantiomeric Antimicrobial Peptides," Chemical Biology and Drug Design, vol. 67, No. 2, Feb. 14, 2006, pp. 162-173.
Chen et al., "Determination of stereochemistry stability coefficients amino acid side-chains in an amphipathic α-helix," Journal of Peptide Research, vol. 59, No. 1, Jan. 2002, pp. 18-33.

(Continued)

*Primary Examiner* — Soren Harward
*Assistant Examiner* — Jia-Hai Lee
(74) *Attorney, Agent, or Firm* — Sheridan Ross P.C.

(57) ABSTRACT

Antimicrobial agents, including antimicrobial peptides (AMPs), and uses thereof. Compositions and methods of using dermaseptin-type and piscidin-type antimicrobial peptide variants that demonstrate activity and improved therapeutic indices against microbial pathogens. The peptide compositions demonstrate the ability to not only maintain or improve antimicrobial activity against bacterial pathogens including Gram-negative microorganisms *Acinetobacter baumannii* and *Pseudomonas aeruginosa*, but also significantly decrease hemolytic activity against human red blood cells. Specificity determinants within the AMPs change selectivity from broad spectrum antimicrobial activity to Gram-negative selectivity.

11 Claims, 26 Drawing Sheets

Specification includes a Sequence Listing.

(56) References Cited

OTHER PUBLICATIONS

Chen et al., "Rational Design of α-Helical Antimicrobial Peptides with Enhanced Activities and Specificity/Therapeutic Index," Journal of Biological Chemistry, vol. 280, No. 13, Apr. 1, 2005, pp. 12316-12329.

Chen et al., "Role of Peptide Hydrophobicity in the Mechanism of Action of α-Helical Antimicrobial Peptides," Antimicrobial Agents and Chemotherapy, vol. 51, No. 4, Apr. 2007, pp. 1398-1406.

Coast et al., "Superbugs: Should Antimicrobial Resistance be Included as a Cost in Economic Evaluation?," Health Economics, vol. 5, Feb. 1996, pp. 217-226.

Cribbs et al., "All-D-Enantiomers of B-Amyloid Exhibit Similar Biological Properties to All-L-B-Amyloids," Journal of Biological Chemistry, vol. 272, No. 11, Mar. 14, 1997, pp. 7431-7436.

De Lucca et al., "D-Cecropin B: proteolytic restistance, lethality for pathogenic fungi and binding properties," Medical Mycology, vol. 38, Jan. 2000, pp. 301-308.

Eisenberg et al., "The helical hydrophobic moment: a measure of the amphiphilicity of a helix," Nature, vol. 299, Sep. 23, 1982, pp. 371-374.

Elmquist et al., "In vitro Uptake and Stability Study of pVEC and its All-D Analog," Biological Chemistry, vol. 384, No. 3, 2003, pp. 387-393.

Garza-Gonzalez et al., "Prevalence of Multidrug-Resistant Bacteria at a Tertiary-Care Teaching Hospital in Mexico: Special Focus on Acinetobacter baumannii," Chemotherapy, vol. 56, Aug. 9, 2010, pp. 275-279.

Hamamoto et al., "Antimicrobial Activity and Stability to Proteolysis of Small Linear Cationic Peptides with D-Amino Acid Substitutions," Microbiology and Immunology, vol. 46, No. 11, Aug. 2002, pp. 741-749.

Hong et al., "Effect of D-amino acid substitution on the stability, the secondary structure, and the activity of membrane-active peptide," Biochemical Pharmacology, vol. 58, No. 11, Dec. 1999, pp. 1775-1780.

Jenssen et al., "Peptide Antimicrobial Agents," Clinical Microbiology Reviews, vol. 19, No. 3, Jul. 2006, pp. 491-511.

Jiang et al., "'Specificity Determinants' Improve Therapeutic Indices of Two Antimicrobial Peptides Piscidin 1 and Dermaseptin S4 Against the Gram-negative Pathogens Acinetobacter baumannli and Pseudomonas aeruginosa, Pharmaceuticals, vol. 7, 2014, pp. 366-391.

Jiang et al., "Anti-Tuberculosis Activity of α-Helical Antimicrobial Peptides: De Novo Designed L- and D-Enantiomers Versus L- and D-LL37," Protein & Peptide Letters, vol. 18, No. 3, Mar. 2011, pp. 241-252.

Jiang et al., "Effects of net charge and the number of positively charged residues on the biological activity of amphipathic α-helical cationic antimicrobial peptides," Biopolymers (Peptide Science), vol. 90, No. 3, Apr. 2008, pp. 369-383.

Jiang et al., "Rational Design of α-Helical Antimicrobial Peptides to Target Gram-negative Pathogens, Acinetobacter baumannii and Pseudomonas aeruginosa: Utilization of Charge, 'Specificity Determinants', Total Hydrophobicity, Hydrophobe Type and Location as Design Parameters to Improve the Therapeutic Ratio," Chemical Biology & Drug Design, vol. 77, 2011, pp. 225-240.

Jiang et al., "Role of positively charged residues on the polar and non-polar faces of amphipathic α-Helical antimicrobial peptides on specificity and selectivity for Gram-negative pathogens," Chemical Biology & Drug Design, vol. 91, 2018, pp. 75-92.

Jiang et al., Design of New Antimicrobial Peptides (AMPs) with "Specificity Determinants" that Encode Selectivity for Gram-negative Pathogens and Remove both Gram-positive Activity and Hemolytic Activity from Broad-spectrum AMPs, Proceedings of the 24th American Peptide Symposium, American Peptide Society, 2015, pp. 245-248.

Jiang et al., Effects of Hydrophobicity on the Antifungal Activity of α-Helical Antimicrobial Peptides, Chemical Biology and Drug Design, vol. 72, No. 6, Dec. 2008, pp. 483-495.

Kovacs et al., "Determination of Intrinsic Hydrophilicity/ Hydrophobicity of Amino Acid Side Chains in Peptides in the Absence of Nearest-Neighbor or Conformational Effects," Biopolymers (Peptide Science), vol. 84, 2006, pp. 283-297.

Lee et al., "A Novel Method to Measure Self-association of Small Amphipathic Molecules," Journal of Biological Chemistry, vol. 278, No. 25, Jun. 20, 2003, pp. 22918-22927.

Mant et al., "Review: Intrinsic Amino Acid Side-Chain Hydrophilicity/ Hydrophobicity Intrinsic Amino Acid Side-Chain Hydrophilicity/ Hydrophobicity Coefficients Chromatography of Model Peptides: Comparison With Other of Model Peptides: Comparison With Other Hydrophilicity/Hydrophobicity Scales," Biopolymers (Peptide Science), vol. 92, No. 6, Sep. 2009, pp. 573-595.

Pouny et al., "Interaction of antimicrobial dermaseptin and its fluorescently labeled analogs with phospholipid membranes," Biochemistry, vol. 31, No. 49, 1992, pp. 12416-12423.

Wade et al., "All-D amino acid-containing channel-forming antibiotic peptides," Proceedings of the National Academy of Sciences of the United States of America, vol. 87, Jun. 1990, pp. 4761-4765.

Wakabayashi et al., "N-Acylated and D Enantiomer Derivatives of a Nonamer Core Peptide of Lactoferricin B Showing Improved Antimicrobial Activity," Antimicrobial Agents and Chemotherapy, vol. 43, No. 5, May 1999, pp. 1267-1269.

Yu et al., "Antibacterial Mechanisms of Polymyxin and Bacterial Resistance," BioMed Research International, vol. 2015, No. 679109, Jan. 15, 2015, 11 pages.

Zhou et al., "Effect of preferred binding domains on peptide retention behavior in reversed-phase chromatography: amphipathic alpha-helices," Peptide Research, vol. 3, No. 1, Dec. 31, 1989, pp. 8-20, Abstract only.

Official Action for Australian Patent Application No. 2018256427, dated Apr. 24, 2020, 7 pages.

International Preliminary Report on Patentability for International (PCT) Application No. PCT/US2018/028398, dated Oct. 31, 2019, 8 pages.

D41 X13/X16
(D33 S4K/X13/X16)

Hydrophobic Face of the Amphipathic α-Helix

Stationary Phase (bound state) | Mobile Phase (unbound state)

A) Low temperature

B) Higher temperature when maximum retention time reached

C) High temperature beyond maximum retention time

ANTIMICROBIAL PEPTIDES AND METHODS OF TREATING GRAM-NEGATIVE PATHOGENS: POLAR AND NON-POLAR FACE ANALOGS

CROSS-REFERENCE TO RELATED APPLICATIONS

This application is a national stage application under 35 U.S.C. § 371 and claims the benefit of PCT Application No. PCT/US2018/028398 having an international filing date of Apr. 19, 2018, which designated the United States, which PCT application claims the benefit of priority under 35 U.S.C. § 119(e) to U.S. Provisional Patent Application Ser. No. 62/487,361, filed Apr. 19, 2017, The entire disclosures of PCT Application No. PCT/US2018/019860 and U.S. Provisional Patent Application No. 62/487,361 are incorporated herein by reference.

REFERENCE TO A SEQUENCE LISTING

This application contains a Sequence Listing submitted electronically as a text file by EFS-Web. The text file, named "01-2848-239-PCT Sequence ListingST25.txt", has a size in bytes of 19000 bytes, and was recorded on Apr. 19, 2018. The information contained in the text file is incorporated herein by reference in its entirety pursuant to 37 CFR § 1.52(e)(5).

FIELD OF THE INVENTION

This disclosure relates to the field of antimicrobial peptides (AMPS) and treatments for microbial infections.

BACKGROUND

The explosion of bacterial resistance to traditional antibiotics and a rapid increase in the incidence of multi-drug resistant microbes have created an urgency to develop new classes of antimicrobial agents. There are now "Superbugs" resistant to most or all antibiotics (Coast, J., et al., Health Economics 1996, 5:217-26). The Infectious Diseases Society of America has reported that two-thirds of all health care associated infections are caused by six multi-drug resistant organisms referred to as "ESKAPE" pathogens consisting of two Gram-positive organisms, *Enterococcus faecium* and *Staphylococcus aureus*, and four Gram-negative organisms, *Klebsiella pneumonia, Acinetobacter baumannii, Pseudomonas aeruginosa* and *Enterbacter* species (sciencedaily.com/releases/2008/12/081201105706.htm). A recent study in Mexico demonstrated dramatic increases in the incidence of antibiotic-resistant species (Garza-Gonzalez, E., et al., Chemotherapy 2010, 56:275-79). Of 550 clinical isolates of *A. baumannii* and 250 clinical isolates of *P. aeruginosa*, 74% of *A. baumannii*, and 34% of *P. aeruginosa* were multi-drug resistant.

Polymyxin B and Polymyxin E (Colistin) are cationic peptides consisting of a cyclic heptapeptide with a tripeptide side chain acylated by a fatty acid chain at the amino terminus. These antibiotics were heavily used in the 1960s, but in the 1970s their clinical use was limited due to serious issues of nephrotoxicity and neurotoxicity (Biswas, S., et al., Expert Rev. Anti. Infect. Ther. 2012, 10:917-34; dx.doi.org/10.1155/2015/679109. The revival of these two peptides began in the mid-1990s, due to the lack of novel antibiotics effective against the increasingly-prevalent multi-drug resistant Gram-negative bacteria. Thus, these compounds have become antibiotics of last resort, needed for drug resistant bacteria but associated with a high incidence of toxicity. Resistance to these polymyxins could become a major global health challenge because virtually no new antibiotics are currently available for treating serious Gram-negative infections caused by polymyxin-resistant "superbugs." Accordingly, there is a great need for additional therapeutic antimicrobial treatments effective against drug-resistant organisms.

SUMMARY

Antimicrobial peptides (AMPs) are produced by bacteria, fungi, plants, insects, amphibians, crustaceans, fish and mammals, including humans, either constitutively or in response to the presence of a microbe (Jenssen, H., et al., Clin Microbiol Rev. 2006, 19:491-511). AMPs are rapidly bactericidal and generally have broad-spectrum activity. It is believed that the antimicrobial mechanism of action of cationic AMPs does not involve a stereoselective interaction with a chiral enzyme or lipid or protein since enantiomeric forms of AMPs with all-D-amino acids have shown equal activities compared to their all-L-enantiomers (Wade, D., et al, Proc. Natl. Acad. Sci. USA 1990, 87:4761-65; Cribbs, D. H., et al., J. Biol. Chem. 1997, 272:7431-36; Hong, S. Y., et al., Biochem. Pharmacol. 1999, 58:1775-80; Wakabayashi, H., et al., Antimicrob. Agents Chemother. 1999, 43:1267-69; De Lucca, A. J., et al., Med. Mycol. 2000, 38:301-8; Bland, J. M., et al., Mol. Cell. Biochem. 2001, 218:105-11; Hamamoto, K., et al., Microbiol. Immunol. 2002, 46:741-49, Elmquist, A., et al., Biol. Chem. 2003, 384:387-93; Chen, Y., et al., Chem. Biol. Drug Des. 2006, 67:162-73). Because their mode of action involves non-specific interactions with the cytoplasmic membrane of bacteria, bacteria rarely develop resistance to them. Additionally, all D-enantiomer peptides are resistant to proteolytic enzyme degradation, which enhances their potential use as therapeutic agents in mammals. Unfortunately, native AMPs lack specificity between prokaryotic and eukaryotic cells, and are therefore too toxic to be used for systemic treatment of bacterial infections. This toxicity, which manifests as drug- and dose-limiting hemolysis of human red blood cells, has limited the development of a new class of antimicrobial agents based on these AMPs.

The present inventors have previously used an antimicrobial peptide in the D-enantiomeric configuration with one lysine substitution ("D1 (K13)") as a starting point to design antimicrobial peptides with enhanced biologic properties for Gram-negative pathogens only, rather than broad-spectrum activity (Jiang, Z., et al, Chem. Biol. Drug Des. 2011, 77:225-40). The number and location of positively charged residues on the polar and non-polar face of this AMP were studied, ultimately resulting in the development of four new antimicrobial peptides with improvements in antimicrobial activity against Gram-negative pathogens and dramatic reductions in hemolytic activity and therefore unprecedented improvements in therapeutic indices.

The inventors have also studied the antimicrobial peptides piscidin 1 and dermaseptin S4 for substitution of one or two amino acid(s) to lysine(s) at different positions in the center of their nonpolar faces to investigate the generality of the "specificity determinant" design concept to enhance or maintain antimicrobial activity and significantly improve the therapeutic index (Jiang, Z., et al., Pharmaceuticals 2014, 7:366-91).

The inventors also prepared variants in two native AMPs, piscidin 1 (isolated from mast cells of hybrid striped bass–

Morone saxatilis male×Morone chrysops female) and dermaseptin S4 (isolated from the skin of tree-dwelling, South American frogs of the Phyllomedusa species) (Jiang, Z.; Gera, L.; Mant, C. T.; Hodges, R. S., Proceedings of the 24$^{th}$ American Peptide Symposium. In Enabling peptide Research from Basic Research to Drug Discovery, Orlando, Fla. (V. Srivastava, A. Yudin and M. Lebl, editors) 2015, pp. 245-248. Published by the American Peptide Society and Propt Scientific Publishing, 2015). These variant peptides were tested for their antimicrobial activity against two different pathogens: 11 and 20 diverse clinical isolates of *A. baumannii*, and *Staphylococcus aureus* (12 Methicillin-sensitive *S. aureus* strains and 8 Methicillin/Oxacillin-resistant *S. aureus* strains), respectively. These studies showed that substitution of "specificity determinant(s)" in broad spectrum AMPs, encode selectivity for Gram-negative pathogens and simultaneously remove both Gram-positive activity and hemolytic activity of these two, diverse amphipathic alpha-helical AMPs which differ dramatically in amino acid composition, net positive charge and amphipathicity.

This disclosure provides highly effective and specific antimicrobial agents comprising peptides and peptide-containing compositions, and methods of inhibiting microorganisms, and treating a subject in need of antimicrobial therapy.

The antimicrobial peptides (AMPs) and compositions of this disclosure demonstrate activity and improved therapeutic indices against bacterial pathogens, particularly gram negative bacteria. These AMPs demonstrate the ability to not only maintain or improve antimicrobial activity against Gram-negative bacterial pathogens, but also significantly decrease the hemolysis of mammalian red blood cells. Thus, improved therapeutic indices are achieved by AMPs of this disclosure.

To overcome the significant mammalian toxicity of most of the known AMPs, the inventors developed the design concept of the "specificity determinant," which refers to the substitution of positively charged amino acid residue(s) in the non-polar face of amphipathic alpha-helical or cyclic beta-sheet antimicrobial peptides to create selectivity between eukaryotic and prokaryotic membranes; that is, the antimicrobial activity of the AMPs of this disclosure is maintained, while the hemolytic activity or cell toxicity to mammalian cells is substantially decreased or eliminated.

The inventors selected Piscidin 1 and Dermaseptin S4 as examples of native AMPs to substitute positively charged amino acid(s) at different positions in their non-polar faces to enhance or maintain antimicrobial activity and significantly improve the therapeutic index.

This disclosure provides peptide antimicrobial agents and antimicrobial peptide compositions, as well as methods of inhibiting microorganisms and treating microbial infections, particularly infections by drug-resistant microorganisms. In an aspect of the claimed methods, a subject is treated by administering an AMP or a composition comprising an AMP of this disclosure. The antimicrobial peptides (AMPs) of this disclosure demonstrate activity and improved therapeutic indices against bacterial pathogens. These AMPs may demonstrate the ability to not only maintain or improve antimicrobial activity against bacterial pathogens, including Gram-negative microorganisms such as *Acinetobacter baumannii* and *Pseudomonas aeruginosa*, but also significantly decrease hemolytic activity against human red blood cells. Thus, the AMPs of this disclosure display significantly improved therapeutic indices.

Isolated antimicrobial peptides (AMPs) of this disclosure comprise the amino acid sequence (referring to the single-letter amino acid code) of:

(SEQ ID NO: 1)
V-L-X$^2$-X$^3$-L-L-X$^4$-X$^5$-L-S-X$^6$-A-X$^7$-X$^8$-X$^9$-X$^{10}$-L-X$^{11}$-T-L-L-X$^{12}$-A-L-X$^{13}$-X$^{14}$

Wherein:
each amino acid residue is in the D-enantiomeric form;
each of X$^1$ and X$^{14}$ are independently, amino acids in the D-enantiomeric form selected from Alanine (A; Ala), Serine (S; Ser), Threonine (T; Thr), Lysine (K; Lys), Arginine (R; Arg), Ornithine (O; Orn), Diaminopropionic acid (Dpr), and Diaminobutyric acid (Dbu).

each of X$^2$, X$^4$, X$^6$, X$^{11}$ and X$^{12}$, are independently, amino acids in D-enantiomeric form selected from Alanine (A; Ala), Serine (S; Ser), Lysine (K; Lys), Arginine (R; Arg), Ornithine (O; Orn), Diaminopropionic acid (Dpr), and Diaminobutyric acid (Dbu).

each of X$^3$ and X$^{13}$ are independently, amino acids in the D-enantiomeric form selected from Serine (S; Ser), Lysine (K; Lys), Arginine (R; Arg), Ornithine (O; Orn), Diaminopropionic acid (Dpr), and Diaminobutyric acid (Dbu).

X$^5$ is an amino acid in the D-enantiomeric form selected from Serine (S; Ser), Threonine (T; Thr), Lysine (K; Lys), Arginine (R; Arg), Ornithine (O; Orn), Diaminopropionic acid (Dpr), and Diaminobutyric acid (Dbu).

each of X$^7$ and X$^{10}$ are independently, amino acids in the D-enantiomeric from selected from Alanine (A; Ala), Lysine (K; Lys), Arginine (R; Arg), Ornithine (O; Orn), Diaminobutyric acid (Dbu), and Diaminopropionic acid (Dpr).

each of X$^8$ and X$^9$ are independently, amino acids in the D-enantiomeric form selected from Alanine (A; Ala), Serine (S; Ser), Lysine (K; Lys), Arginine (R: Arg), Ornithine (O; Orn), Diaminobutyric acid (Dbu), and Diaminopropionic acid (Dpr).

The total charge on these molecules without specificity determinants at positions 13 and 16 may be either +6 or +7. The total charge on these molecules with specificity determinants may be +8 or +9. This may comprise two positively charged residues on the non-polar face ("specificity determinants") and 5 or 6 positively-charged residues on the polar face.

The peptides of this disclosure may include residues that disrupt the continuous hydrophobic surface that stabilizes the alpha-helical structure of AMPS that lack the "specificity determinants" (such as the naturally occurring peptides Piscidin 1 and/or Dermaseptin S4, and/or the all D-enantiomeric forms of these naturally occurring peptides). The peptides of this disclosure may include residues that reduce the hydrophobicity on the non-polar face and overall hydrophobicity of the peptide molecule (as measured by retention time at 25° C. by reversed-phase chromatography (RP-HPLC). The peptides of this disclosure may include residues that dramatically reduce peptide self-association in aqueous conditions (as measured by the temperature profiling in RP-HPLC procedure described in the Examples section of this disclosure). The peptides of this disclosure may have dramatically reduced toxicity to normal cells (as measured by hemolytic activity to human red blood cells at 37° C. after 18 hours). The peptides of this disclosure may have similar or substantially enhanced antimicrobial activity (compared to AMPs lacking specificity determinants, such as the naturally occurring peptides Piscidin 1 and/or Dermaseptin S4, and/or the all D-enantiomeric forms of these naturally occurring peptides), and particularly with respect to bactericidal activity towards Gram-negative microbes. The peptides of this disclosure may have dramatically improved therapeutic indices (calculated by the ratio of hemolytic activity and antimicrobial activity (MIC)) compared to AMPs lacking specificity determinants, such as the naturally occurring peptides Piscidin 1 and/or Dermaseptin S4, and/or the all D-enantiomeric forms of these naturally occurring peptides. The peptides of this disclosure may have antimicrobial selectivity for Gram-negative pathogens resulting from significantly decreased Gram-positive activity and hemolytic activity (compared to AMPs lacking specificity determinants, such as the naturally-occurring peptides Piscidin 1 and/or Dermaseptin S4, and/or the all D-enantiomeric forms of these naturally occurring peptides). The peptides of this disclosure may have antimicrobial activity against *A. baumannii* bacterial strains resistant to polymyxin B and/or polymyxin E (Colistin) antibiotics. The peptides of this disclosure may discriminate between eukaryotic and prokaryotic cell membranes. The peptides of this disclosure may have antimicrobial activity even in the presence of human serum.

In aspects of the antimicrobial peptides, the AMPs of this disclosure comprise the 26-mer peptides (except the 18-mer control peptide) of Table 1A (each of which comprises the listed amino acids, set forth in the one-letter amino acid code, all in the D-enantiomeric form):

TABLE 1A

| Laboratory Name | Sequence | SEQ ID NO |
|---|---|---|
| | 1  3 4  7 8   11 13141516 18 22 25  26<br>$X^1LX^2X^3LLX^4X^5LSX^6AX^7X^8X^9X^{10}LX^{11}TLLX^{12}ALX^{13}X^{14}$ | 1 |
| D37 | ALKSLLKTLSKAAAAALKTLLKALSK | 2 |
| D38 | ALKSLLKTLSAAAKKALATLLKALSK | 3 |
| D39 | ALKSLLATLSKAAKKALKTLLAALSK | 4 |
| D40 | ALASLLKTLSKAAKKALKTLLKALSA | 5 |
| D33 (D37(A13K/A16K)) | ALKSLLKTLSKAKAAKLKTLLKALSK | 6 |
| D34 (D38(A13K/A16K)) | ALKSLLKTLSAAKKKKLATLLKALSK | 7 |
| D35 (D39(A13K/A16K)) | ALKSLLATLSKAKKKKLKTLLAALSK | 8 |
| D36 (D40(A13K/A16K)) | ALASLLKTLSKAKKKKLKTLLKALSA | 9 |
| D41 (D33(S4K)) | ALKKLLKTLSKAKAAKLKTLLKALSK | 10 |
| D42 (D33(T8K)) | ALKSLLKKLSKAKAAKLKTLLKALSK | 11 |
| D43 (D33(S25K)) | ALKSLLKTLSKAKAAKLKTLLKALKK | 12 |
| D44 (D37(S4K)) | ALKKLLKTLSKAAAAALKTLLKALSK | 13 |
| D45 (D37(T8K)) | ALKSLLKKLSKAAAAALKTLLKALSK | 14 |
| D46 (D37(S25K)) | ALKSLLKTLSKAAAAALKTLLKALKK | 15 |
| Control | ELEKGGLEGEKGGKELEK | 16 |

A series of peptides (shown in Table 1B) were designed and tested to show the effects of substitutions to the specificity determinants at positions 13 and 16 of these 26-mer AMPS. The lysine residues at these positions were substituted with Ornithine (Orn), Diaminopropionic acid (Dpr), Diaminobutyric acid (Dbu), or Arginine (Arg). In Table 1B, the 26-mer peptide sequences are shown using the one-letter code (or three-letter code for Orn, Dpr, Dbu, and Arg); Ac denotes $N^\alpha$-acetyl and amide denotes $C^\alpha$-amide. Positions 13 and 16 are in the center of the non-polar face (FIGS. 1 and 2). These positions are Lys residues for peptide D41, and Orn residues for peptide D74, and Dbu residues for peptide D75, and Arg residues for peptide D76, and Dpr residues for peptide D83.

TABLE 1B

D41 non-polar face substitutions in net charge +9 analogs.

| Laboratory Name | Sequence | SEQ ID NO |
|---|---|---|
| |                           13      16<br>ALKKLLKTLSKA $X^1$ AA $X^2$ LKTLLKALSK | 17 |
| D41 | Tic-ALKKLLKTLSKA(Lys)AA(Lys)LKTLLKALSK-amide | 18 |
| D74 (D41K13Orn/K16Orn) | Tic-ALKKLLKTLSKA(Orn)AA(Orn)LKTLLKALSK-amide | 19 |
| D75 (D41K13Dbu/K16Dbu) | Tic-ALKKLLKTLSKA(Dbu)AA(Dbu)LKTLLKALSK-amide | 20 |
| D76 (D41K13Arg/K16Arg) | Tic-ALKKLLKTLSKA(Arg)AA(Arg)LKTLLKALSK-amide | 21 |
| D83 (D41K13Dpr/K16Dpr) | Tic-ALKKLLKTLSKA(Dpr)AA(Dpr)LKTLLKALSK-amide | 22 |

A series of peptides (shown in Table 1C) were designed and tested to show the effects of substitutions to lysine residues on the polar face (at positions 3, 7, 11, 18, 22, and 26) of the 26-mer AMPS (such as any one of D33, D34, D35, or D36). The lysine residues at these positions were substituted with Ornithine (Orn), Diaminopropionic acid (Dpr), Diaminobutyric acid (Dbu), or Arginine (Arg). In Table 1C and FIG. 3, the 26-mer peptide sequences are shown using the one-letter code (or three-letter code for Orn, Dpr, Dbu, and Arg); Ac denotes $N^\alpha$-acetyl and -amide denotes $C^\alpha$-amide. Specificity determinants (K) at positions 13 and 16 are held constant in the center of the non-polar face. Lys residues on the polar face of the amphipathic α-helix were substituted at positions 3, 7, 11, 18, 22 and 26 for peptide D84, and positions 3, 7, 14, 15, 22, and 26 for peptide D88; Orn residues for peptide D85; Dbu residues for peptides D86 and D89; Arg residues for peptide D87; and Dpr residues for peptides D105 and D106.

TABLE 1C

Polar face substitutions in +9 charged AMPs

| Laboratory Name | Sequence | SEQ ID NO |
|---|---|---|
| |    1  3       7     11        18      22      26<br>KL $X^1$ SLL $X^2$ TLS $X^3$ AKAAKL $X^4$ TLL $X^5$ ALS $X^6$ | 23 |
| D84 (D33(A1K)) | Ac-KL(Lys)SLL(Lys)TLS(Lys)AKAAKL(Lys)TLL(Lys)ALS(Lys)-amide | 24 |
| D85 (D84K3OrnK7Orn K11OrnK18Orn K22OrnK26Orn) | Ac-KL(Orn)SLL(Orn)TLS(Orn)AKAAKL(Orn)TLL(Orn)ALS(Orn)-amide | 25 |
| D86 ((D84K3DbuK7Dbu K11DbuK18Dbu K22DbuK26Dbu) | Ac-KL(Dbu)SLL(Dbu)TLS(Dbu)AKAAKL(Dbu)TLL(Dbu)ALS(Dbu)-amide | 26 |
| D87 (D84K3ArgK7Arg K11ArgK18Arg K22ArgK26Arg) | Ac-KL(Arg)SLL(Arg)TLS(Arg)AKAAKL(Arg)TLL(Arg)ALs(Arg)-amide | 27 |
| D105 (D84K3DprK7Dpr K11DprK18Dpr K22DprK26Dpr) | Ac-KL(Dpr)SLL(Dpr)TLS(Dpr)AKAAKL(Dpr)TLL(Dpr)ALS(Dpr)-amide | 28 |
| |    1  3       7          14 15        22    26<br>KL $X^1$ SLL $X^2$ TLSAAK $X^3$ $X^4$ KLATLL $X^5$ ALS $X^6$ | 29 |
| D88 (D34(A1K)) | Ac-KL(Lys)SLL(Lys)TLSAAK(Lys)(Lys)KLATLL(Lys)ALS(Lys)-amide | 30 |
| D89 (D88K3Dbu K7DbuK14Dbu K15DbuK22Dbu K26Dbu) | Ac-KL(Dbu)SLL(Dbu)TLSAAK(Dbu)(Dbu)KLATLL(Dbu)ALS(Dbu)-amide | 31 |

TABLE 1C-continued

Polar face substitutions in +9 charged AMPs

| Laboratory Name | Sequence | SEQ ID NO |
|---|---|---|
| D106 (D88K3Dpr K7DprK14Dpr K15DprK22Dpr K26Dpr) | Ac-KL(Dpr)SLL(Dpr)TLSAAK(Dpr)(Dpr)KLATLL(Dpr)ALs(Dpr)-amide | 32 |

Another series of peptides (shown in Table 1D) were designed and tested to show the effects of substitutions to lysine residues on the polar face (at positions 3, 7, 11, 18, and 22) of the 26-mer AMPS. The lysine residues at these positions were substituted with Ornithine (Orn), Diaminopropionic acid (Dpr), Diaminobutyric acid (Dbu), or Arginine (Arg). In Table 1D, the 26-mer peptide sequences are shown using the one-letter code (or three-letter code for Orn, Dpr, Dbu, and Arg); Ac denotes $N^\alpha$-acetyl and -amide denotes $C^\alpha$-amide. Specificity determinants (K) at positions 13 and 16 are held constant in the center of the non-polar face. Lys residues on the polar face of the amphipathic α-helix (peptides D101 and D103) were substituted with Dbu residues at positions 3, 7, 11, 18, and 22 for peptide D102, and positions 3, 7, 14, 15, and 22 for peptide D104.

TABLE 1D

Polar face substitutions in +8 charged AMPs

| Laboratory Name | Sequence | SEQ ID NO |
|---|---|---|
| | 1  3    7    11    18    22   26<br>KL $X^1$ SLL $X^2$ TLS $X^3$ AKAAKL $X^4$ TLL $X^5$ ALSS | 33 |
| D101 (D33(A1K)K26S) | Ac-KL(Lys)SLL(Lys)TLS(Lys)AKAAKL(Lys)TLL(Lys)ALSS-amide | 34 |
| D102 ((D101K3Dbu K7DbuK11Dbu K18DbuK22Dbu) | Ac-KL(Dbu)SLL(Dbu)TLS(Dbu)AKAAKL(Dbu)TLL(Dbu)ALSS-amide | 35 |
| | 1  3    7      14 15    22   26<br>KL $X^1$ SLL $X^2$ TLSAAK $X^3$ $X^4$ KLATLL $X^5$ ALSS | 36 |
| D103 (D34(A1K)K26S) | Ac-KL(Lys)SLL(Lys)TLSAAK(Lys)(Lys)KLATLL(Lys)ALSS-amide | 37 |
| D104 (D103(K26S)K3Dbu K7DbuK14Dbu K15DbuK22Dbu) | Ac-KL(Dbu)SLL(Dbu)TLSAAK(Dbu)(Dbu)KLATLL(Dbu)ALSS-amide | 38 |

Another aspect of this disclosure provides pharmaceutical compositions comprising at least one of the antimicrobial peptides of this disclosure, and a pharmaceutically acceptable carrier. In aspects of these pharmaceutical compositions, the compositions may include one or more AMPs having the amino acid sequence of SEQ ID NOS: 2-15, 18-22, 24-32, and 34-38.

Another aspect provides methods of preventing or treating an infection in a subject, including administering a therapeutically effective amount of a composition to the subject, wherein the composition comprises at least one antimicrobial peptide of this disclosure, and a pharmaceutically acceptable carrier. In these methods, the infecting microorganism may be Gram-negative bacteria. In these methods, the infecting microorganism may be an antibiotic resistant microbe. The antibiotic resistant microbe may be a Gram-negative, antibiotic-resistant *Acinetobacter baumannii* or *Pseudomonas aeruginosa* pathogen. Alternatively or additionally, the antibiotic infecting microorganism may be a drug-resistant Gram-negative pathogen (such as a polymyxin B and/or polymyxin E (Colistin)-resistant pathogen), or a polymyxin B and/or polymyxin E sensitive Gram-negative pathogen.

This disclosure also provides methods of inhibiting a microorganism, comprising contacting the microorganism with a composition comprising at least one AMP of this disclosure. In these methods, the AMP may be one or more of the peptides having the amino acid sequence of SEQ ID NOS: 2-15, 18-22, 24-32, and 34-38. In these methods, the AMP inhibits propagation of a prokaryote. The prokaryote may be a Gram-negative bacterium, which may include at least one of *A. baumannii* and *P. aeruginosa* bacterium.

One aspect of this disclosure provides an antimicrobial peptide (AMP) comprising an amino acid sequence having at least 85%, or at least 90%, or at least 95% sequence homology with a peptide selected from the group consisting of SEQ ID NOS:2-15, 18-22, 24-32, and 34-38, or functional analogues, derivatives, or fragments thereof, or pharmaceutically-acceptable salts thereof.

The AMPs of this disclosure may exhibit a therapeutic index (calculated by the ratio of hemolytic activity to antimicrobial activity (MIC)) of at least 70. The AMPs of this disclosure may exhibit therapeutic index of between 70 and 1600. The AMPs of this disclosure may exhibit therapeutic index of between 700 and 1600. The AMPs of this disclosure may exhibit therapeutic index of between 960 and 1600.

The AMPs of this disclosure may exhibit at least a 10-fold increased selectivity for Gram-negative bacteria over Gram-positive bacteria. The AMP may exhibit between a 10-fold and a 90-fold increase in selectivity for Gram-negative bacteria over Gram-positive bacteria. The AMP may exhibit between a 16-fold and an 88-fold increase in selectivity for Gram-negative bacteria over Gram-positive bacteria. In these selectivity measurements, the Gram-negative bacteria may be *A. baumannii* and the Gram-positive bacteria may be *Staphylococcus aureus*.

The AMPs of this disclosure having the sequence of any one of SEQ ID NOs: 26, 31, 35, and 38 may exhibit at least a 5-fold decrease in hemolysis of human red blood cells (measured as $HC_{30}$—the concentration of peptide that results in 30% hemolysis after 18 h at 37° C.) compared to hemolysis exhibited by any one of SEQ ID NOs:24, 30, 34, or 37. The AMPs of this disclosure having the sequence of any one of any one of SEQ ID NOs: 26, 31, 35, and 38, may exhibit about a 10 to 45-fold decrease in hemolysis of human red blood cells compared to hemolysis exhibited by any one of SEQ ID NOs:24, 30, 34, or 37.

Another aspect of this disclosure provides a pharmaceutical composition comprising at least one AMP of this disclosure and a pharmaceutically acceptable carrier. The pharmaceutical composition may be a mono-phasic pharmaceutical composition suitable for parenteral or oral administration consisting essentially of a therapeutically-effective amount of at least one AMP of this disclosure, and a pharmaceutically acceptable carrier. In these embodiments, the AMP may be one or more of the peptides having the sequence of SEQ ID NOS: 2-15, 18-22, 24-32, and 34-38.

Another aspect of this disclosure provides methods of preventing or treating a microbial infection comprising administering to a subject in need thereof a therapeutically effective amount of at least one AMP of this disclosure, or a pharmaceutical composition comprising the same. In these methods, the AMP administered may be one or more of the peptides having the sequence of SEQ ID NOS: 2-15, 18-22, 24-32, and 34-38. In these methods, the microbial infection may be the result of an infecting bacteria, fungi, virus, or protozoa. The microbial infection may be a bacterial infection. The bacterial infection may be a Gram-negative bacterial infection. The bacterial infection may be an antibiotic resistant bacterial infection. The infecting microorganism may be at least one of *Pseudomonas aeruginosa, Acinetobacter baumannii*. The infecting microorganism may be an antibiotic- or multi drug-resistant *Pseudomonas aeruginosa*, or *Acinetobacter baumannii* bacteria.

In these methods, the administration of the peptide or pharmaceutical composition may be made by an administration route selected from oral, topical, subcutaneous, intravenous, intraperitoneal, intramuscular, intradermal, intrasternal, intraarticular injection, and/or intrathecal. These peptides or pharmaceutical compositions may be administered in conjunction with one or more additional antimicrobial agents.

This disclosure also provides methods of preventing a microbial infection, or reducing the incidence of microbial infection, or slowing the growth of a microbial infection, in an individual comprising, or at risk of developing an infection, comprising administering an effective amount of at least one AMP of this disclosure, or a pharmaceutical composition comprising the same, to the individual in need thereof. The individual may be a surgical patient. The individual may be a hospitalized patient.

This disclosure also provides methods of combating a bacterial infection in a patient comprising applying at least one AMP of this disclosure, or a pharmaceutical composition comprising the same, to a body surface of the patient. The body surface may be a wound. The composition may be applied following an operation or surgery.

This disclosure also provides at least one AMP of this disclosure, or a pharmaceutical composition comprising the same, for use in the treatment of a microbial infection. This disclosure also provides the use of at least one peptide of this disclosure, or a pharmaceutical composition comprising the same, in the manufacture of a medicament for the prevention or treatment of a microbial infection.

BRIEF DESCRIPTION OF THE FIGURES

FIG. 8 presents this comparison for peptides D84, D85, D86, D87, and D105. FIG. 9 presents this comparison for peptides D88, D89, and D106. FIG. 10 presents this comparison for peptides D101, D102, D103, and D104. FIG. 11 presents this comparison for peptides D86, D86PEG1, and D86PEG2.

FIG. 12A shows the m-dPEG24-acid which adds a MW of $C_{50}H_{98}O_{25}$: 1099.29 to the N-terminal of the antimicrobial peptide. FIG. 12B shows the Fmoc-amido-dPEG24-acid which can be added to the α-amino group of the peptide. FIG. 12C shows that removal of the Fmoc group and compiling of m-dPEG24-acid extends the length of PEG on the peptide and adds $C_{101}H_{199}NO_{50}$: 2227.63 to the N-terminal of the antimicrobial peptide. FIG. 12D shows the tribranched PEG which adds $C_{104}H_{201}N_5O_{49}$: 2305.70 to the N-terminal of the antimicrobial peptide.

DETAILED DESCRIPTION

Figure 1A:
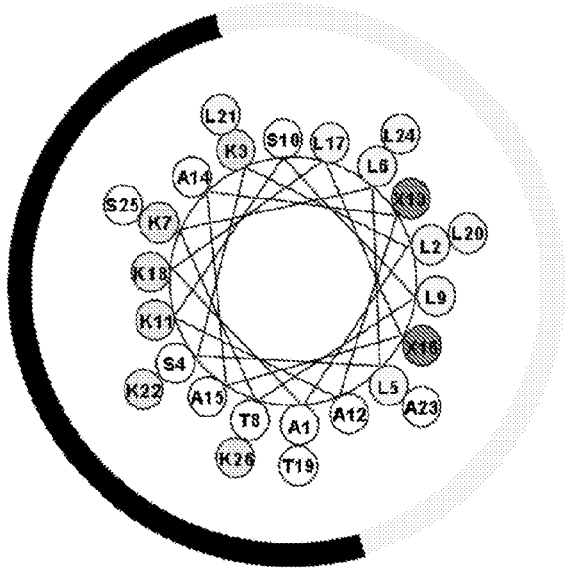
FIGS. 1A-1C provide helical wheel and helical net representations of helical AMPS with, and without "specificity determinants." In the helical wheels (FIG. 1A), the non-polar face is indicated as a light arc and the polar face is indicated as a black arc. In the helical nets of FIGS. 1B and 1C, the residues on the polar face (FIG. 1B) are boxed and the residues on the non-polar face are circled (FIG. 1C). The locations of the six positively charged Lys residues on the polar face are different between peptides D33, D34, D35, and D36, and similarly between peptides D37, D38, D39, and D40. The potential i to i+3, or i to i+4 electrostatic repulsions between positively charged residues are shown as black dotted lines. The i to i+3, or i to i+4 hydrophobic interactions between large hydrophobes are shown as solid black lines.
Figure 1A:
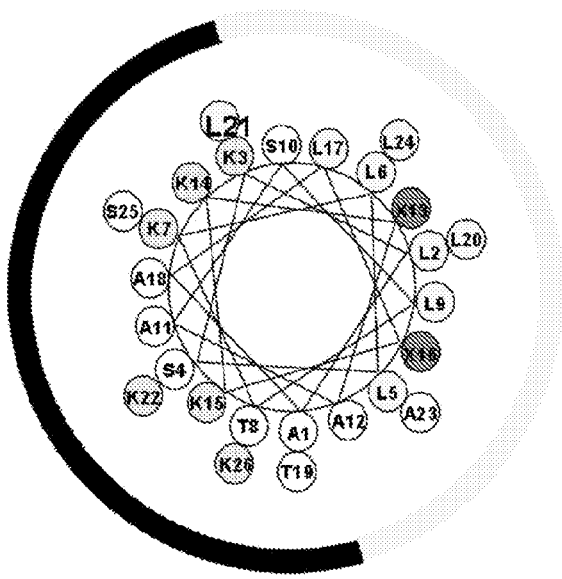
Figure 1A:
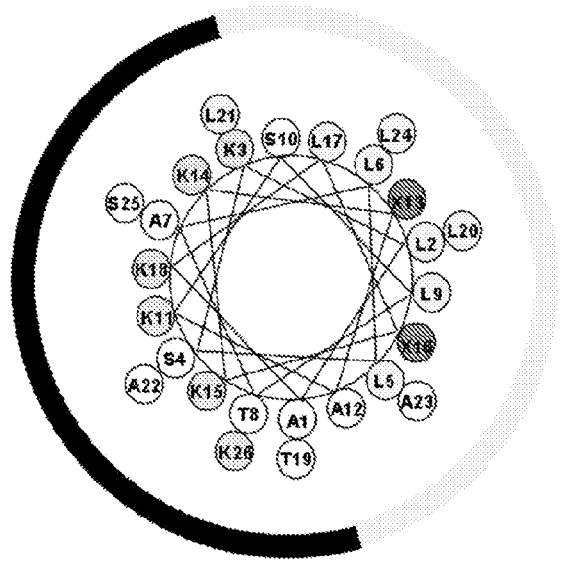
Figure 1A:
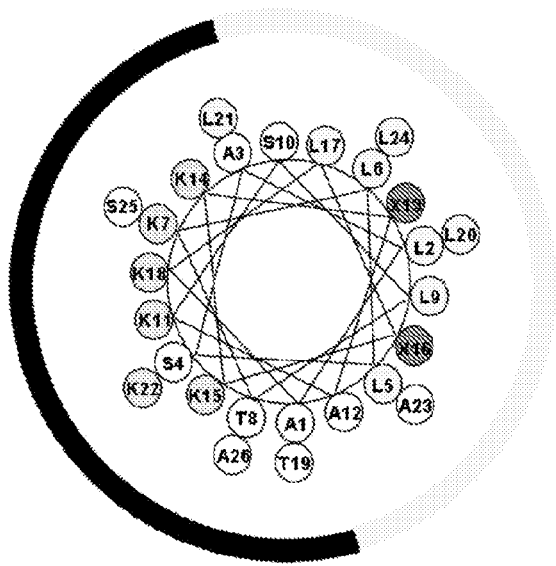

The terms and phrases used herein have their art-recognized meaning, which can be found by reference to standard texts, journal references and contexts known to those skilled in the art.

As used herein, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "containing" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the pertinent art.

Whenever a range of values is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be optionally replaced with either of the other two terms, thus describing alternative aspects of the scope of the subject matter. The invention illustratively described herein suitably may be practiced in the absence of any element or elements, limitation or limitations which is not specifically disclosed herein.

The following definitions are provided to clarify use of these terms in the context of this disclosure.

When used herein, the term "amino acid" is intended to refer to any natural or unnatural amino acid, whether made naturally or synthetically, including those in the L- or D-enantiomeric configurations. The term can also encompass amino acid analog compounds used in peptidomimetics or in peptoids. The term can include a modified or unusual amino acid or a synthetic derivative of an amino acid, e.g. diamino butyric acid and diamino propionic acid and the like. The antimicrobial peptides comprise amino acids linked together by peptide bonds. The peptides are in general in alpha helical conformation under hydrophobic conditions. Sequences are conventionally given from the amino terminus to the carboxyl terminus. Unless otherwise noted, the amino acids are L-amino acids. When all the amino acids are of L-configuration, the peptide is said to be an L-enantiomer. When all the amino acids are of D-configuration, the peptide is said to be a D-enantiomer.

The term "hemolytic concentration-30" or "$HC_{30}$" refers to the peptide concentration that causes 30% hemolysis of erythrocytes after 18 h. $HC_{30}$ was determined from a plot of percent lysis versus peptide concentration (μM). For comparison, the inventors also determined the hemolytic activity after 18 hours at 37° C. Hemolysis can be determined with red blood cells (RBC) from various species including human red blood cells (hRBC). Therapeutically effective AMPs of this disclosure are, in most instances, so non-hemolytic to mammalian red blood cells that the $HC_{50}$ value could not be calculated. Therefore, the $HC_{30}$ value was used for testing and comparison purposes to achieve a measure of safety, with respect to hemolysis, that is consistent and comparable across peptides of this disclosure and those known in the art. Similarly, $HC_{50}$ is the concentration of peptide that results in 50% hemolysis of human red blood cells after 18 hours at 37° C.

The term "therapeutic index" (TI) is the ratio of $HC_{30}$ over minimal inhibitory concentration (MIC) of an antimicrobial agent. Larger values generally indicate greater antimicrobial specificity.

The term "stability" can refer to an ability to resist degradation, to persist in a given environment, and/or to maintain a particular structure. For example, a peptide property of stability can indicate resistance to proteolytic degradation and to maintain an alpha-helical structural conformation.

The following abbreviations are useful: A, Ala, Alanine; M, Met, Methionine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; N, Asn, Asparagine; O, Orn, Ornithine; P, Pro, Proline; Q, Gln, Glutamine; R, Arg, Arginine; S, Ser, Serine; T, Thr, Threonine; V, Val, Valine; W, Trp, Tryptophan; Y, Tyr, Tyrosine; Dbu, 2,4-Diaminobutyric acid; Dpr, 2,3-Diaminopropionic acid; RP-HPLC, reversed-phase high performance liquid chromatography; MIC, minimal inhibitory concentration; $HC_{30}$ hemolytic concentration-30; $HC_{50}$ hemolytic concentration-50; CD, circular dichroism spectroscopy; TFE, 2,2,2-trifluoroethanol; TFA, trifluoroacetic acid; RBC, red blood cells; hRBC, human red blood cells.

The term "antimicrobial activity" refers to the ability of a peptide to modify a function or metabolic process of a target microorganism, for example to at least partially affect replication, vegetative growth, toxin production, survival, viability in a quiescent state, or other attribute. The term relates to inhibition of growth of a microorganism. In aspects of the claimed peptides and methods, antimicrobial activity relates to the ability of a peptide to kill at least one bacterial species. The bacterial species may be a Gram-negative bacteria. The term can be manifested as microbicidal or microbistatic inhibition of microbial growth.

The phrase "improved biological property" is meant to indicate that a test peptide exhibits less hemolytic activity and/or better antimicrobial activity, or better antimicrobial activity and/or less hemolytic activity, compared to a control peptide (e.g., D-Piscidin 1 or D-Dermaseptin S4), when tested by the protocols described herein or by any other art-known standard protocols. In general, the improved biological property of the peptide is reflected in the therapeutic index (TI) value which is better than that of the control peptide.

The term "microorganism" herein refers broadly to bacteria, fungi, viruses, and protozoa. In particular, the term is applicable for a microorganism having a cellular or structural component of a lipid bilayer membrane. The membrane may be a cytoplasmic membrane. Pathogenic bacteria, fungi, viruses, and protozoa as known in the art are generally encompassed. Bacteria can include Gram-negative and Gram-positive bacteria in addition to organisms classified in orders of the class Mollicutes and the like, such as species of the *Mycoplasma* and *Acholeplasma* genera. Specific examples of Gram-negative bacteria include, but are not limited to, *Escherichia coli, Pseudomonas aeruginosa, Acinetobacter baumannii, Salmonella* spp., *Haemophilus influenzae, Neisseria* spp., *Vibrio cholerae, Vibrio parahaemolyticus* and *Helicobacter pylori*. Examples of Gram-positive bacteria include, but are not limited to, *Staphylococcus aureus, Staphylococcus epidermidis, Streptococcus agalactiae*, Group A *Streptococcus, Streptococcus pyogenes, Enterococcus faecalis*, Group B Gram-positive *Streptococcus, Corynebacterium xerosis*, and *Listeria monocytogenes*. Examples of fungi include yeasts such as *Candida albicans*. Examples of viruses include measles virus, herpes simplex virus (HSV-1 and -2), herpes family members (HIV, hepatitis C, vesicular stomatitis virus (VSV), visna virus, and cytomegalovirus (CMV). Examples of protozoa include Giardia.

"Therapeutically effective amount" as used herein, refers to an amount of formulation, composition, or reagent in a pharmaceutically acceptable carrier or a physiologically acceptable salt of an active compound that is of sufficient quantity to ameliorate the undesirable state of the patient, animal, material, or object so treated. "Ameliorate" refers to a lessening of the detrimental effect of the disease state or disorder, or reduction in contamination, in the receiver of the treatment.

"Pharmaceutical agent or drug" as used herein, refers to a chemical compound or composition capable of inducing a desired therapeutic or prophylactic effect when properly administered to a subject.

"Pharmaceutically acceptable carrier" as used herein, refers to conventional pharmaceutical carriers useful in the methods disclosed herein. Remington's Pharmaceutical Sciences, by E. W. Martin, Mack Publishing Co., Easton, Pa., 15th Edition (1975), describes compositions and formulations suitable for pharmaceutical delivery of TCR peptides and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Antimicrobial peptides (AMPs) of this disclosure have antimicrobial activity by themselves, or when covalently conjugated or otherwise coupled or associated with another molecule, e.g., polyethylene glycol or a carrier protein such as bovine serum albumin, so long as the peptides are positioned such that they can come into contact with a cell or unit of the target microorganism. These peptides may be modified by methods known in the art provided that the antimicrobial activity is not destroyed or substantially compromised. Thus, also contemplated within the context of the inventive AMPs, methods, and compositions of this disclosure is the modification of any antimicrobial peptide described herein, by chemical or genetic means. Examples of such modification include construction of peptides of partial or complete sequence with non-natural amino acids and/or natural amino acids in L or D enantiomeric forms. Furthermore, the polypeptides may be modified to contain carbohydrate or lipid moieties, such as sugars or fatty acids, covalently linked to the side chains or the N- or C-termini of the amino acids. In addition, the polypeptides may be modified by glycosylation and/or phosphorylation. In addition, the polypeptides may be modified to enhance solubility and/or half-life upon being administered. For example, polyethylene glycol (PEG) and related polymers have been used to enhance solubility and the half-life of protein therapeutics in the blood. Accordingly, the antimicrobial peptides of this disclosure may be modified by PEG polymers and the like. "PEG" or "PEG polymers" means a residue containing poly(ethylene glycol) as an essential part. Such a PEG can contain further chemical groups which are necessary for the therapeutic activity of the peptides of this disclosure; which results from the chemical synthesis of the molecule; or which is a spacer for optimal distance of the parts of the molecule from one another. In addition, such a PEG can consist of one or more PEG side-chains which are linked together. PEG groups with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEGs usually have 2 to 8 arms and are described in, for example, U.S. Pat. No. 5,932,462. Especially preferred are PEGs with two PEG side-chains (PEG2) linked via the primary amino groups of a lysine (Monfardini, C, et al., Bioconjugate Chem. 6 (1995) 62-69). The term "PEG" is used broadly to encompass any polyethylene glycol molecule, wherein the number of ethylene glycol (EG) units is at least 460, preferably 460 to 2300 and especially preferably 460 to 1840 (230 EG units refers to a molecular weight of about 10 kDa). The upper number of EG units is only limited by solubility of the PEGylated peptides of this disclosure. Usually PEGs which are larger than PEGs containing 2300 units are not used. Preferably, a PEG used in the invention terminates on one end with hydroxy or methoxy (methoxy PEG, mPEG) and is on the other end covalently attached to a linker moiety via an ether oxygen bond. The polymer is either linear or branched. Branched PEGs are e.g. described in Veronese, F. M., et al., Journal of Bioactive and Compatible Polymers 12 (1997) 196-207. Suitable processes and preferred reagents for the production of PEGylated peptides and variants of this disclosure are described in US Patent Pub. No. 2006/0154865. It is understood that modifications, for example, based on the methods described by Veronese, F. M., Biomaterials 22 (2001) 405-417, can be made in the procedures so long as the process results in PEGylated peptides of this disclosure. Particularly preferred processes for the preparation of PEGylated peptides of this disclosure are described in US Patent Publication No. 2008/0119409, which is incorporated herein by reference.

Additionally or alternatively, the antimicrobial peptides of this disclosure may be fused to one or more domains of an Fc region of human IgG proteins. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337:525-31). When constructed together with an antimicrobial protein of this disclosure, an Fc domain can provide longer half-life or incorporate such functions as Fc receptor binding, protein A binding, complement fixation, and perhaps even blood-brain barrier, or placental transfer. In one example, a human IgG hinge, CH2, and CH3 region may be fused at either the amino-terminus or carboxyl-terminus of the peptides of this disclosure using methods known to the skilled artisan. The resulting fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

The polypeptides may also be modified to contain sulfur, phosphorous, halogens, metals, etc. Amino acid mimics may be used to produce polypeptides, and therefore, the polypeptides of this disclosure may include amino acid mimics that have enhanced properties, such as resistance to degradation.

The peptides of this disclosure may be isolated or purified. These peptides may be synthetic and can be produced by peptide synthesis techniques or by recombinant expression technology as understood in the art. As used herein, the term "purified" can be understood in to refer to a state of enrichment or selective enrichment of a particular component relative to an earlier state of crudeness or constituency of another component. This term can be considered to correspond to a material that is at least partially purified as opposed to a state of absolute purity. For example, a peptide composition may be considered purified even if the composition does not reach a level of one hundred percent purity with respect to other components in the composition.

As used herein, the term "specificity determinant(s)" refers to positively charged amino acid residue(s) (including, for example, lysine, arginine, ornithine, diaminopropionic acid, or diaminobutyric acid) in the non-polar face of AMPS that could decrease hemolytic activity/toxicity but increase or maintain the same level of antimicrobial activity, thus increasing the therapeutic index of the AMP.

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of that group and all subgroups, including any isomers, enantiomers, and diastereomers of the group members, are disclosed separately.

When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually, or in any combination. Additionally, unless otherwise specified, all isotopic variants of compounds disclosed herein are intended to be encompassed by the disclosure. As a brief illustration, it will be understood that any one or more hydrogens in a molecule disclosed can be replaced with deuterium or tritium.

Isotopic variants of a molecule are generally useful as standards in assays for the molecule and in chemical and biological research related to the molecule or its use. Methods for making such isotopic variants are known in the art.

One of ordinary skill in the art will appreciate that starting materials, biological and chemical materials, biological and chemical reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this disclosure.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, although the invention has been disclosed by various aspects that may include preferred embodiments and aspects, modifications and variations of the concepts herein disclosed may be resorted to by those skilled in the art. Such modifications and variations are considered to be within the scope of this invention as defined by the appended claims.

Compositions of this Disclosure

When employed as pharmaceuticals, especially as antimicrobial agents administered to mammals, the AMPs of this disclosure are administered in the form of pharmaceutical compositions. These compounds can be administered by a variety of routes including oral, rectal, transdermal, subcutaneous, intravenous, intramuscular, intrathecal, and intranasal. Such pharmaceutical compositions are prepared in a manner well known in the pharmaceutical art and comprise at least one AMP of this disclosure.

The pharmaceutical compositions of the present invention contain, as the active ingredient, one or more of the AMPs of this disclosure, associated with pharmaceutically acceptable formulations. In making the compositions of this invention, the active ingredient is usually mixed with an excipient, diluted by an excipient or enclosed within a carrier which can be in the form of a capsule, sachet, paper or other container. An excipient is usually an inert substance that forms a vehicle for a drug. When the excipient serves as a diluent, it can be a solid, semi-solid, or liquid material, which acts as a vehicle, carrier or medium for the active ingredient. Thus, the compositions can be in the form of solutions, syrups, aerosols (as a solid or in a liquid medium), ointments containing, for example, up to 30% by weight of the active compound, soft and hard gelatin capsules, suppositories, sterile injectable solutions, and sterile packaged powders.

In preparing a formulation, it may be necessary to mill active compounds of this disclosure to provide the appropriate particle size prior to combining with the other ingredients. If the antimicrobial peptide is substantially insoluble, it ordinarily is milled to a particle size of less than 200 mesh. If the compound(s) is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, gum Arabic, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of this disclosure can be formulated to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active AMP(s).

Formulations of this disclosure suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of this disclosure for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials may be used for such enteric layers or coatings, including a number of polymeric acids and mixtures of polymeric acids with such materials as shellac, cetyl alcohol, and cellulose acetate.

Liquid dosage forms for oral administration of the compounds of this disclosure include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor, sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of this disclosure for rectal or vaginal administration may be presented as a suppository, which may be prepared by mixing one or more compounds of this disclosure with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active AMP(s) may be mixed under sterile conditions with a pharmaceutically-acceptable carrier, and with buffers or propellants that may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays may also contain customary propellants such as chlorofluorohydrocarbons and volatile unsubstituted hydrocarbons, such as butane and propane.

Transdermal patches have the added advantage of providing controlled delivery of compounds of this disclosure to the body. Such dosage forms can be made by dissolving, dispersing or otherwise incorporating one or more compounds of this disclosure in a proper medium, such as an elastomeric matrix material. Absorption enhancers can also be used to increase the flux of the compound across the skin. The rate of such flux can be controlled by providing a rate-controlling membrane or dispersing a compound in a polymer matrix or gel.

Pharmaceutical formulations include those suitable for administration by inhalation or insufflation or for nasal or intraocular administration. For administration to the upper (nasal) or lower respiratory tract by inhalation, the compounds of this disclosure are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of this disclosure and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of this disclosure may be administered by means of nose drops or a liquid spray such as a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of this disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Suitable alkalinizing agents include alkali metal salts and alkaline earth metal salts. The alkali metal salts include sodium carbonate, sodium hydroxide, sodium silicate, disodium hydrogen orthophosphate, sodium aluminate, and other suitable alkali metal salts or mixtures thereof. Suitable alkaline metal salts include calcium carbonate, calcium hydroxide, magnesium carbonate, magnesium hydroxide, magnesium silicate, magnesium aluminate, aluminum magnesium hydroxide or mixture thereof. More particularly, calcium carbonate, potassium bicarbonate, calcium hydroxide, and/or sodium carbonate may be used as alkalinizing agents to obtain a formulation pH within the desired pH range of pH 8 to pH 13. The concentration of the alkalinizing agent is selected to obtain the desired pH, varying from about 0.1% to about 30%, by weight, and more preferably from about 12.5% to about 30%, by weight, of the total weight of the dosage formulation.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

Methods for Preventing and Treating Microbial Infection

Another aspect of this disclosure provides methods for preventing and treating a microbial infection. These methods include administering to a subject in need thereof a therapeutically effective amount of a peptide or composition of this disclosure that kills or inhibits the growth of infectious microbes, thereby inhibiting or treating the microbial infections. The infecting microorganism may include Gram-negative bacteria.

The infecting microorganism may be a Gram-negative bacteria, which may include, but is not limited to, *Escheri-* chia coli, Pseudomonas aeruginosa, Acinetobacter baumannii, Salmonella spp., Haemophilus influenzae, Neisseria spp., Vibrio cholerae, Vibrio parahaemolyticus and Helicobacter pylori.

The antimicrobial peptides administered, preferably as a component of a pharmaceutical composition, can include a single antimicrobial peptide of this disclosure, or multiple peptides of this disclosure. The peptides may include peptides having at least 85%, or at least 90%, or at least 95% homology to a peptide sequence of SEQ ID NOs:2-15, and which effectively treat or prevent a microbial infection. The peptides may include fragments of the peptides of SEQ ID NOs:2-15 that retain the ability to effectively treat or prevent a microbial infection. Exemplary peptides include the amino acid sequences set forth in SEQ ID NOs: 26, 28, 31, 35, and 38.

Therapeutic AMPs of this disclosure may be administered by a number of routes, including orally, topically, or parenteral administration, including for example, intravenous by injection or infusion, intraperitoneal, intramuscular, intradermal, intrathecal, intrasternal, intraarticular, or subcutaneous injection. One of skill in the art can readily determine the appropriate route of administration.

The therapeutically effective amounts of the AMPs of this disclosure that inhibit or kill an infecting microorganism will depend upon the subject being treated, the severity and type of the infection, and the manner of administration. For example, a therapeutically effective amount of a peptide of this disclosure can vary from about 1 microg/injection up to about 10 mg/injection. The exact amount of the peptide is readily determined by one of skill in the art based on the age, weight, sex, and physiological condition of the subject. Effective doses can be extrapolated from dose-response curves derived from in vitro or animal model test systems.

One or more peptides of this disclosure that effectively inhibit or kill an infecting microorganism can be administered in conjunction with one or more additional pharmaceutical agents. The additional pharmaceutical agents can be administered at the same time as, or sequentially with, the peptide(s) of this disclosure. The additional pharmaceutical agent may be an additional antimicrobial agent. When administered at the same time, the additional pharmaceutical agent(s) can be formulated in the same composition that includes the peptide(s) of this disclosure.

Those skilled in the art can determine an appropriate time and duration of therapy that includes the administration of a peptide of this disclosure to achieve the desired preventative or ameliorative effects on the subject treated.

The invention now being generally described will be more readily understood by reference to the following examples, which are included merely for the purposes of illustration of certain aspects of the invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

Peptide Design, Specificity Determinants and Amphipathicity

As noted above, enantiomeric forms of AMPs with all-D-amino acids have shown equal activities to their all-L-enantiomers. The advantage of all-D-peptides is that they are resistant to proteolytic enzyme degradation, which enhances their potential as therapeutic agents. In these studies, the inventors de novo designed, synthesized, purified and characterized eight all-D amphipathic alpha-helical antimicrobial peptides, four without specificity determinants (denoted D37, D38, D39 and D40), and four with specificity determinants (denoted D33, D34, D35 and D36) (peptide sequences shown in Table 1A).

Solid-phase Peptide Synthesis: Standard solid-phase peptide synthesis methodology using 9-fluorenylmethoxycarbonyl (Fmoc) chemistry and rink-amide-4-methylbenzhydrylamine hydrochloride (rink-amide-MBHA) resin (peptides D33-D36) or Rink Amide-ChemMatrix® resin (Biotage, Charlotte, N.C.) (peptides D37-D40) using a Focus-XC peptide synthesizer (Aapptec, Louisville, Ky.). The coupling procedure used (Benzotriazol-1-yloxy)tris(dimethylamino) phosphonium hexafluorophosphate (Bop)/hydroxybenzotriazole (HOBt) in dimethylformamide (DMF) with N,N-diisopropylethylamine (DIPEA) in N-methyl-2-pyrrolidinone (NMP) with the first coupling, and the second coupling at 50° C., for one hour each. The deprotection procedure (removal of Fmoc protecting group) was carried out by treatment of the resin with 0.1 M HOBt in DMF with 20% piperidine. After completion of the synthesis, the peptide resin was dried under vacuum and the peptide was cleaved from the resin with a mixture of 90% trifluoroacetic acid (TFA), 5% water and 5% triisopropylsilane (TIS) for 1-2 h. The resin was removed by filtration and peptide was precipitated with ice-cooled ethyl ether on ice for 1-2 h. The pellet was spun down and redissolved in acetonitrile/water (1:1, with 0.2% TFA) and the solution lyophilized to obtain the crude peptide.

Determination of Peptide Amphipathicity: Amphipathicity of peptides at pH 7 and pH 2 was determined by the calculation of hydrophobic moment (Eisenberg, D., et al., Nature 1982, 299, 371-74), using the software package EMBOSS 6.5.7 and the Hmoment application, modified to include hydrophobicity scales determined in the inventors' laboratory (Kovacs, J. M., et al., Biopolymers 2006, 84, 283-97; Mant, C. T., et al., Biopolymers 2009, 92, 573-95). The hydrophobicity scales used in this study are listed as follows: At pH 7, Trp, 33.0; Phe, 30.1; Leu, 24.6; Ile, 22.8; Met, 17.3; Tyr, 16.0; Val, 15.0; Pro, 10.4; Cys, 9.1; His, 4.7; Ala, 4.1; Thr, 4.1; Arg, 4.1; Gln, 1.6; Ser, 1.2; Asn, 1.0; Gly, 0.0; Glu, −0.4; Asp, −0.8 and Lys, −2.0 (polar face), Lys, -18.48 (center of non-polar face). These hydrophobicity coefficients were determined from RP-HPLC at pH 7 (10 mM $PO_4$ buffer containing 50 mM NaCl) of a model random coil peptide with a single substitution of all 20 naturally occurring amino acids. At pH 2, these coefficients were determined in 20 mM trifluoroacetic acid (TFA), Trp, 32.4; Phe, 29.1; Leu, 23.3; Ile, 21.4; Met, 15.7; Tyr, 14.7; Val, 13.4; Pro, 9.0; Cys, 7.6; Ala, 2.8; Glu, 2.8; Thr, 2.3; Asp, 1.6; Gln, 0.6; Ser, 0.0; Asn, −0.6; Gly, 0.0; Arg. 0.6; His, 0.0; Lys, 2.8 (polar face), Lys, −18.48 (center of non-polar face). These HPLC-derived scales reflect the relative difference in hydophilicity/hydrophobicity of the 20 amino acid sidechains more accurately than previously determined scales (see recent review where this scale was compared to other scales; Mant, C. T., et al., Biopolymers 2009, supra). The hydrophobicity/hydrophilicity coefficients for Lys residues in the center of the non-polar face at pH 2.0 and pH 7.0 were assigned values of −18.48 determined by reversed-phase chromatography of the identical peptides where Ala was substituted by Lys on the non-polar face at position 13 and 16. Position X was placed in the sequence where these values are to be used in the Hmoment calculations when Lys is in the center of the non-polar face.

Figure 1B:
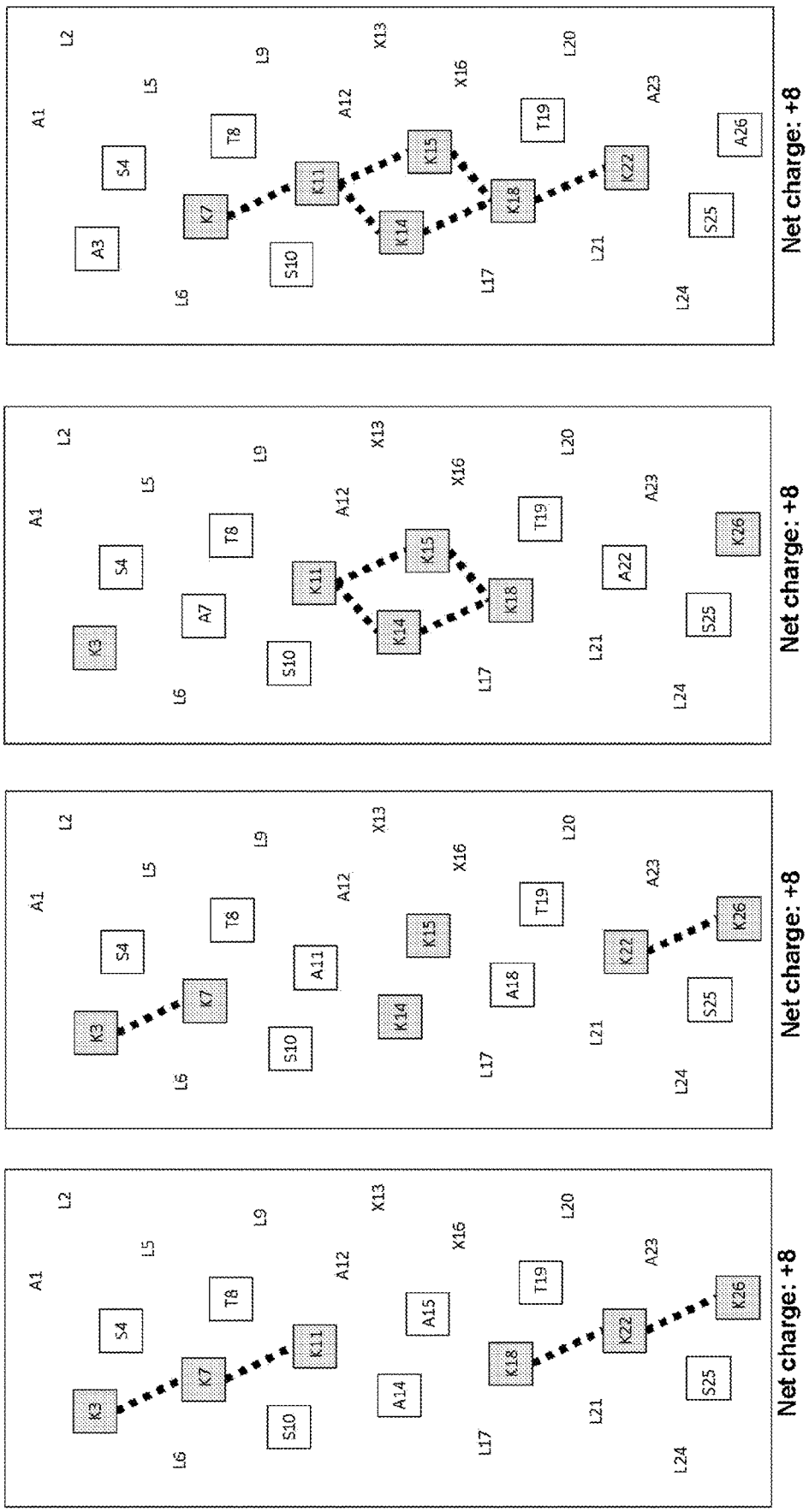
Figure 1C:
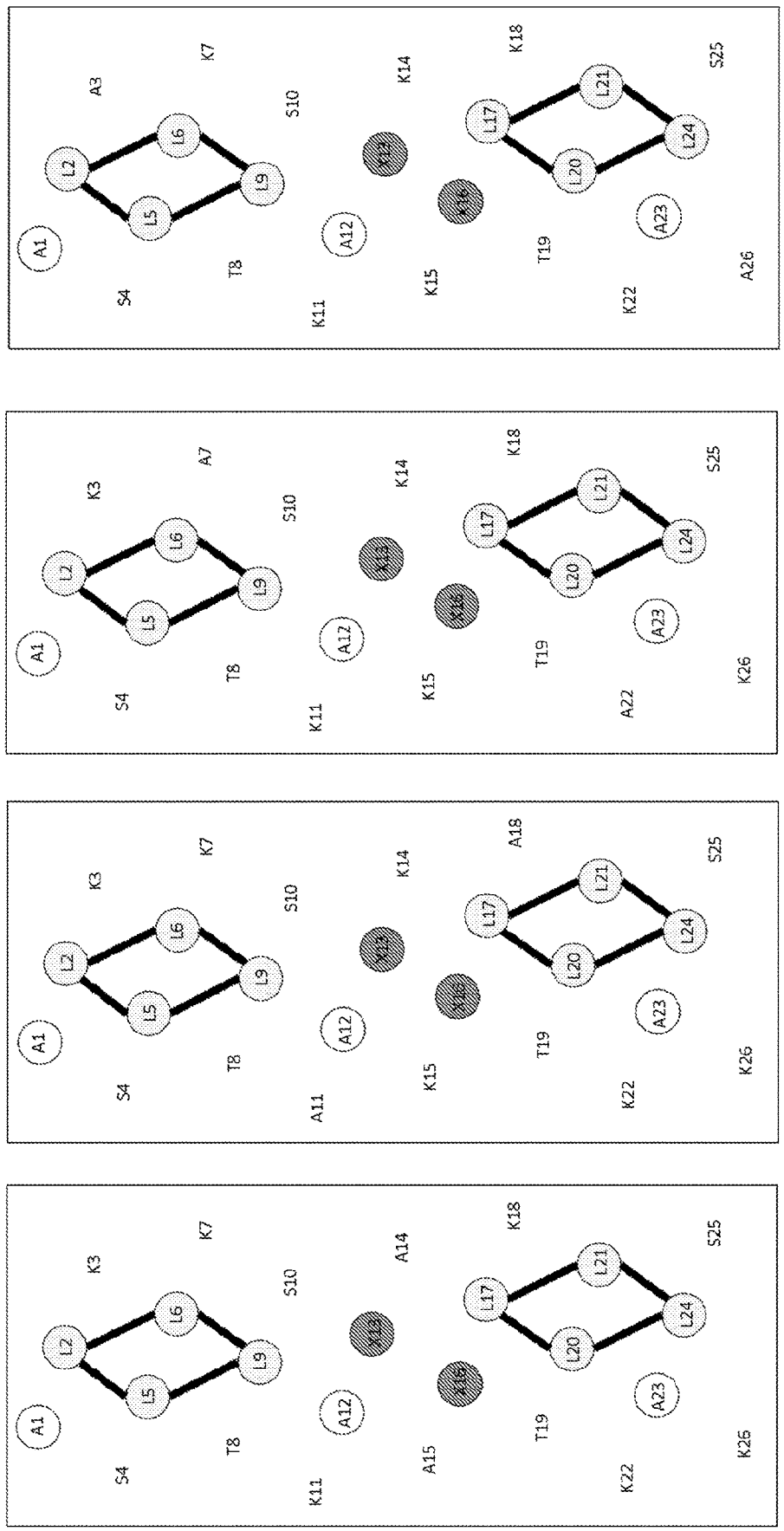
Figure 2:
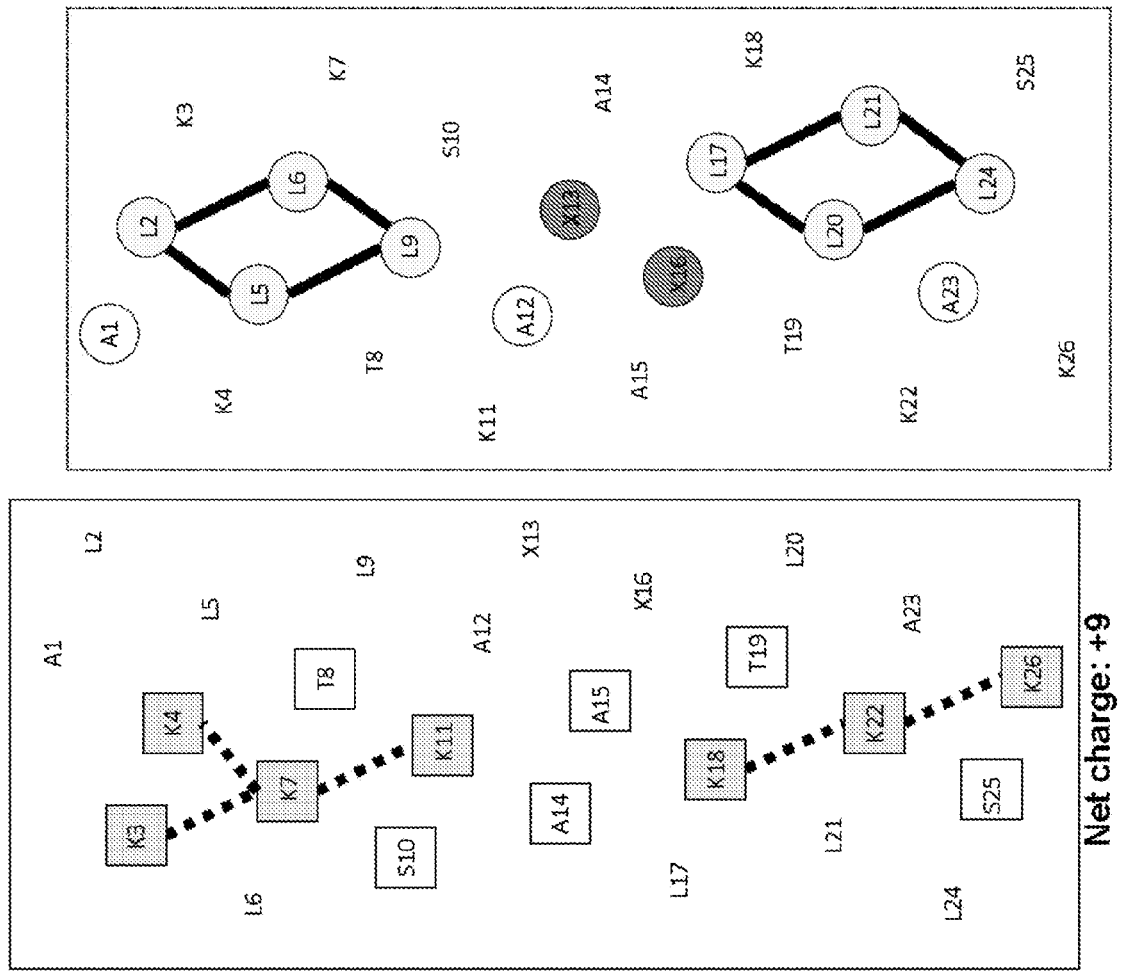
FIG. 2 similarly shows helical wheel (left) and helical net (middle and right) representations of helical AMPS with and without specificity determinants. In the helical wheel (left), the non-polar face is indicated as a light arc and the polar face is indicated as a black arc. In the helical nets (middle and right), the residues on the polar face are boxed and the residues on the non-polar face are circled. The two non-polar face residues (13 and 16) labeled X, are both Lysine (Lys) amino acids in peptide D41; are both Ornithine (Orn) amino acids in peptide D74; are both Diaminobutyric acid (Dbu) amino acids in peptide D75; are both Arginine (Arg) amino acids in peptide D76; are both Diaminopropionic acid (Dpr) amino acids in peptide D83. The potential i to i+3, or i to i+4 electrostatic repulsions between positively charged residues are shown as black dotted lines. The i to i+3, or i to i+4 hydrophobic interactions between large hydrophobes are shown as solid black lines.

FIGS. 1 and 2 show the amino acid sequences in helical wheel and helical net representations. The inventors have displayed two versions of the helical nets wherein the polar residues are displayed along the center of the helical net (FIG. 1B) and where the non-polar residues are displayed along the center of the helical net (FIG. 1C). Peptides D37, D38, D39 and D40 are all very amphipathic alpha-helical peptides with amphipathicity values ranging from 5.275 to 5.555 at pH 7 (Table 2). These four peptides have a net positive charge of +6 and vary from one another by the arrangement of the six positively charged Lys residues on the polar face (FIG. 1B). The hydrophobic/non-polar faces of these four peptides are identical (FIG. 1C). FIG. 1C shows the same four peptides where each peptide has two Lys residues ("specificity determinants") in the center of the non-polar face (colored pink) replacing Ala residues in D37 to D40. These two Lys residues dramatically change the amphipathicity of these peptides, as expected, due to locating two very hydrophilic and positively charged residues on the non-polar face. These four peptides have a net positive charge of +8. The amphipathicity of peptides D33, D34, D35 and D36 vary from 3.921 to 4.185 at pH 7 as shown in Table 2 and are dramatically different from the peptides without specificity determinants. Each of the following peptide pairs, D33 and D37, D34 and D38, D35 and D39 and D36 and D40 have identical polar faces and the positions of the two Lys residues ("specificity determinants") are identical in D33, D34, D35 and D36 (positions 13 and 16 in the center of the non-polar face). The non-polar faces of these four peptides are identical. The polar faces are different and depend on the location of the six Lys residues. These representations in FIGS. 1A-1C allow easy comparison of different analogs and these sequence differences will be used to explain their biological and biophysical properties described below.

specificity determinants; 2) reduce the hydrophobicity on the non-polar face and overall hydrophobicity as measured by retention time at 25° C. by reversed-phase chromatography (RP-HPLC); 3) dramatically reduce peptide self-association in aqueous conditions as measured by a novel procedure developed in the inventors' laboratory referred to as temperature profiling in RP-HPLC (Chen, Y., et al., Chem. Biol. Drug Des. 2006; Jiang, Z., et al., Pharmaceuticals, 2014; Chen, Y., et al., Antimicrob. Agents Chemother. 2007; Jiang, Z., et al., Biol. Drug Des. 2008; Jiang, Z., et al., Protein Pept. Lett. 2011; Jiang, Z., et al., Biopolymers 2008, 90:369-83); 4) dramatically reduce toxicity to normal cells as measured by hemolytic activity to human red blood cells; 5) maintain or enhance antimicrobial activity; 6) dramatically improve the therapeutic indices of AMPs with specificity determinants compared to AMPs lacking these determinants; 7) the AMPs with specificity determinants encode selectivity for Gram-negative pathogens by significantly decreasing Gram-positive activity and hemolytic activity; 8) the AMPs are active against *A. baumannii* strains resistant to polymyxin B and polymyxin E (Colistin); 9) the specificity determinants allow the AMPs to discriminate between eukaryotic and prokaryotic cell membranes; 10) the specificity determinants ensure excellent antimicrobial activity in the presence of human serum. In the current study de novo designed AMPs were tested against seven diverse clinical isolates of the Gram-negative pathogen *A. baumannii* and seven *A. baumannii* strains resistant to polymyxin B and polymyxin E (Colistin). In addition, the inventors tested these AMPs against six diverse clinical isolates of the Gram-negative pathogen, *P. aeruginosa*, and nine Gram-positive methicil-

TABLE 2

Biopysical Data

| Peptide name | Net charge | Hydrophobicity $t_R{}^a$ (min) | Benign $(\theta)_{222}{}^b$ | % Helix$^c$ | 50% TFE $(\theta)_{222}{}^b$ | % Helix$^c$ | $\Delta[\theta]_{222}$ TFE-benign | $Tp^d$ (° C.) | $P_A{}^e$ | Amphipathicity$^f$ pH 7 | pH 2 |
|---|---|---|---|---|---|---|---|---|---|---|---|
| Without specificity determinants |||||||||||||
| D37 | +6 | 112.7 | 13,200 | 35.2 | 25,000 | 66.7 | 11,800 | 53 | 18.5 | 5.424 | 4.525 |
| D38 | +6 | 112.5 | 22,800 | 60.9 | 37,450 | 100.0 | 14,650 | 45 | 19.5 | 5.275 | 4.525 |
| D39 | +6 | 116.6 | 23,700 | 63.2 | 36,150 | 96.5 | 12,450 | 49 | 18.5 | 5.326 | 4.525 |
| D40 | +6 | 117.5 | 22,350 | 59.7 | 35,750 | 95.3 | 13,400 | 49 | 18.7 | 5.555 | 4.525 |
| Average |  | 114.8 | 20,513 | 54.8 | 33,588 | 89.7 | 13,075 | 49 | 18.8 | 5.395 | 4.525 |
| With specificity determinants |||||||||||||
| D33 | +8 | 77.4 | 5,900 | 15.8 | 22,000 | 58.7 | 16,100 | 33 | 5.3 | 4.061 | 3.327 |
| D34 | +8 | 77.2 | 8,800 | 23.5 | 26,500 | 70.8 | 17,100 | 33 | 5.7 | 3.921 | 3.327 |
| D35 | +8 | 78.3 | 10,000 | 26.7 | 34,750 | 92.8 | 14,750 | 33 | 5.5 | 3.970 | 3.327 |
| D36 | +8 | 79.0 | 5,700 | 15.2 | 26,100 | 69.7 | 20,400 | 33 | 5.6 | 4.185 | 3.327 |
| Average |  | 78.0 | 7,600 | 20.3 | 27,338 | 73.0 | 17,088 | 33 | 5.5 | 4.034 | 3.327 |

$^a$tR denotes retention time in RP-HPLC at pH 2 at a temperature of 25 C., and is a measure of overall peptide hydrophobicity.
$^b$The mean residue molar ellipticities [θ]222 (deg cm2/dmol) at a wavelength 222 nm were measured at 5° C. in benign conditions. (100 mM KCl, 50 mM Na2HPO4/NaH2PO4, pH 7.0) or in benign buffer containing 50% trifluoroethanol (TFE) by circular dichroism spectroscopy.
$^c$The helical content (as a percentage) of a peptide relative to the molar ellipticity value of peptides D38 in the presence of 50% TFE.
$^d$Tp temperature at which maximum retention time is observed over the temperature range 5-77° C. during temperature profiling in RP-HPLC.
$^e$PA denotes the self-association parameter (dimerization/oligomerization) of each peptide during RP-HPLC temperature profiling, which is the maximal retention time difference of (tRt-tR5 for peptide analogs) – (tRt-tR5 for control peptide RC) within the temperature range; tRt-tR5 is the retention time difference of a peptide at a specific temperature (tRt) compared with that at 5° C. (tR5). (The sequence of the random coil peptide (RC) is shown in Table 1A).
$^f$Amphipathicity was determined by calculation of the hydrophobic moment using hydrophobicity coefficients determined by RPHPLC.

The design concept of "specificity determinants" (positively charged lysine residues in the center of the non-polar face of amphipathic alpha-helical AMPs) was introduced previously to achieve the following biophysical and biological properties: 1) disrupt the continuous hydrophobic surface that stabilizes the alpha-helical structure of the AMPs that lack lin-sensitive *S. aureus* clinical isolates and eight Gram-positive methicillin/oxacillin-resistant *S. aureus* strains. This testing allows for the determination of pathogen selectivity between Gram-negative and Gram-positive pathogens as the location of the positively charged residues on the polar face is varied.

Example 2

Peptide Hydrophobicity

Retention behavior in RP-HPLC is an excellent method to represent overall peptide hydrophobicity. Retention times of peptides are highly sensitive to the conformational status of the peptides upon interaction with the hydrophobic environment of the column matrix (Jiang, Z., et al., Chem. Biol. Drug Des. 2011; Chen, Y., et al., J. Peptide Research 2002, supra). The non-polar faces of amphipathic alpha-helical and amphipathic cyclic beta-sheet peptides represent a preferred binding domain for interaction with the hydrophobic matrix of the reversed-phase column (Zhou, N. E., et al., Peptide Research 1990, 3:8-20). In this study, the observed peptide hydrophobicity was determined by RP-HPLC retention time as described in the methods section and are relative hydrophobicities because they are dependent on the TFA concentration and organic solvent in the mobile phase, gradient rate, temperature, flow rate and the column used.

Analytical and Preparative Purification by Reversed-phase Chromatography: Analytical RP-HPLC: Column, Luna C18 (2), 250×4.6 mm I.D., 5 μm particle size, 100 Å pore size from Phenomenex. Run conditions: linear AB gradient (1% acetonitrile/min, starting from 2% acetonitrile) at a flow-rate of 1 ml/min, where eluent A is 0.2% aq. TFA and eluent B is 0.18% TFA in acetonitrile; temperature, 30° C. Preparative RP-HPLC: Peptides were dissolved in 0.2% aq. TFA containing 2% acetonitrile to a final concentration of 10 mg/ml. Following filtration through a 0.45 μm Millipore filter and subsequently through a 0.22 micron filter, the peptide solutions were loaded onto the column via multiple 20-ml injections into a 20-ml injection loop at a flow-rate of 5 ml/min. Column, Luna C18 (2), 250×30 mm I.D., 10 um particle size, 100 Å pore size from Phenomenex. Run conditions: 2% acetonitrile/min gradient up to an acetonitrile concentration 15% below that required to elute the peptide during analytical RP-HPLC, then shallow gradient elution (0.1% acetonitrile/min) at a flow-rate of 10 ml/min (same eluents as shown above for analytical RP-HPLC); temperature, room temperature.

The retention times of the 4 parent antimicrobial peptides lacking specificity determinants, D37, D38, D39 and D40, have only hydrophobic residues on the non-polar face of the helix (8 Leu residues, colored yellow in two clusters (L2, L4, L6 and L9 in the N-terminal cluster and L17, L20, L21 and L24 in the C-terminal cluster and 4 Ala residues, FIG. 1C). Even though this hydrophobic surface on the non-polar face is the preferred binding domain, the overall hydrophobicity is also affected by the composition of residues on the polar face and their positions. The amino acid composition on the polar face is identical on all four peptides and the difference between peptides is the location of the six positively charged Lys residues (FIG. 1B). Thus, overall hydrophobicity varied from 112.5 to 117.5 min (Table 2), showing that the subtle changes in location of positively charged residues on the polar face affect overall hydrophobicity.

The retention times of the four AMPS with specificity determinants, D33, D34, D35 and D36, have two lysine residues in the center of the non-polar face (Lys 13 and Lys 16) that replaced Ala 13 and Ala 16 in peptides D37, D38, D39 and D40 (FIG. 1C). These two Lys residues increase the net positive charge on the peptides from +6 to +8 and dramatically affect the overall hydrophobicity, which varied from 77.2 to 79.0 min, Table 2. The large hydrophobicity change between the two sets of peptides is the result of two lysine residues located in the center of the non-polar face. Peptides D33 and D37, D34 and D38, D35 and D39 and D36 and D40 have identical polar faces and identical positions of the two Lys residues or "specificity determinants" at positions 13 and 16 in the center of the non-polar face. The differences in overall hydrophobicity between D33 and D37 is 35.3 min, between D34 and D38 is 35.3 min, between D35 and D39 is 38.3 min and between D36 and D40 is 38.5 min. These peptide pairs have identical polar faces and differ by either two Lys residues or two Ala residues at positions 13 and 16 in the center of the non-polar face. Thus, the effect of the two specificity determinants on the non-polar face is extremely large (average of 36.85 min for the four peptide pairs compared to the positional effects of Lys residues on the polar face which give a range of 5.0 min for D37 to D40 and a range of 1.8 min for D33 to D36 (Table 2). This emphasizes that changes on the non-polar face are dramatically larger than changes on the polar face in affecting overall hydrophobicity as would be expected since the non-polar face is the preferred binding domain in RP-HPLC.

Example 3

Peptide Secondary Structure

Characterization of Helical Structure: The mean residue molar ellipticities of peptides were determined by circular dichroism (CD) spectroscopy, using a Jasco J-815 spectropolarimeter (Jasco Inc. Easton, Md., USA) at 5° C. under benign (non-denaturing) conditions (50 mM $NaH_2PO_4$/$Na_2HPO_4$/100 mM KCl, pH 7.0), hereafter referred to as benign buffer, as well as in the presence of an alpha-helix inducing solvent, 2,2,2-trifluoroethanol, TFE, (50 mM $NaH_2PO_4$/$Na_2HPO_4$/100 mM KCl, pH 7.0 buffer/50% TFE). A 10-fold dilution of an approximately 500 μM stock solution of the peptide analogs was loaded into a 0.1 cm quartz cell and its ellipticity scanned from 195 to 250 nm. Peptide concentrations were determined by amino acid analysis.

Table 2 shows the circular dichroism spectroscopy results for the 8 peptide analogs used in this study in benign (non-denaturing) conditions of pH 7 (50 mM $PO_4$, 100 mM KCl) and in the presence of 50% trifluoroethanol (TFE), a mimic of the hydrophobicity and the alpha-helix inducing ability of the membrane (benign buffer containing 50% TFE). The objective of substituting two Lys residues in the center of the non-polar face was to disrupt the continuous hydrophobic surface on the non-polar face which stabilizes the alpha-helical structure. Compare these peptides in FIGS. 1A-1C where the two Lys residues disrupt the continuous hydrophobic surface along the helix on the non-polar face. The average molar ellipticity at 222 nm of peptides D37 to D40 in benign conditions decreased from 20,513 to 7,600 for peptides D33 to D36 with the two Lys residues in the center of the non-polar face (Table 2). This shows that there is a dramatic decrease in helical content when the two specificity determinants are added from an average $[\theta]_{222}$ of 20,513 to 7,600 in benign conditions or the average % helix changes from 54.8% to 20.3%. In the presence of the helical inducing solvent TFE, helical structure is induced in both series of peptides. Peptides D37 to D40 the average $[\theta]_{222}$ increases from 20,513 (average % helix 54.8) in benign conditions to 33,588 (average % helix 89.7). Similarly, peptides D33 to D36 the average $[\theta]_{222}$ increases from 7,600 (average % helix 20.3) in 50% TFE to 27,338 (average % helix 73.0) and an increase in alpha-helical content of 53%. The specificity determinants dramatically decrease alpha-helicity in benign conditions, but this helicity can be induced by increasing the hydrophobicity of the environment (50% TFE), a mimic of the hydrophobicity and helix inducing properties of the cell membrane. The inducible alpha-helix in the presence of 50% TFE increased from an average $\Delta[\theta]_{222}$ of 13,075 for peptides D37 to D40 to an average $\Delta[\theta]_{222}$ of 17,088 for peptides D33 to D36 which contain specificity determinants. Thus, the inducible alpha-helical structure is larger for peptides D33 to D36.

Example 4

Peptide Self-Association

Peptide self-association, the ability to oligomerize/dimerize in aqueous solution, is an important parameter controlling antimicrobial activity while removing toxicity. The inventors hypothesize that the monomeric random-coil antimicrobial peptides in aqueous solution are best suited to pass through a polysaccharide capsule, the outer membrane lipopolysaccharide and the cell wall peptidoglycan layer of microorganisms prior to penetration into the cytoplasmic membrane, induction of alpha-helical structure and disruption of membrane structure to kill target cells. On the other hand, if the self-association ability of an AMP in aqueous medium is too strong, stable folded oligomers/dimers through interaction of their non-polar faces are formed which decreases the ability of the AMP to dissociate to monomer and the dimer/oligomer to effectively pass through the capsule and cell wall to reach the cytoplasmic membrane. In the present study, the ability of the AMPs to self-associate was determined by a technique developed in the inventors' laboratory, referred to as RP-HPLC temperature profiling at pH 2 over the temperature range of 5° C. to 80° C. This novel method to measure self-association of small cyclic beta-sheet AMPs was first reported by Lee and co-workers in 2003 (Lee, D. L., et al., J. Biol. Chem. 2003, 278:22918-27) and is a key method in the design of amphipathic alpha-helical AMPs.

Figure 5:
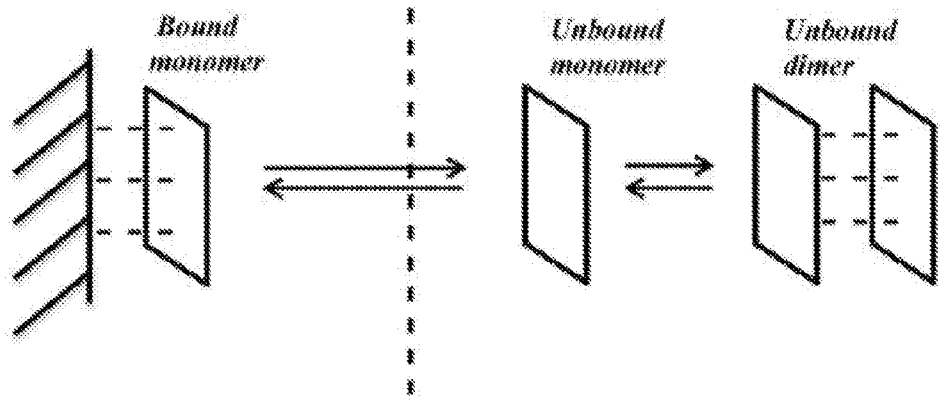
FIG. 5 depicts a proposed mechanism of temperature profiling by RP-HPLC of amphipathic alpha-helical antimicrobial peptides. Panel A, at low temperatures, peptides capable of self-association in aqueous solution by their non-polar faces establish an equilibrium during RP-HPLC between the bound helical monomer to the hydrophobic stationary phase, the helical monomer in the mobile phase and the helical dimer in the mobile phase during gradient elution. Panel B, at higher temperatures, the population of dimers in the mobile phase during partitioning decreases, increasing the concentration of the monomeric alpha-helical peptide which increases peptide retention time. Panel C, at temperatures beyond the point of maximum retention time the unbound helical peptide in the mobile phase is in equilibrium with the random-coil conformation of the peptide and retention time decreases with further increasing temperature.
Figure 5:
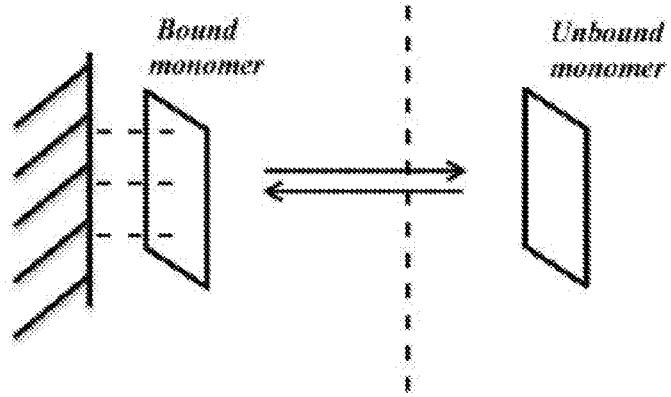
Figure 5:
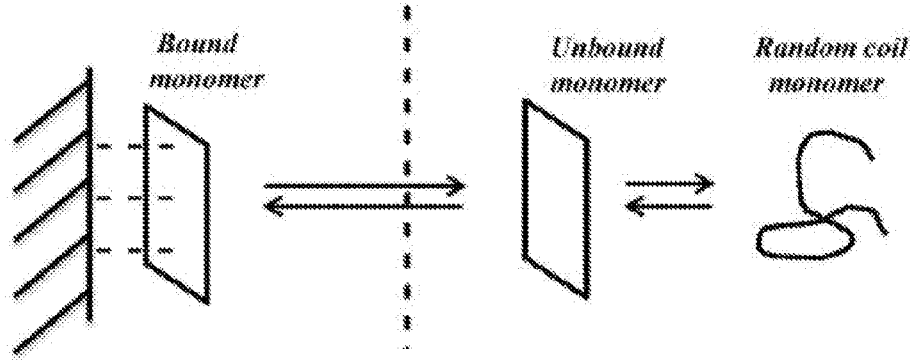

It is important to understand how the RP-HPLC temperature profiling method works. At low temperature, AMPs are capable of self-associating in aqueous solution via their non-polar faces. As shown in FIG. 5 equilibrium is established between monomer and dimer and the concentration of monomer and dimer at any given temperature depends on the strength of the hydrophobic interactions between the two monomers to form the alpha-helical folded dimer. In RP-HPLC, the hydrophobicity of the matrix disrupts or dissociates the dimer and only the monomeric form of the peptide is bound to the hydrophobic matrix by its preferred binding domain (non-polar face). The monomeric form of the peptide can partition between the hydrophobic surface of the alkyl ligands on the reversed-phase matrix and the mobile phase. At low temperature, the monomer can dimerize in the mobile phase and the retention time is decreased due to the large population of dimers in solution. At higher temperatures, the population of dimers in the mobile phase during partitioning decreases, which increases the concentration of monomeric peptide in solution and thereby increases retention time. At some higher temperature, no dimer exits in the mobile phase and the peptide has its maximum retention time. At temperatures beyond the point of maximum retention time the unbound helical peptide in the mobile phase is in equilibrium with the random-coil conformation of the peptide and retention time decreases with further increasing temperature. With the random coil control peptide that does not dimerize, the peptide binds to the stationary phase and partitions in the mobile phase as a monomer with undefined structure throughout the temperature range (5° C.-80° C.) (FIG. 4).

Temperature Profiling of Peptides on Reversed-phase HPLC: Purified peptides were analyzed on an Agilent 1200 series liquid chromatograph for temperature profiling using a Zorbax 300 SB-C8 column (150 mm×2.1 mm I.D.; 5 µm particle size, 300 Å pore size) from Agilent Technologies. Conditions: linear AB gradient (0.5% acetonitrile/min) and a flow rate of 0.30 ml/min, where eluent A was 0.20% aqueous TFA, pH 2 and eluent B was 0.18% TFA in acetonitrile. Temperature profiling was carried out on two mixtures of peptides; mixture 1 consisted of peptides RC, D33, D35, D37, and D39 and mixture 2 consisted of RC, D34, D36, D38 and D40. Both mixtures were run at each temperature in 4° C. increments from 5° C. to 77° C. (19 different temperatures). Twenty minutes was allowed between runs for temperature equilibration. RC denotes a random coil peptide of 18 residues.

Figure 6:
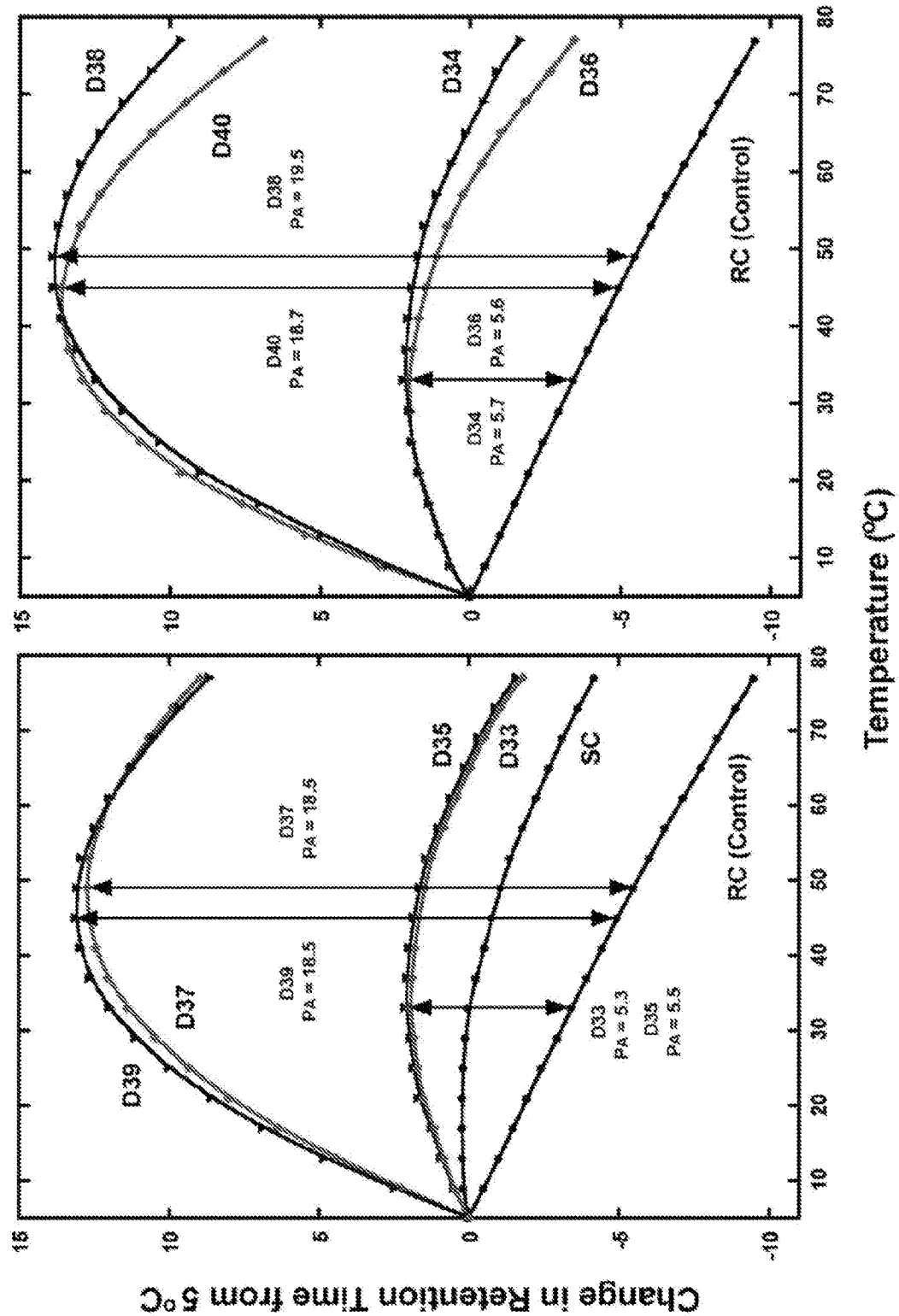
FIG. 6 shows temperature profiling (5° C.-77° C.) in RP-HPLC of peptides D33, D35, D37, D39, and analogs D34, D36, D38, and D40.

FIG. 6 shows the retention behavior of four AMPs without specificity determinants (D37, D38, D39 and D40) and four AMPs with specificity determinants (D33, D34, D35 and D36) (FIG. 1A) over the temperature range of 5° C. to 77° C. in 4° C. increments from 5° C. The eight AMPs are compared to a random-coil control peptide denoted RC. RC is a monomeric random-coil peptide in both aqueous and hydrophobic media and shows a linear decrease in retention time with increasing temperature and is representative of peptides which have no ability to self-associate during RP-HPLC. This linear decrease in retention time with increasing temperature represents the general effects of temperature due to greater solute diffusivity and enhanced mass transfer between the stationary and mobile phase. The difference in retention time between the RC control peptide and the amphipathic alpha-helical antimicrobial peptides is a measure of peptide association. The association parameter, $P_A$, is large for AMPs D37, D38, D39 and D40, ranging from 18.5 to 19.5 min. (Table 2) and is shown by the double headed arrows (FIG. 6). The association parameter, $P_A$, is dramatically smaller for the AMPs D33, D34, D35 and D36, which have two Lys residues in the center of the non-polar face (Lys 13 and Lys 16) and range from 5.3 to 5.7 min. (Table 2). Thus, the specificity determinants lower self-association, which is a desired property of effective AMPs. That is, effective AMPs will have low self-association in aqueous medium to more easily pass through the capsule and cell wall to reach the cytoplasmic membrane where the AMPs must be able to be induced into alpha-helical structure by the hydrophobicity of the membrane. The inventors have shown that when AMPs strongly associate by having a hydrophobic face that is too hydrophobic the AMPs are inactive.

Figure 7:
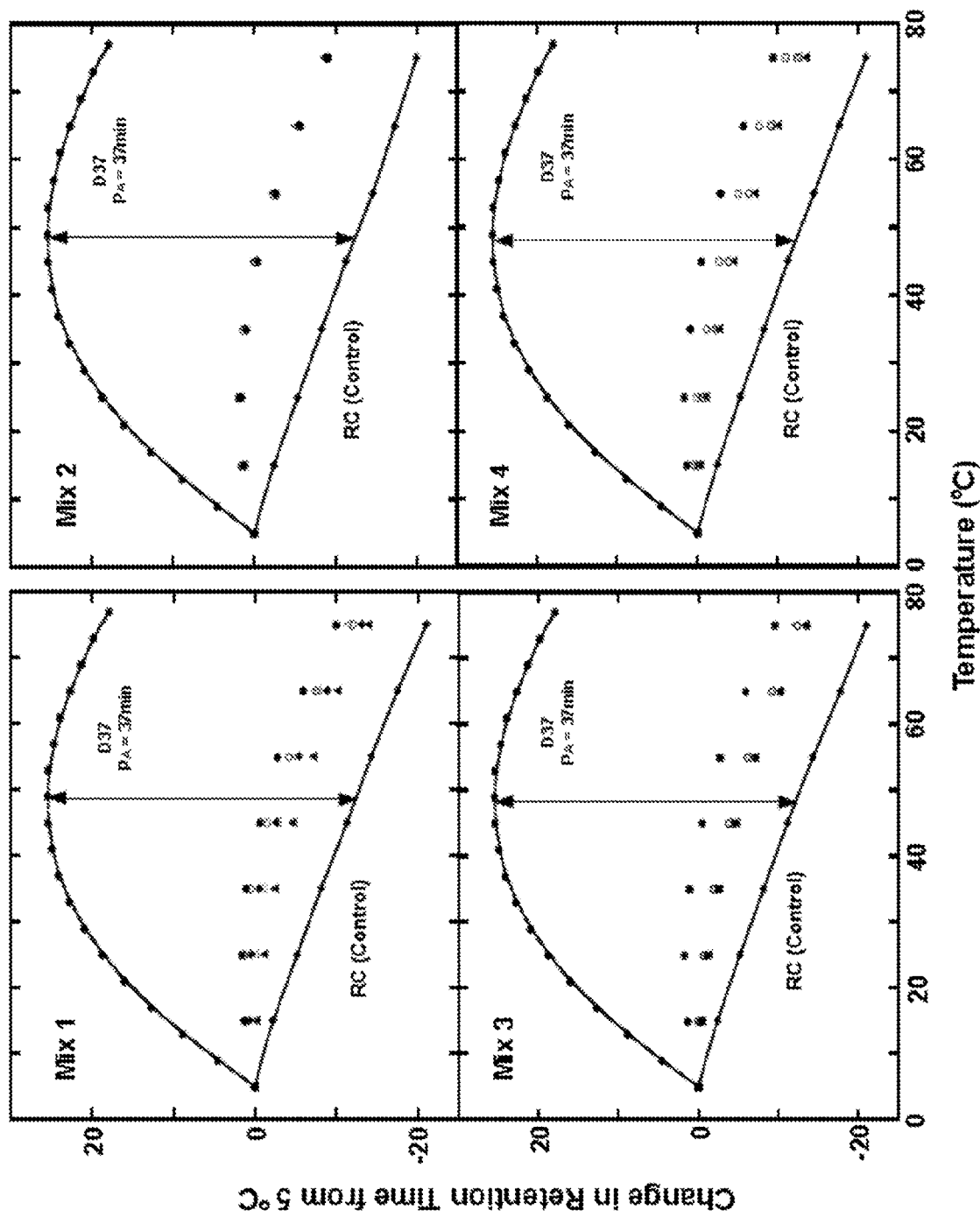
FIG. 7 shows the self-association of four mixes of α-helical peptides as determined by temperature profiling in reversed-phase HPLC (RP-HPLC). Mix 1 contained peptides D84 (6 Lys-1), D85 (6 Orn-1), D86 (6 Dbu-1), D87 (6 Arg-1), D105 (6 Dpr-1). Mix 2 contained peptides D84 (6 Lys-1), D88 (6 Lys-2), D101 (5 Lys-1), D103 (5 Lys-2). Mix 3 contained peptides D84 (6 Lys-1), D86 (6 Dbu-1), D89 (6 Dbu-2), D102 (5 Dbu-1), D104 (5 Dbu-2). Mix 4 contained peptides D84 (6 Lys-1), D86 (6 Dbu-1), D89 (6 Dbu-2), D105 (6 Dpr-1), D106 (6 Dpr-2). Peptide D37 represents a "control" AMP which contains no Lys residues ("specificity determinants") in its non-polar face.

FIG. 7 shows the self-association of the a-helical peptides determined by temperature profiling in reversed-phase HPLC (RP-HPLC). This figure summarizes the retention behavior from RP-HPLC of de novo designed amphipathic α-helical antimicrobial peptides (AMPs), with substitutions in the polar face of the peptides and with specificity determinants in the center of the non-polar face (positions 13 and 16), after normalization to their retention times at 5° C. The relative hydrophilicity/hydrophobicity of the tested AMPs is shown in Table 3.

TABLE 3

Relative Hydrophilicity/Hydrophobicity of AMPs

| Peptides[a] | Substitutions in Polar Face[b] | $t_R$ (min)[c] |
|---|---|---|
| +9 Peptides | | |
| D87 | 6 Arg-1 | 73.9 |
| D84 | 6 Lys-1 | 71.4 |
| D85 | 6 Orn-1 | 69.3 |
| D86 | 6 Dbu-1 | 58.8 |
| D105 | 6 Dpr-1 | 65.6 |
| D88 | 6 Lys-2 | 70.7 |
| D89 | 6 Dbu-2 | 60.2 |
| D106 | 6 Dpr-2 | 67.0 |
| +8 Peptides | | |
| D101 | 5 Lys-1 | 72.2 |
| D102 | 5 Dbu-1 | 57.7 |
| D103 | 5 Lys-2 | 71.1 |
| D104 | 5 Dbu-2 | 59.2 |

[a]Peptide sequences shown in FIGS. 3 and 4.
[b]The terms -1 and -2 represent different locations of the positively charged residues on the polar face.
[c]Linear AB gradient (0.5% B/min from 2% B) on a Zorbax SB-C8 RP-HPLC column at a flow-rate of 0.3 ml/min and a temperature of 30° C., where eluent A is 0.2% aq. TFA and eluent B is 0.18% TFA in acetonitrile.

Table 3 shows the relative overall hydrophilicity/hydrophobicity values of the AMPS as expressed by RP-HPLC retention times. From Table 3, there is a general decrease in retention time on replacing Arg with Lys and then decreasing the number of carbons in the side-chain as Lys (4 carbons) is substituted with Orn (3 carbons) and Dpr (1 carbon). Dbu (2 carbons) is an interesting outlier to this trend, with the Dbu-substituted peptides consistently showing lower RP-HPLC retention times (that is, lower overall expressed hydrophobicity) than the corresponding Dpr analogs. Such findings suggest that overall peptide hydrophobicity is not dependent on the amino acid composition alone but stability of the peptide helical conformation also plays a role, with the Dbu analogs appearing to somewhat disrupt peptide conformation (and hence disrupt the consistency of the non-polar face) relative to the other analogs.

Four mixtures were made and the number and type of substitutions in the polar face are shown in parentheses. Six polar face substitutions were made at positions 3, 7, 11, 18, 22, and 26 (denoted "–1") or 3, 7, 14, 15, 22, and 26 (denoted "–2"); Five polar face substitutions were made at positions 3, 7, 11, 18, and 22 (denoted –1) or 3, 7, 14, 15 and 22 (denoted –2).

Mix 1 was peptides D84 (6 Lys-1), D85 (6 Orn-1), D86 (6 Dbu-1), D87 (6 Arg-1), and D105 (6 Dpr-1).

Mix 2 was peptides D84 (6 Lys-1), D88 (6 Lys-2), D101 (5 Lys-1), and D103 (5 Lys-2).

Mix 3 was peptides D84 (6 Lys-1), D86 (6 Dbu-1), D89 (6 Dbu-2), D102 (5 Dbu-1), and D104 (5 Dbu-2).

Mix 4 was peptides D84 (6 Lys-1), D86 (6 Dbu-1), D89 (6 Dbu-2), D105 (6 Dpr-1), and D106 (6 Dpr-2).

D37 represents a "control" AMP which contains no specificity determinants in its non-polar face. See FIGS. 2, 3A-3C, and 4A-4C for the helical wheel and helical net representations of the peptides. RC is a random coil peptide used for RP-HPLC temperature profiling (SEQ ID NO:16: Ac-ELEKGGLEGEKGGKELEK-amide). Column: Zorbax SB300-C8 (150 mm×2.1 mm I.D.). Conditions: Linear AB gradient (0.25% B/min from 10% B) at a flow-rate of 0.3 ml/min, where eluent A is 0.2% aq. trifluoroacetic acid (TFA) and eluent B is 0.18% TFA in acetonitrile. The peptide self-association parameter, $P_A$, represents the maximum change in peptide retention relative to the random coil control peptide (RC), and is denoted by the double headed arrow for D37. Note the higher the $P_A$ value, the greater the peptide self-association. $P_A$ values for all peptides tested are shown in Table 4. From FIG. 7, the self-association parameter $P_A$ represents the degree of self-association of a peptide, i.e., the higher this value, the stronger the association of peptide molecules. The purpose of the current project was to decrease the degree of self-association of the AMPs and this has clearly been achieved when the $P_A$ values of the current AMPs with two Lys specificity determinants in the non-polar face (ranging from no self-association to a maximum value of just 7.2 min) are compared to peptide D37 with no Lys residues in its non-polar face (a value of 37 min) (FIG. 7 and Table 4).

TABLE 4

Temperature profiling data of AMPs.

| Peptides[a] | Substitution in Polar Face[b] | $T_p^c$ (° C.) | $P_A^d$ (min) |
|---|---|---|---|
| Mix 1 | | | |
| D84 | 6 Lys-1 | 25 | 6.8 |
| D85 | 6 Orn-1 | 15 | 2.9 |
| D86 | 6 Dbu-1 | NA[e] | NA |
| D105 | 6 Dpr-1 | 15 | 2.8 |
| D87 | 6 Arg-1 | 15 | 3.4 |
| Mix 2 | | | |
| D84 | 6 Lys-1 | 25 | 6.8 |
| D88 | 6 Lys-2 | 25 | 6.9 |
| D101 | 5 Lys-1 | 25 | 7.2 |
| D103 | 5 Lys-2 | 25 | 7.2 |
| Mix 3 | | | |
| D84 | 6 Lys-1 | 25 | 6.8 |
| D86 | 6 Dbu-1 | NA | NA |
| D89 | 6 Dbu-2 | NA | NA |
| D102 | 5 Dbu-1 | NA | NA |
| D104 | 5 Dbu-2 | NA | NA |
| Mix 4 | | | |
| D84 | 6 Lys-1 | 25 | 6.8 |
| D86 | 6 Dbu-1 | NA | NA |
| D89 | 6 Dbu-2 | NA | NA |
| D105 | 6 Dpr-1 | 15 | 2.8 |
| D106 | 6 Dpr-2 | 15 | 2.5 |
| D37[f] | 6 Lys | 53 | 37.0 |

[a]Peptide sequences shown in Tables 1A-1C.
[b]The terms -1 and -2 represent different locations of the positively charged residues on the polar face.
[c]$T_p$, temperature at which maximum retention time is observed during temperature profiling.
[d]Self-association parameter (described in FIG. 5).
[e]NA, denotes "No Association", i.e., peptide was not observed to show any increase in retention time with increasing temperature.
[f]D37 represents a "control" AMP with no lysine "specificity determinants" in its non-polar face.

Example 5

Antibacterial Activity

Gram-Negative Bacterial Strains used in this Study: All the *A. baumannii* strains used in this study were 1) obtained from the collection of Dr. Anthony A. Campagnari at the University of Buffalo and originally isolated from different patients and organs/tissues (strain 649, blood; strain 689, groin; strain 759, gluteus; strain 884, axilla; strain 985, pleural fluid); 2) were purchased from the American Type Culture Collection (ATCC, Manassas, Va., USA) (strain ATCC 17978, fatal meningitis; and strain ATCC 19606, urine); 3) obtained from MERCK (M89941, M89949, M89951, M89952, M89953, M89955 and M89963). These seven *A. baumannii* strains were resistant to polymyxin B and polymyxin E (Colistin).

Gram Positive Bacterial Strains used in this study: All the *S. aureus* strains used in this study were 1) nine methicillin-sensitive *S. aureus* strains; M22315, M22274 (Spine), M22300 (Finger), M22287 (Hip), M22312 (Finger), M22075 (Axilla), M21913 (Finger), BL7429 (Blood) and M22097 (Neck) 2) eight Methicillin/Oxacillin-resistant *S. aureus* strains; M22424 (arm), M22111 (ear), M22360 (labia), M22354, M21756 (nose), M22130, M22224 (leg), M21742 (nose).

Measurement of Antimicrobial Activity (MIC): The minimal inhibitory concentration (MIC) is defined as the lowest peptide concentration that inhibited bacterial growth. MICs were measured by a standard microtiter dilution method in Mueller Hinton (MH) medium. Briefly, cells were grown overnight at 37° C. in MH broth and were diluted in the same medium. Serial dilutions of the peptides were added to the microtiter plates in a volume of 50 μL, followed by the addition of 50 μL of bacteria to give a final inoculum of $5\times10^5$ colony-forming units (CFU)/mL. The plates were incubated at 37° C. for 24 h, and the MICs were determined.

Table 5 shows a summary of the antibacterial activities against 14 different strains of *A. baumannii*, 7 clinical isolates from different sources and 7 different strains resistant to polymyxin B and polymyxin E (Colistin) (antibiotics of last resort).

TABLE 5

Summary of antimicrobial activity against *A. baumannii*, *P. aeruginosa* and *S. aureus*

| Peptide Name | $MIC_{GM}(\mu M)^a$ | | | | |
|---|---|---|---|---|---|
| | *A. baumannii* (7 clinical isolates) | *A. baumannii* (7 resistant strains) | *P. aeruginosa* (6 clinical isolates) | *S. aureus* (8 MRSA) | *S. aureus* (9 MSSA) |
| Without specificity determinants | | | | | |
| D37 | 3.5 | 3.2 | 9.2 | — | — |
| D38 | 1.2 | 1.2 | 36.8 | 12.3 | 10.7 |
| D39 | 1.5 | 1.5 | 5.8 | 5.2 | 5.8 |
| D40 | 2.6 | 3.5 | 5.2 | 8.4 | 8.5 |
| Average | 2.2 | 2.4 | 14.3 | 8.6 | 8.3 |
| With specificity determinants | | | | | |
| D33 | 0.1 | 0.3 | 1.8 | 10.8 | 19.0 |
| D34 | 0.3 | 0.4 | 1.6 | 19.2 | 35.1 |
| D35 | 0.4 | 0.4 | 0.9 | 14.0 | 28.0 |
| D36 | 0.4 | 0.4 | 1.2 | 4.4 | 8.8 |
| Average | 0.3 | 0.38 | 1.4 | 12.1 | 22.7 |

[a]MICGM is the geometric mean of the MIC values (MIC is minimal inhibitory concentration (μM) that inhibited growth of different strains in Mueller-Hinton (MH) medium at 37oC after 24 h. MEC is given based on three sets of determinations) from 7 different clinical isolates of *A. baumannii*, 7 different strains of *A. baumannii* resistant to Polymyxin B and Colistin, antibiotics of last resort, 6 different clinical isolates of *P. aeruginosa*, 8 different methicillin-resistant *S. aureus* (MRSA) strains and 9 different methicillin-sensitive *S. aureus* (MSSA) strains. The detailed MIC values of individual strains are shown in Tables 6-8.

The average of the four $MIC_{GM}$-values (GM, geometric mean) for peptides D37 to D40, which did not have specificity determinants, was 2.2 microM. In contrast, the average of the four $MIC_{GM}$-values for peptides D33 to D36 with the two specificity determinants was 0.3 microM. Similarly, the average of four $MIC_{GM}$-values for peptides D37 to D40 (no specificity determinants) for the *A. baumannii* resistant strains to polymyxin B and polymyxin E (Colistin) was 2.4 microM. In contrast, the average of the $MIC_{GM}$-values for peptides D33 to D36 with the two specificity determinants was 0.38 microM. These results show an approximate 7-fold increase in antimicrobial activity of the peptides with specificity determinants against these 14 different *A. baumannii* isolates compared to peptides lacking the specificity determinants. In comparing peptides that have identical polar faces, with and without specificity determinants, the fold increase in antimicrobial activity for the seven clinical isolates of *A. baumannii* and seven resistant strains of *A. baumannii* is as follows: D37/D33 (35-fold and 10-fold); D38/D34 (4-fold and 3-fold); D39/D35 (3.8-fold and 3.8-fold); D40/D36 (6.5-fold and 8.8-fold). These results clearly show the enhancement of antimicrobial activity by incorporating the two specificity determinants into these AMPs. Clearly, AMP D33 shows the greatest improvement in antimicrobial activity with specificity determinants of 35-fold for the 7 clinical isolates from diverse *A. baumannii* clinical isolates and 10-fold for the 7 polymyxin B and polymyxin E (Colistin) resistant strains. In the case of *P. aeruginosa* strains (Table 5), the antimicrobial activity ($MIC_{GM}$ values) varied from 5.2 microM for D40 to 36.8 microM for D38. In comparing peptides that have identical polar faces with and without specificity determinants, the increase in antimicrobial activity ($MIC_{GM}$) was as follows: D37/D33 (5.1-fold); D38/D34 (23-fold); D39/D35 (6.4-fold) and D40/D36 (4.3-fold). Clearly AMP D34 shows the greatest improvement (23-fold) in antimicrobial activity with specificity determinants against *P. aeruginosa* (Table 5). Specificity determinants can make significant improvements in antimicrobial activity with the best peptides showing improvement in the $MIC_{GM}$-values of 35-fold against *A. baumannii* strains and 23-fold against *P. aeruginosa* strains. The inventors also screened the AMPs with and without specificity determinants against 17 *S. aureus* strains, 9 methicillin-sensitive strains and 8 methicillin-resistant strains (Table 5). The results show that specificity determinants have no advantage in improving antimicrobial activity against Gram-positive organisms represented by *S. aureus*. In fact, the $MIC_{GM}$-values with specificity determinants are clearly higher than without specificity determinants. For example, if the inventors compare peptides with identical polar faces, D38 and D34, there is a loss of antimicrobial activity from a $MIC_{GM}$-value of 10.7 microM to 35.1 microM; D39 and D35 there is a loss of activity from 5.8 microM to 28 microM among the MSSA strains. Similarly, for the MRSA strains, with D38 and D34, there is a loss of activity from a $MIC_{GM}$-value of 12.3 microM to 19.2 microM; for D39 and D35, there is a loss of activity from 5.2 microM to 14 microM. In general, there is a loss of antimicrobial activity when adding specificity determinants for activity against Gram-positive pathogens which is an advantage when designing Gram-negative selective AMPs. In addition, the activity against Gram-positive organisms represented by *S. aureus* strains is poor with and without specificity determinants (Table 5). The detailed results of all individual strains for *A. baumannii*, *P. aeruginosa* and *S. aureus* are shown in Tables 6A-6D; 7A and 7B; and 8A-8D, respectively.

TABLE 6A

Antimicrobial activity of peptide analogs against *A. baumannii* clinical isolates

| Peptide | ATCC 17978 Fatal Meningitis | ATCC 19606 Urine | 649 Blood | 689 Groin | 759 Gluteus | 884 Axilla | 985 Pleural fluid | MIC$_{GM}$ (μM)[b] |
|---|---|---|---|---|---|---|---|---|
| | | | | MIC(μM)[a] | | | | |
| *Without specificity determinants* | | | | | | | | |
| D37 | 2.9 | 5.8 | 2.9 | 2.9 | 5.8 | 2.9 | 2.9 | 3.5 |
| D38 | 1.4 | 1.4 | 0.7 | 0.7 | 2.9 | 0.7 | 1.4 | 1.2 |
| D39 | 2.9 | 2.9 | 1.4 | 1.4 | 1.4 | 0.7 | 0.7 | 1.5 |
| D40 | 5.8 | 2.9 | 2.9 | 2.9 | 2.9 | 1.4 | 1.4 | 2.6 |
| | | | | | | | Average | 2.2 |
| *With specificity determinants* | | | | | | | | |
| D33 | 0.1 | 0.2 | 0.1 | 0.1 | 0.2 | 0.1 | 0.2 | 0.1 |
| D34 | 0.2 | 0.4 | 0.2 | 0.2 | 0.4 | 0.4 | 0.4 | 0.3 |
| D35 | 0.4 | 0.4 | 0.4 | 0.4 | 0.4 | 0.4 | 0.4 | 0.4 |
| D36 | 0.4 | 0.4 | 0.4 | 0.4 | 0.4 | 0.4 | 0.4 | 0.4 |
| | | | | | | | Average | 0.3 |

[a] MIC is minimal inhibitory concentration (μM) that inhibited growth of different strains in Mueller-Hinton (MH) medium at 37° C. after 24 h. MIC is given based on three sets of determinations.
[b] MICGM is the geometric mean of the MIC values from 7 different clinical isolates of *Acinetobacter baumannii* and 7 different strains of *A. baumannii* resistant to Polymyxin B and Colistin, antibiotics of last resort.

TABLE 6B

Antimicrobial activity of peptide analogs against *A. baumannii* clinical isoates

| Peptide | ATCC 17978 Fatal Meningitis | ATCC 19606 Urine | 649 Blood | 689 Groin | 759 Gluteus | 884 Axilla | 985 Pleural fluid | MIC$_{GM}$ (μM)[b] | HC$_{50}$ (μM)[c] | TI[d] |
|---|---|---|---|---|---|---|---|---|---|---|
| | | | | MIC(μM)[a] | | | | | | |
| D41(Lys13/Lys16) | 0.7 | 0.7 | 0.4 | 0.4 | 0.4 | 0.4 | 0.4 | 0.4 | 13.7 | 34.3 |
| D41(Orn13/Orn16) | 1.4 | 1.4 | 1.4 | 0.4 | 0.4 | 0.7 | 0.7 | 0.8 | 34.0 | 42.5 |
| D41(Dbu13/Dbu16) | 0.7 | 0.7 | 0.7 | 0.7 | 0.7 | 0.4 | 0.7 | 0.6 | 24.3 | 40.5 |
| D41(Dpr13/Dpr16) | 0.7 | 0.3 | 0.7 | 0.7 | 0.7 | 0.7 | 0.7 | 0.6 | 22.6 | 37.7 |
| D41(Arg13/Arg16) | 1.3 | 0.3 | 0.7 | 0.3 | 0.7 | 0.7 | 0.7 | 0.6 | 7.2 | 12.0 |

[a] MIC is minimal inhibitory concentration (μM) that inhibited growth of different strains in Mueller-Hinton (MH) medium at 37° C. after 24 hours. MIC is given based on three sets of determinations.
[b] MIC$_{GM}$ is the geometric mean of the MIC values from 6 different clinical isolates of *P. aeruginosa*, 7 strains of *A. baumannii* resistant to Polymyxin B and Colistin, antibiotics of last resort and 7 different clinical isolates of *Acinetobacter baumanii*.
[c] HC$_{50}$ is the concentration if peptide that results in 50% hemolysis of human red blood cells after 18 hours at 37° C.
[d] T.I. is the therapeutic index the ratio of HC$_{50}$ value (μM) over the geometric mean MIC value (μM).
Large values indicate greater antimicrobial specificity compared to human red blood cells.

TABLE 6C

Antimicrobial activity of peptide analogs against *A. baumannii* strains resistant to Polymyxin B and Colistin

| Peptide | M89941 | M89949 | M89951 | M89952 | M89953 | M89955 | M89963 | MIC$_{GM}$ (μM)[b] |
|---|---|---|---|---|---|---|---|---|
| | | | | MIC(μM)[a] | | | | |
| *Without specificity determinants* | | | | | | | | |
| D37 | 2.9 | 2.9 | 2.9 | 2.9 | 2.9 | 2.9 | 5.8 | 3.2 |
| D38 | 1.4 | 1.4 | 1.4 | 1.4 | 0.7 | 0.4 | 2.9 | 1.2 |

TABLE 6C-continued

Antimicrobial activity of peptide analogs against *A. baumannii* strains resistant to Polymyxin B and Colistin

| Peptide | M89941 | M89949 | M89951 | M89952 MIC(μM)[a] | M89953 | M89955 | M89963 | MIC$_{GM}$ (μM)[b] |
|---|---|---|---|---|---|---|---|---|
| D39 | 2.9 | 1.4 | 0.7 | 2.9 | 1.4 | 0.7 | 1.4 | 1.5 |
| D40 | 5.8 | 5.8 | 2.9 | 2.9 | 2.9 | 2.9 | 2.9 | 3.5 |
| | | | | | | | Average | 2.35 |
| With specificity determinants | | | | | | | | |
| D33 | 0.2 | 0.2 | 0.2 | 0.7 | 0.4 | 0.4 | 0.2 | 0.3 |
| D34 | 0.4 | 0.4 | 0.4 | 0.4 | 0.4 | 0.4 | 0.4 | 0.4 |
| D35 | 0.4 | 0.4 | 0.4 | 0.7 | 0.4 | 0.4 | 0.4 | 0.4 |
| D36 | 0.4 | 0.4 | 0.4 | 0.7 | 0.4 | 0.4 | 0.4 | 0.4 |
| | | | | | | | Average | 0.38 |
| Colistin | >28 | >28 | >28 | >28 | >28 | >28 | >28 | >28 |
| PolymyxinB | >25 | >25 | >25 | >25 | >25 | >25 | >25 | >25 |

[a]MIC is minimal inhibitory concentration (μM) that inhibited growth of different strains in Mueller-Hinton (MH) medium at 37° C. after 24 h. MIC is given based on three sets of determinations.
[b]MIC$_{GM}$ is the geometric mean of the MIC values from 7 different clinical isolates of *Acinetobacter baumannii* and 7 different strains of *A. baumannii* resistant to Polymyxin B and Colistin, antibiotics of last resort.

TABLE 6D

Antimicrobial activity of peptide analogs against *A. baumannii* strains resistant to Polymyxin B and Colistin

| Peptide | M89941 | M89949 | M89951 | M89952 MIC(μM)[a] | M89953 | M89955 | M89963 | MIC$_{GM}$ (μM)[b] | HC$_{50}$ (μM)[c] | TI[d] |
|---|---|---|---|---|---|---|---|---|---|---|
| D41(Lys13/Lys16) | 0.7 | 0.7 | 0.7 | 0.4 | 0.4 | 0.2 | 0.4 | 0.4 | 13.7 | 34.3 |
| D41(Orn13/Orn16) | 0.7 | 0.7 | 0.7 | 0.4 | 0.7 | 0.4 | 0.7 | 0.6 | 34.0 | 56.7 |
| D41(Dbu13/Dbu16) | 0.7 | 0.7 | 0.7 | 0.4 | 0.4 | 0.4 | 0.7 | 0.5 | 24.3 | 48.6 |
| D41(Dpr13/Dpr16) | 0.7 | 0.7 | 0.7 | 0.7 | 0.7 | 0.7 | 0.7 | 0.7 | 22.6 | 32.3 |
| D41(Arg13/Arg16) | 1.3 | 0.7 | 0.7 | 0.7 | 0.7 | 0.7 | 0.7 | 0.8 | 7.2 | 9.0 |
| Colistin | >28 | >28 | >28 | >28 | >28 | >28 | >28 | >28 | | |
| Polymyxin B | >25 | >25 | >25 | >25 | >25 | >25 | >25 | >25 | | |

[a]MIC is minimal inhibitory concentration (μM) that inhibited growth of different strains in Mueller-Hinton (MH) medium at 37° C. after 24 hours. MIC is given based on three sets of determinations.
[b]MIC$_{GM}$ is the geometric mean of the MIC values from 6 different clinical isolates of *P. aeruginosa*, 7 strains of *A. baumannii* resistant to Polymyxin B and Colistin, antibiotics of last resort and 7 different clinical isolates of *Acinetobacter baumanii*.
[c]HC$_{50}$ is the concentration if peptide that results in 50% hemolysis of human red blood cells after 18 hours at 37° C.
[d]T.I. is the therapeutic index the ratio of HC$_{50}$ value (μM) over the geometric mean MIC value (μM).
Large values indicate greater antimicrobial specificity compared to human red blood cells.

TABLE 7A

Antimicrobial activity of peptide analogs against clinical isolates of *Pseudomonas aeruginosa*

| Peptide | PAO1 | PAK | PA14 | CP204 MIC(μM)[a] Strain | M2 | WR5 | MIC$_{GM}$ (μM)[b] |
|---|---|---|---|---|---|---|---|
| Without specificity determinants | | | | | | | |
| D37 | 11.6 | 5.8 | 5.8 | 11.6 | 11.6 | 11.6 | 9.2 |
| D38 | 23.2 | 11.6 | 2.9 | >185.6 | 92.8 | 92.8 | 36.8 |
| D39 | 5.8 | 2.9 | 2.9 | 23.2 | 5.8 | 5.8 | 5.8 |
| D40 | 5.8 | 2.9 | 2.9 | 11.6 | 5.8 | 5.8 | 5.2 |
| With specificity determinants | | | | | | | |
| D33 | 1.4 | 1.4 | 0.7 | 2.8 | 2.8 | 2.8 | 1.8 |
| D34 | 1.4 | 1.4 | 0.7 | 2.8 | 2.8 | 1.4 | 1.6 |
| D35 | 0.7 | 1.4 | 0.4 | 1.4 | 1.4 | 0.7 | 0.9 |
| D36 | 1.4 | 1.4 | 0.7 | 1.4 | 1.4 | 1.4 | 1.2 |

[a]MIC is minimal inhibitory concentration (μM) that inhibited growth of different strains in Mueller-Hinton (MH) medium at 37° C. after 24 h. MIC is given based on three sets of determinations.
[b]MIC$_{GM}$ is the geometric mean of the MIC values from 6 different clinical isolates of *P. aeruginosa*.

TABLE 7B

Antimicrobial activity of peptide analogs against clinical isolates of Pseudomonas aeruginosa

| Peptide | MIC(μM)[a] Strain | | | | | | $MIC_{GM}$ (μM)[b] | $HC_{50}$[c] (μM) | T.I.[d] |
| --- | --- | --- | --- | --- | --- | --- | --- | --- | --- |
| | PAO1 | PAK | PA14 | CP204 | M2 | WR5 | | | |
| D41(Lys13/Lys16) | 0.7 | 0.7 | 0.7 | 1.4 | 0.7 | 0.7 | 0.8 | 13.7 | 17.1 |
| D41(Orn13/Orn16) | 1.2 | 1.2 | 0.6 | 0.6 | 1.2 | 1.2 | 1.0 | 34.0 | 34.0 |
| D41(Dbu13/Dbu16) | 0.7 | 1.4 | 0.7 | 0.7 | 0.7 | 0.7 | 0.8 | 24.3 | 30.4 |
| D41(Dpr13/Dpr16) | 1.3 | 1.3 | 1.3 | 1.3 | 1.3 | 1.3 | 1.3 | 22.6 | 17.4 |
| D41(Arg13/Arg16) | 1.3 | 0.6 | 1.3 | 1.3 | 1.3 | 1.3 | 1.1 | 7.2 | 6.5 |

[a]MIC is minimal inhibitory concentration (μM) that inhibited growth of different strains in Mueller-Hinton (MH) medium at 37° C. after 24 hours. MIC is given based on three sets of determinations.
[b]$MIC_{GM}$ is the geometric mean of the MIC values from 6 different clinical isolates of P. aeruginosa, 7 strains of A. baumannii resistant to Polymyxin B and Colistin, antibiotics of last resort and 7 different clinical isolates of Acinetobacter baumanii.
[c]$HC_{50}$ is the concentration if peptide that results in 50% hemolysis of human red blood cells after 18 hours at 37° C.
[d]T.I. is the therapeutic index the ratio of $HC_{50}$ value (μM) over the geometric mean MIC value (μM).
Large values indicate greater antimicrobial specificity compared to human red blood cells.

TABLE 8A

Antimicrobial activity of peptide analogs against Methicillin-resistant Staphylococcus aureus (MRSA) strains

| Peptide | Strain | | | | | | | | $MIC_{GM}$ (μM)[b] |
| --- | --- | --- | --- | --- | --- | --- | --- | --- | --- |
| | M22424 | M22111 | M22360 | M22354 | M21756 | M22130 | M22224 | M21742 | |
| | Source | | | | | | | | |
| | Arm | Ear | Labia | — | Nose | — | Leg | Nose | |
| | MIC(μM)[a] | | | | | | | | |
| Without specificity determinants | | | | | | | | | |
| D38 | 14.5 | 14.5 | 2.9 | 23.2 | 23.2 | 11.6 | 11.6 | 11.6 | 12.3 |
| D39 | 7.2 | 7.2 | 2.9 | 5.8 | 2.9 | 5.8 | 5.8 | 5.8 | 5.2 |
| D40 | 9.1 | 9.1 | 5.8 | 11.6 | 11.6 | 5.8 | 11.6 | 5.8 | 8.4 |
| With specificity determinants | | | | | | | | | |
| D33 | 13.9 | 13.9 | 1.4 | 22.3 | 11.1 | 11.1 | 22.3 | 11.1 | 10.8 |
| D34 | 34.8 | 17.4 | 1.4 | 44.5 | 22.3 | 22.3 | 44.5 | 22.3 | 19.2 |
| D35 | 13.9 | 27.8 | 0.7 | 44.5 | 22.3 | 22.3 | 22.3 | 11.1 | 14.0 |
| D36 | 4.3 | 4.3 | 1.4 | 5.6 | 5.6 | 5.6 | 5.6 | 5.6 | 4.4 |

TABLE 8B

Antimicrobial activity of peptide analogs against Methicillin-sensitive Staphylococcus aureus (MSSA) strains

| Peptide | Strain | | | | | | | | | $MIC_{GM}$ (μM)[b] |
| --- | --- | --- | --- | --- | --- | --- | --- | --- | --- | --- |
| | M22315 | M22274 | M22300 | M22287 | M22312 | M22075 | M21913 | BL7429 | M22097 | |
| | Source | | | | | | | | | |
| | — | Spine | Finger | Hip | Finger | Axilla | Finger | Blood | Neck | |
| | MIC(μM)[a] | | | | | | | | | |
| Without specificity determinants | | | | | | | | | | |
| D38 | 14.5 | 14.5 | 29.0 | 5.8 | 5.8 | 5.8 | 5.8 | 11.6 | 23.2 | 10.7 |
| D39 | 7.2 | 7.2 | 7.2 | 5.8 | 5.8 | 5.8 | 5.8 | 2.9 | 5.8 | 5.8 |
| D40 | 9.1 | 9.1 | 18.1 | 5.8 | 5.8 | 5.8 | 5.8 | 5.8 | 23.2 | 8.5 |
| With specificity determinants | | | | | | | | | | |
| D33 | 27.8 | 27.8 | 27.8 | 5.6 | 11.1 | 22.3 | 11.1 | 22.3 | 44.5 | 19.0 |
| D34 | 34.8 | 34.8 | 34.8 | 11.1 | 22.3 | 44.5 | 44.5 | 44.5 | 89.0 | 35.1 |

TABLE 8B-continued

Antimicrobial activity of peptide analogs against Methicillin-sensitive *Staphylococcus aureus* (MSSA) strains

| | Strain | | | | | | | | |
|---|---|---|---|---|---|---|---|---|---|
| | M22315 | M22274 | M22300 | M22287 | M22312 | M22075 | M21913 | BL7429 | M22097 |
| | | | | | Source | | | | |
| Peptide | — | Spine | Finger | Hip | Finger MIC(µM)$^a$ | Axilla | Finger | Blood | Neck | MIC$_{GM}$ (µM)$^b$ |
| D35 | 55.6 | 13.9 | 55.6 | 11.1 | 22.3 | 22.3 | 44.5 | 22.3 | 44.5 | 28.0 |
| D36 | 4.3 | 17.4 | 17.4 | 5.6 | 5.6 | 11.1 | 5.6 | 11.1 | 11.1 | 8.8 |

$^a$MIC is minimal inhibitory concentration (µM) that inhibited growth of different strains in Mueller-Hinton (MH) medium at 37° C. after 24 h. MIC is given based on three sets of determinations.
$^b$MIC$_{GM}$ is the geometric mean of the MIC values from 8 different MRSA strains and 9 different strains of MSSA.
c) R denotes resistant, S denotes sensitive.

TABLE 8C

Antimicrobial activity of peptide analogs against *Staphylococcus aureus* strains

| | MRSA | MSSA |
|---|---|---|
| Strain | M21742 | BL7429 |
| Source | Nose | Blood |
| Peptide | MIC(µM)$^a$ | |
| D41(Lys13/Lys16) | 5.5 | 11.0 |
| D41(Orn13/Orn16) | 11.1 | 11.1 |
| D41(Dbu13/Dbu16) | 5.6 | 11.2 |
| D41(Dpr13/Dpr16) | 5.2 | 5.2 |
| D41(Arg13/Arg16) | 5.4 | 5.4 |

TABLE 8D

Resistance profile of MRSA and MSSA strains

| | | MRSA | | | | | | | | MSSA |
|---|---|---|---|---|---|---|---|---|---|---|
| | | Name | | | | | | | | |
| | Source | M22424 Arm | M22111 Ear | M22360 Labia | M22354 — | M21756 Nose | M22130 — | M22224 Leg | M21742 Nose | M22315 — |
| Antibiotic Susceptibility | Oxacillin | R$^c$ | R | R | R | R | R | R | R | S |
| | Clindamycin | S$^c$ | R | S | S | S | S | S | S | S |
| | Erythromycin | R | R | R | R | S | R | R | R | S |
| | Trimethoprim/ sulfamethoxazole | S | S | S | S | S | S | S | S | S |

| | | MSSA | | | | | | | |
|---|---|---|---|---|---|---|---|---|---|
| | | Name | | | | | | | |
| | Source | M22274 Spine | M22300 Finger | M22287 Hip | M22312 Finger | M22075 Axilla | M21913 Finger | BL7429 Blood | M22097 Neck |
| Antibiotic Susceptibility | Oxacillin | S | S | S | S | S | S | S | S |
| | Clindamycin | S | S | S | S | S | S | S | S |
| | Erythromycin | S | S | — | S | S | S | S | S |
| | Trimethoprim/ sulfamethoxazole | S | S | S | S | S | S | S | S | a) MIC is minimal inhibitory concentration (µM) that inhibited growth of different strains in Mueller-Hinton (MH) medium at 37° C. after 24 h. MIC is given based on three sets of determinations.
b) MIC$_{GM}$ is the geometric mean of the MIC values from 8 different MRSA strains and 9 different strains of MSSA.
$^c$R denotes resistant, S denotes sensitive.

Example 6

Hemolytic Activity and Therapeutic Indices

Measurement of Hemolytic Activity: Peptide samples (concentrations determined by amino acid analysis) were added to 1% human erythrocytes in phosphate-buffered saline (100 mM NaCl, 80 mM Na$_2$HPO$_4$, 20 mM NaH$_2$PO$_4$, pH 7.4) and the reaction mixtures were incubated at 37° C. for 18 h in microtiter plates. Two-fold serial dilutions of the peptide samples were carried out. This determination was made by withdrawing aliquots from the hemolysis assays and removing unlysed erythrocytes by centrifugation (800× g). Hemoglobin release was determined spectrophotometrically at 570 nm. The control for 100% hemolysis was a sample of erythrocytes treated with water. The control for no release of hemoglobin was a sample of 1% erythrocytes without any peptide added. Since erythrocytes were in an isotonic medium, no detectable release (<1% of that released upon complete hemolysis) of hemoglobin was observed from this control during the assay. The hemolytic activity is generally determined as the peptide concentration that causes 50% hemolysis of erythrocytes after 18 h (HC$_{50}$). HC$_{50}$ was determined from a plot of percent lysis versus peptide concentration (µM). With the peptides used in this study 50% hemolysis could not be reached, thus the inventors used HC$_{30}$ values. Calculation of Therapeutic Index The therapeutic index is a widely-accepted parameter to represent the specificity of antimicrobial peptides for prokaryotic versus eukaryotic cells. It is calculated by the ratio of hemolytic activity and antimicrobial activity (MIC); thus, larger values of therapeutic index indicate greater specificity for prokaryotic cells. With the peptides used in this study the inventors used the $HC_{30}$/MIC ratio value to calculate the therapeutic index. The biological activities of the 20 peptide analogs in this study are shown in Tables 9A-9C.

TABLE 9A

Biological activity of peptide analogs with and without specificity determinants against *A. baumannii* strains resistant to polymyxin B and colistin

| Peptide Name | Antimicrobial activity $MIC_{GM}$ (μM)[a] | Hemolytic activity $HC_{30}$ (μM)[b] | Therapeutic index $HC_{30}/MIC_{GM}$[c] |
|---|---|---|---|
| With specificity determinants | | | |
| D33 | 0.3 | 89 | 297 |
| D34 | 0.4 | 126 | 315 |
| D35 | 0.4 | 30 | 75 |
| D36 | 0.4 | 61 | 153 |
| Average | 0.38 | 76.5 | 210 |
| Without specificity determinants | | | |
| D37 | 3.2 | 2.6 | 0.8 |
| D38 | 1.2 | 2.8 | 2.3 |
| D39 | 1.5 | 2.8 | 1.9 |
| D40 | 3.5 | 2.8 | 0.8 |
| Average | 2.35 | 2.75 | 1.45 |

Fold improvement for peptides with specificity determinants

| | Antimicrobial activity | | Therapeutic index |
|---|---|---|---|
| D37/D33 | 3.2/0.3 = 10.7 | D33/D37 | 297/0.8 = 371 |
| D38/D34 | 1.2/0.4 = 3.0 | D34/D38 | 315/2.3 = 137 |
| D39/D35 | 1.5/0.4 = 3.8 | D35/D39 | 75/1.9 = 39 |
| D40/D36 | 3.5/0.4 = 8.8 | D36/D40 | 153/0.8 = 191 |
| Average | 6.6 | Average | 185 |

[a] Antimicrobial activity (MIC) is the minimal inhibitory concentration of peptide that inhibits growth after 24 h at 37° C. $MIC_{GM}$ is the geometric mean of the MIC values from seven different *Acinetobacter baumannii* strains resistant to polymyxin B and colistin (Tables 5 and 6).
[b] $HC_{30}$ is the concentration of peptide that results in 30% hemolysis after 18 h at 37° C.
[c] Therapeutic index is the ratio of the $HC_{30}$ value (μM) over the geometric mean MIC value (μM). Large values indicate greater antimicrobial specificity compared to human red blood cells.

TABLE 9B

Hemolytic Activity expressed as $HC_{50}$, therapeutic index was calculated from $HC_{50}$ (μM)/$MIC_{GM}$ (μM)

| Peptide Name | Peptide Mass | $HC_{50}$(μg/mL) | $HC_{50}$(μM) | $MIC_{GM}$ (μM) | T.I. |
|---|---|---|---|---|---|
| D41Lys 13/16 | 2849.64 | 39 | 13.7 | 0.4 | 34.3 |
| D41Orn 13/16 | 2821.59 | 96 | 34.0 | 0.6 | 56.7 |
| D41Dbu 13/16 | 2793.54 | 68 | 24.3 | 0.5 | 48.6 |
| D41Dpr 13/16 | 2765.49 | 62.5 | 22.6 | 0.7 | 32.3 |
| D41Arg 13/16 | 2905.65 | 21 | 7.2 | 0.8 | 9.0 |
| D84 (6 Lys-1) | 2865.62 | 155.5 | 54.3 | 0.5 | 108.6 |
| D85 (6 Orn-1) | 2781.46 | 406.5 | 146.1 | 0.5 | 292.2 |
| D86 (6 Dbu-1) | 2697.30 | >2000 | >741.5 | 1.0 | >742 |
| D87 (6 Arg-1) | 3033.70 | 12 | 4.0 | ND | ND |
| D105 (6 Dpr-1) | 2613.14 | >3000 | >1148 | 1.2 | >957 |
| D88 (6 Lys-2) | 2865.62 | 231 | 80.6 | 0.4 | 201.5 |
| D89 (6 Dbu-2) | 2697.30 | >3000 | >1112.2 | 0.7 | >1589 |
| D106 (6 Dpr-2) | 2613.14 | 889 | 340.2 | 0.8 | 425.3 |
| D101 (5 Lys-1) | 2824.53 | 279 | >103.9 | ND | ND |
| D102 (5 Dbu-1) | 2684.26 | >2000 | >708 | ND | ND |
| D103 (5 Lys-2) | 2824.53 | 381 | 134.9 | ND | ND |
| D104 (5 Dbu-2) | 2684.26 | >4000 | >1490 | ND | ND |
| D86 (6 Dbu-1)-PEG1 | 3754.60 | 363 | 136.7 | 2.8 | 48.8 |
| D86 (6 Dbu-1)-PEG2 | 4882.90 | 297 | 111.9 | 2.6 | 43.0 |

$HC_{50}$ is the concentration of peptide that results in 50% hemolysis of human red blood cells after 18 hours at 37° C.
6 Lys-1 denotes 6 Lys residues on the polar face at positions 3, 7, 11, 18, 22, and 26.
6 Lys-2 denotes 6 Lys residues on the polar face at positions 3, 7, 14, 15, 22, and 26.
5 Lys-1 denotes 5 Lys residues on polar face at positions 3, 7, 11, 18, and 22.
5 Lys-2 denotes 5 Lys residues on polar face at positions 3, 7, 14, 15, and 22.
D86 (6 Dbu-1)-PEG1 denotes 6 Dbu residues on polar face of peptide attached to a PEG to give a total mass of 3754.6.
D86 (6 Dbu-1)-PEG2 denotes 6 Dbu residues on polar face of peptide attached to a PEG to give a total mass of 4882.9.
ND denotes antimicrobial activity not determined.

TABLE 9C

Antimicrobial Activity Against 7 Strains of *Acinetobacter baumannii* Resistant to Polymyxin B and Colistin, Hemolytic Activity Expressed as $HC_{50}$ and the Therapeutic Index (TI)

| Peptide | Molecular weight | MIC (μM) | | | | | | | $MIC_{GM}$ (μM) | $HC_{50}$ (μM) | T.I. |
| | | MB9941 | MB9949 | MB9951 | MB9952 | MB9953 | MB9955 | MB9963 | | | |
|---|---|---|---|---|---|---|---|---|---|---|---|
| D84 | 2865.62 | 0.3 | 0.7 | 0.3 | 0.7 | 0.7 | 0.3 | 0.7 | 0.5 | 54.3 | 108.6 |
| D85 | 2781.46 | 0.7 | 0.7 | 0.7 | 0.4 | 0.4 | 0.4 | 0.4 | 0.5 | 146.1 | 292.2 |
| D86 | 2697.30 | 0.7 | 0.7 | 1.4 | 0.7 | 1.4 | 0.7 | 1.4 | 1.0 | >741.5 | >741.5 |
| D105 | 2613.14 | 0.8 | 0.8 | 3.0 | 0.8 | 3.0 | 0.8 | 1.5 | 1.2 | >1148 | >956.7 |
| D88 | 2865.62 | 0.7 | 0.7 | 0.3 | 0.3 | 0.3 | 0.3 | 0.3 | 0.4 | 80.6 | 201.5 |
| D89 | 2697.30 | 0.7 | 0.7 | 0.7 | 0.7 | 0.7 | 0.7 | 0.7 | 0.7 | >1112.2 | >1588.9 |
| D106 | 2613.14 | 0.8 | 0.8 | 1.5 | 0.8 | 0.8 | 0.4 | 0.8 | 0.8 | 340.2 | 425.3 |
| D86PEG1 | 3754.56* | 1.1 | 2.1 | 4.1 | 4.1 | 8.3 | 1.1 | 4.1 | 2.8 | 136.7 | 48.8 |
| D86PEG2 | 4882.89** | 1.6 | 1.6 | 3.2 | 3.2 | 6.4 | 1.6 | 3.2 | 2.6 | 111.9 | 43.0 |

$MIC_{GM}$, the geometric mean MIC in micromolar where the MIC is the lowest peptide concentration that inhibited bacterial growth.
$HC_{50}$, peptide concentration that causes 50% hemolysis of human red blood cells after 18 hr.
T.I., the therapeutic index is the ratio of hemolytic and antimicrobial activity, $HC_{50}/MIC_{GM}$.
*,**The peptide pegylated was D86 with a free α-amino group (mass 2655.3).

The four peptides without specificity determinants are extremely hemolytic with $HC_{30}$ values (the peptide concentration required for 30% hemolysis) of 2.6 microM to 2.8 microM, which is comparable with the antimicrobial activity of 1.2 to 3.5 microM. Thus, the therapeutic indices vary from 0.8 to 2.3 (Table 9A). The specificity determinants enhance antimicrobial activity by 3-fold to 10.7-fold depending on the AMP (the average increase in antimicrobial activity for the 4 peptides D33 to D36 is 6.6-fold) (Table 9A). The specificity determinants result in dramatic decreases in hemolytic activities from an average of 2.75 microM for AMPs lacking specificity determinants to 30 to 126 microM depending on the AMP. This corresponds to increases in the therapeutic indices from 39-fold to 371-fold (an average improvement of 185-fold for the 4 peptides with specificity determinants (Table 9A). It is obvious that the improvements in the therapeutic indices depend on the location of the positively charged residues on the polar face, which varies between AMPs D33 to D36 (FIG. 1B). The specificity determinants (two positively charged Lys residues at positions K13 and K16) are in identical positions in AMPs D33 to D36 (FIG. 1C). The positions of the six positively charged residues are identical in each peptide pair D33 to D37, D34 to D38, D35 to D39 and D36 to D40 and the only difference is with and without specificity determinants. Consequently, it must be the location of the specificity determinants relative to the six positively charged residues on the polar face that results in large differences in therapeutic indices from 39-fold for pair D35 to D39 to 371-fold for peptide pair D33 to D37. In peptide pair D33 and D37 the 6 positively charged residues on the polar face are most distant in 3-dimensional space from the two lysine residues on the non-polar face (a 371-fold improvement in the therapeutic index) (FIG. 1C). When the six positively charged residues on the polar face are extremely close in 3-dimensional space to the specificity determinants on the non-polar face (D35) there is only a 39-fold improvement in the therapeutic index (FIG. 1B). This approximately 10-fold difference in therapeutic index between D33 and D35 (Table 9A) shows the importance of location of positively charged residues on the polar face relative to the specificity determinants on the non-polar face. These results clearly suggest the inventors can control the improvement in therapeutic index by de novo design.

In Table 6D the peptide denoted D41 (Lys 13/Lys 16) has lysine residues on the polar face at positions 3, 4, 7, 11, 18, 22, and 26. The total charge on this peptide is +9. Peptide D84 (Table 9C) has lysine residues on the polar face at positions 3, 7, 11, 18, 22, and 26. The lysine residue at position 4 in D41 was moved to Lys 1 in D84. This subtle change improved the therapeutic index from 34.3 for D41 (Lys 13/Lys 16) to a therapeutic index of 108.6 for D84. This 3.2-fold improvement in the therapeutic index suggested there is a significant advantage to having Lys at position 1. Thus, all peptides in Table 9B and Table 9C have Lys at position 1 to enhance the therapeutic index.

Figure 3A:
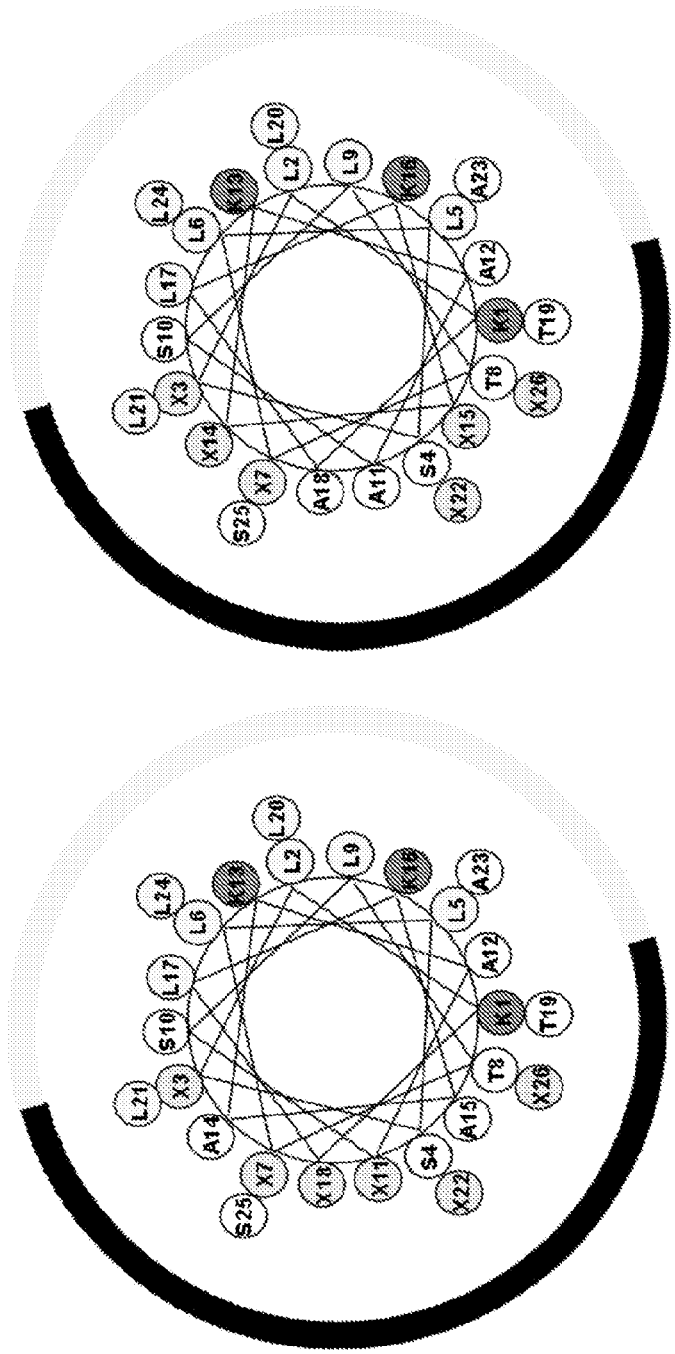
FIGS. 3A-3C similarly show helical wheel (FIG. 3A) and helical net (FIGS. 3B and 3C) representations of two helical AMPS with a net positive charge of +9 (D33 and D34) with or without specificity determinants on the non-polar face. In the helical wheels (FIG. 3A), the non-polar face is indicated as a light arc, and the polar face is indicated as a black arc. In the helical nets (FIGS. 3B and 3C), the residues on the polar face are boxed and the residues on the non-polar face are circled. The potential i to i+3, or i to i+4 electrostatic repulsions between positively charged residues are shown as black dotted lines. The i to i+3, or i to i+4 hydrophobic interactions between large hydrophobes are shown as solid black lines.
Figure 3B:
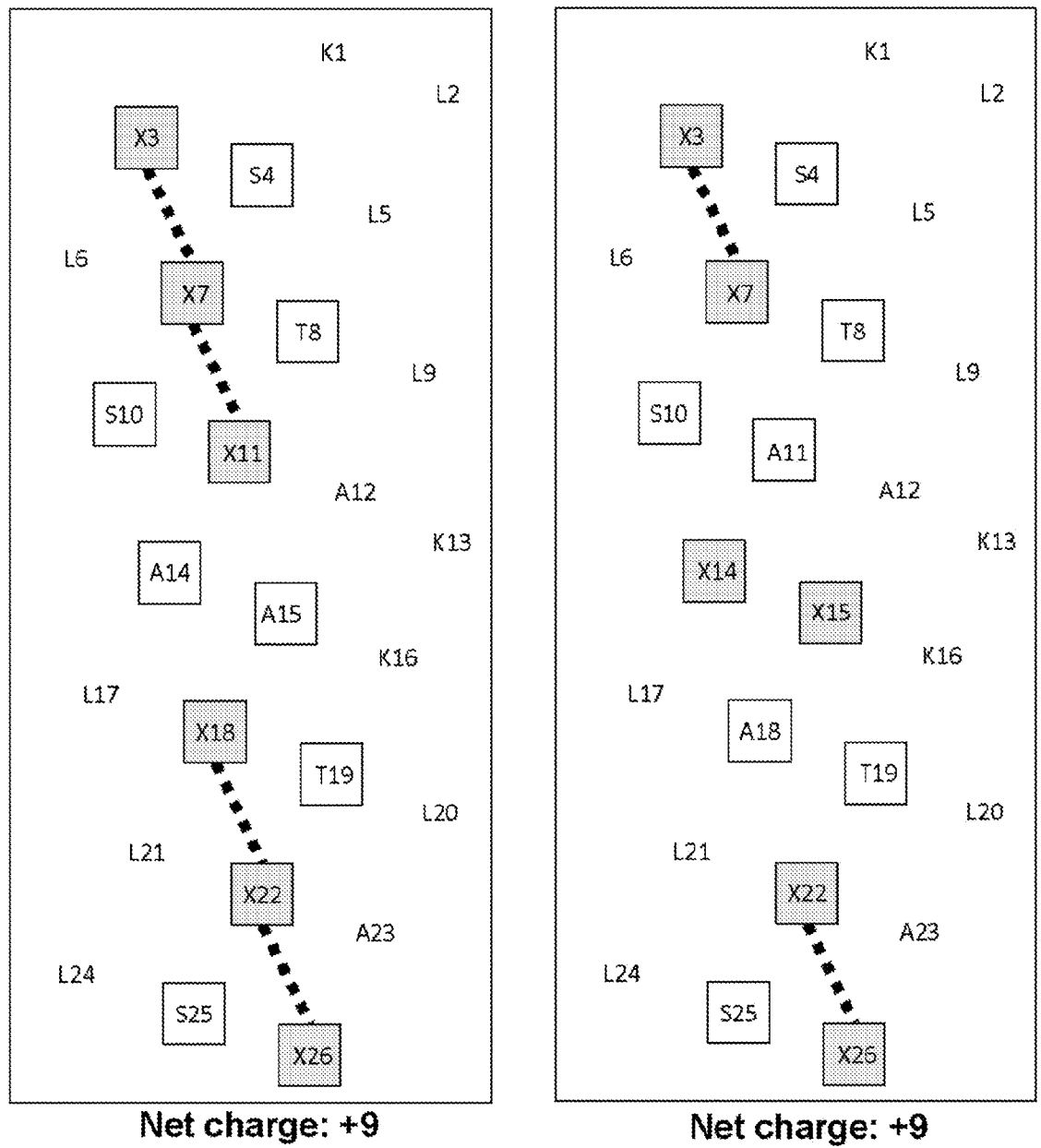
Figure 3C:
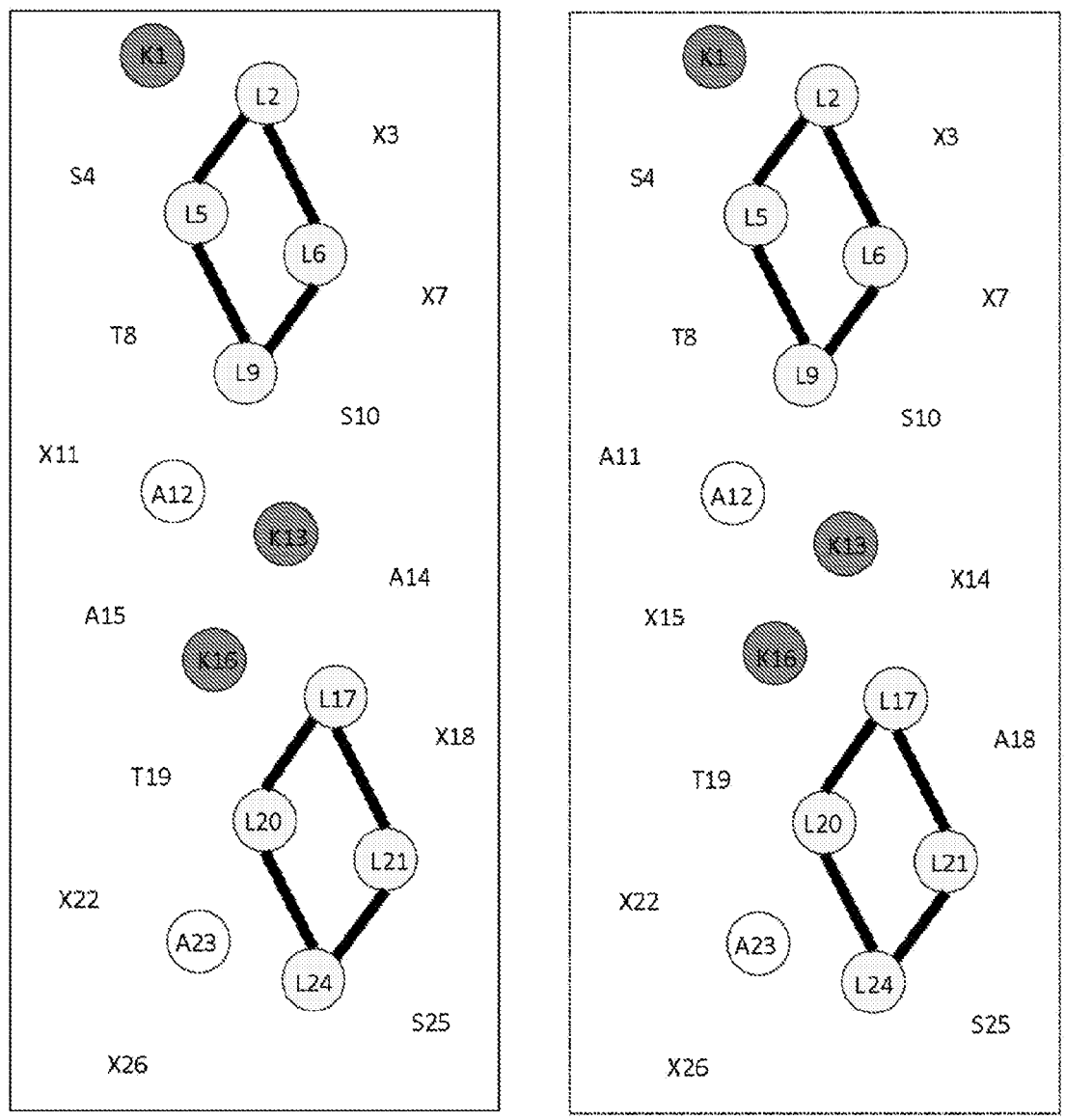
Figure 4A:
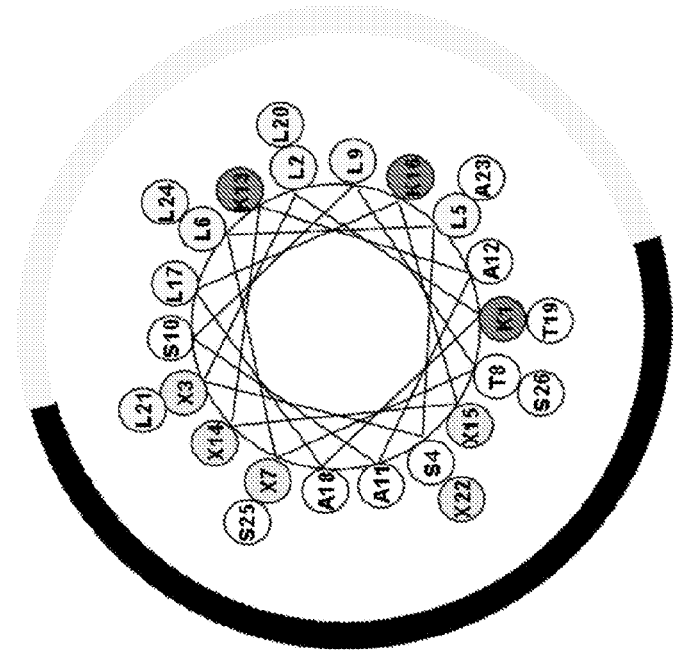
FIGS. 4A-4C similarly show helical wheel (FIG. 4A) and helical net (FIGS. 4B and 4C) representations of two helical AMPs with a net positive charge of +8 (D101 and D103) with or without specificity determinants on the non-polar face. In the helical wheels (FIG. 4A), the non-polar face is indicated as a light arc, and the polar face is indicated as a black arc. In the helical nets (FIGS. 4B and 4C), the residues on the polar face are boxed and the residues on the non-polar face are circled. The potential i to i+3, or i to i+4 electrostatic repulsions between positively charged residues are shown as black dotted lines. The i to i+3, or i to i+4 hydrophobic interactions between large hydrophobes are shown as solid black lines.
Figure 4A:
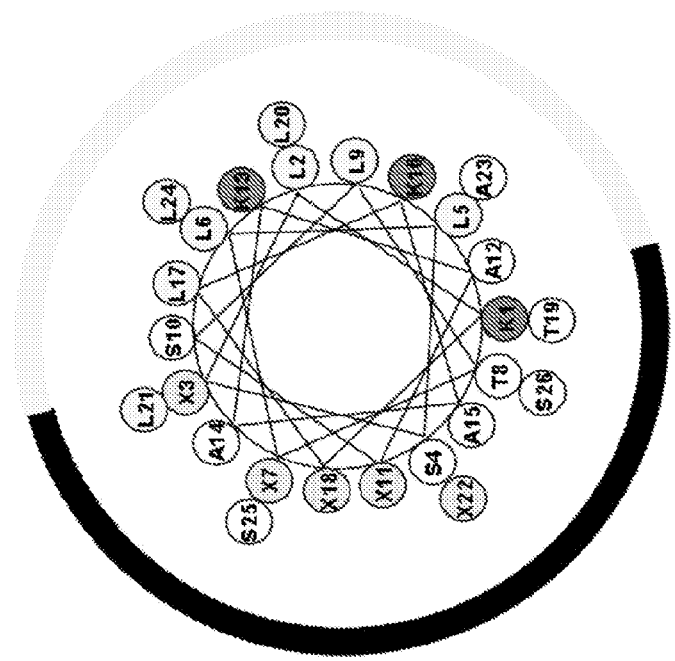
Figure 4B:
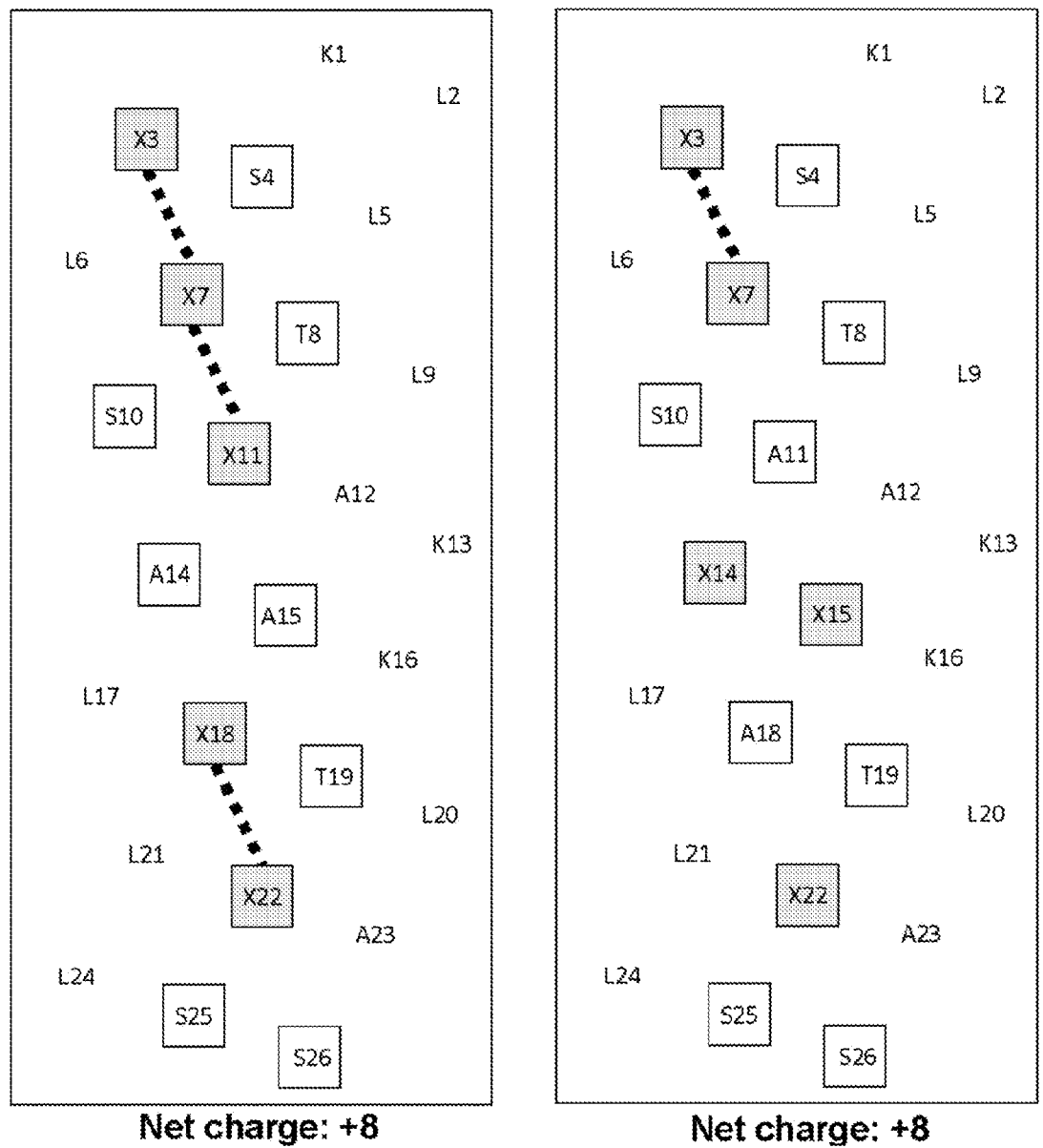
Figure 4C:
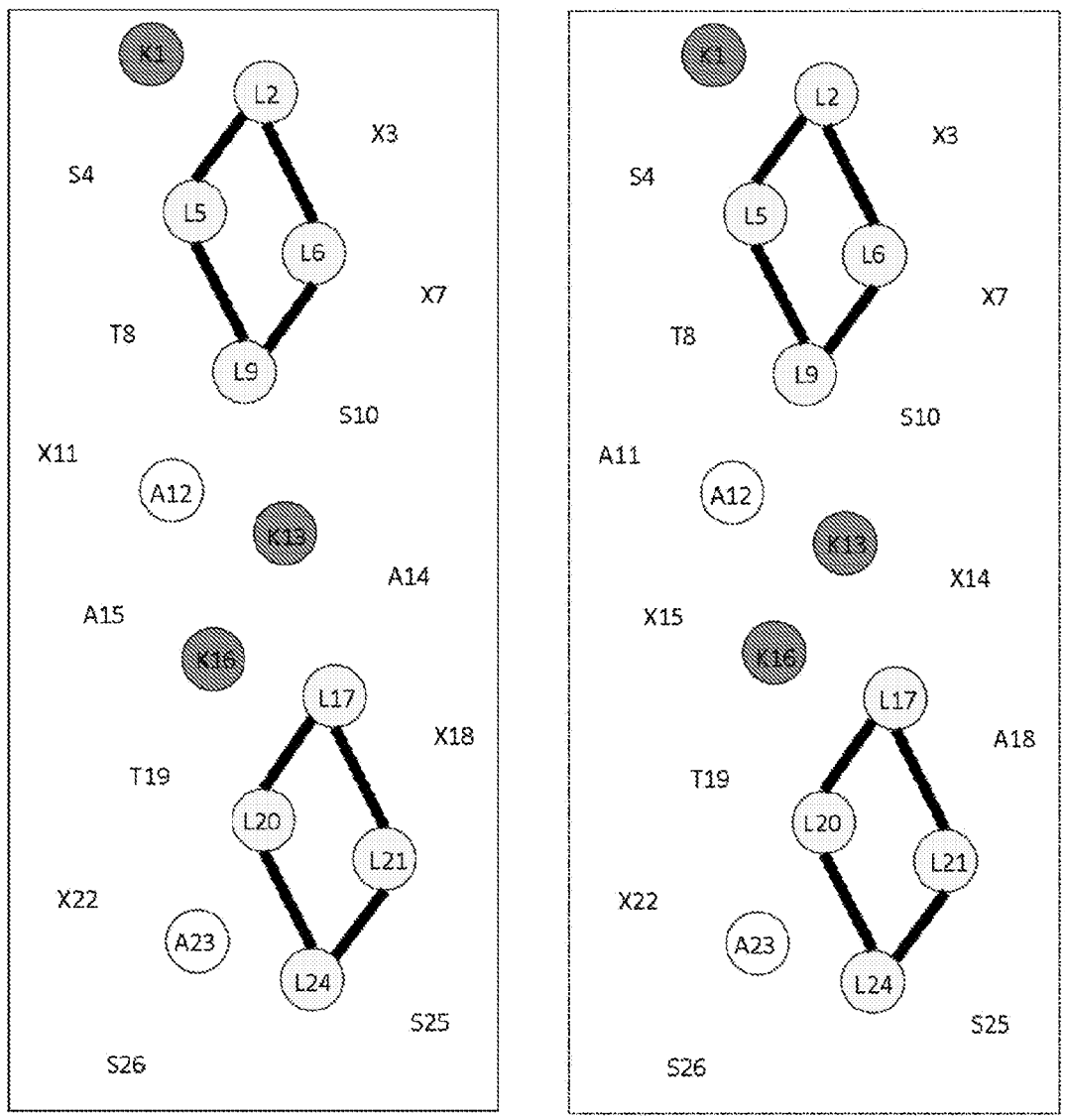

The unprecedented discoveries from this study are from the polar face substitutions of Lys, Orn, Dbu, Dpr, and Arg. The six Lys residues in D84 were replaced with six Orn residues (D85), six Dbu residues (D86), six Dpr residues (D105) and six Arg residues (D87) at positions 3, 7, 11, 18, 22, and 26 on the polar face (FIG. 3A). The geometric mean MIC using seven strains of Acinetobacter baumannii resistant to polymyxin B and colistin (Tables 9B and Table 9C) varied from 0.5 to 1.2 µM for D84, D85, D86, and D105). The dramatic change between these analogs was in the hemolytic activity. D87 (6 Arg residues on the polar face) the $HC_{50}$ value was 4.0 µM whereas the $HC_{50}$ value for the Lys analog (D84) was 54.3 µM, the Orn analog (D85) was 146.1 µM, the Dbu analog (D86) was >742 µM and the Dpr analog (D105) was >1148 µM. The resulting therapeutic index for this series of analogs was D84 (108.6), D85 (292.2), D86 (>742) and D105 (>957). Thus, shortening the length of the side chain prior to the side chain amino group had a dramatic effect on the therapeutic index.

Figure 8:
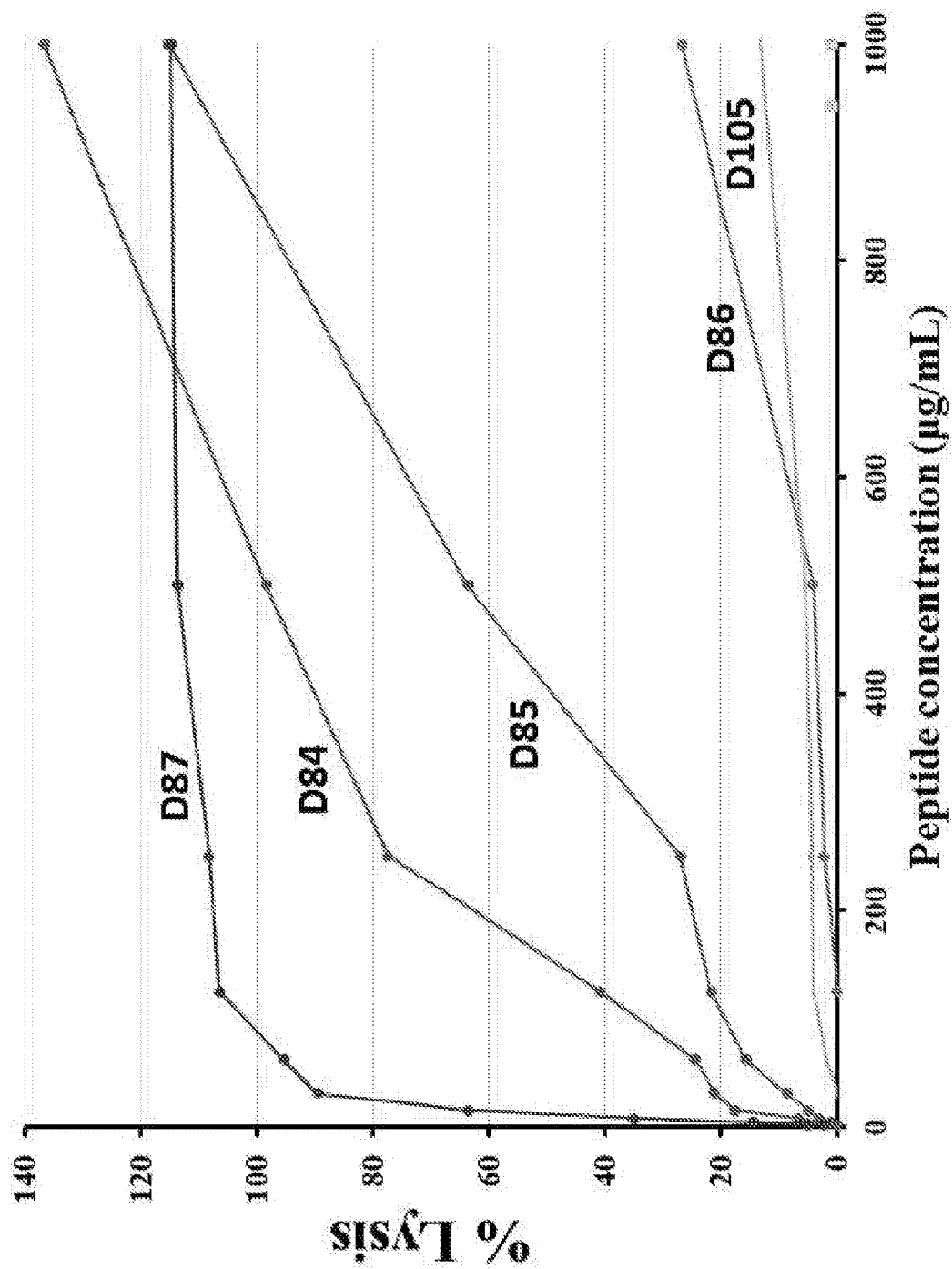
FIGS. 8-11 are graphical comparisons of percentage lysis of human blood cells versus peptide concentration.
Figure 9:
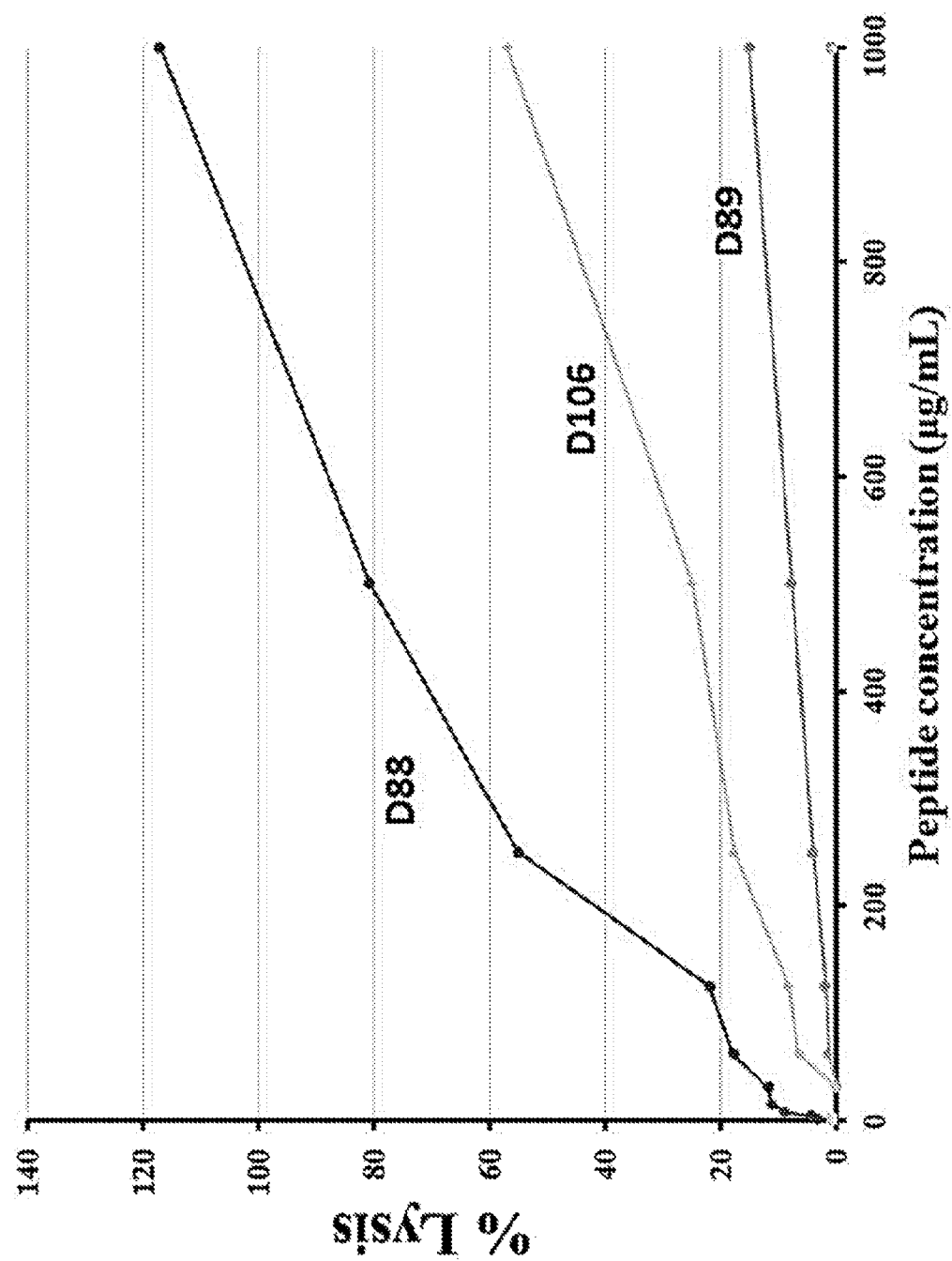

Clearly the use of Dbu and Dpr residues on the polar face greatly decreases the hemolytic activity and thus has a major impact on the therapeutic index. The inventors also compared antimicrobial peptides with 6 positively charged residues on the polar face at positions, 3, 7, 14, 15, 22, and 26. As shown in Tables 9B and 9C peptides D88 (six Lys residues on the polar face), D89 (six Dbu residues on the polar face and D106 (six Dpr residues on the polar face) the $MIC_{GM}$ values were similar varying from 0.4 to 0.8 µM. However, there were dramatic changes in the hemolytic activity ($HC_{50}$ (µM) varied from 80.6 µM for the Lys peptide (D88), 340.2 µM for the Dpr peptide (D106) to >1112 µM for the Dbu peptide (D89). These two peptides D105 (Dpr) and D89 (Dbu) have basically very little hemolysis even at 1000 µg of peptide per ml (FIG. 8 and FIG. 9) which show the plots of percentage lysis of human red blood cells versus peptide concentration.

Figure 10:
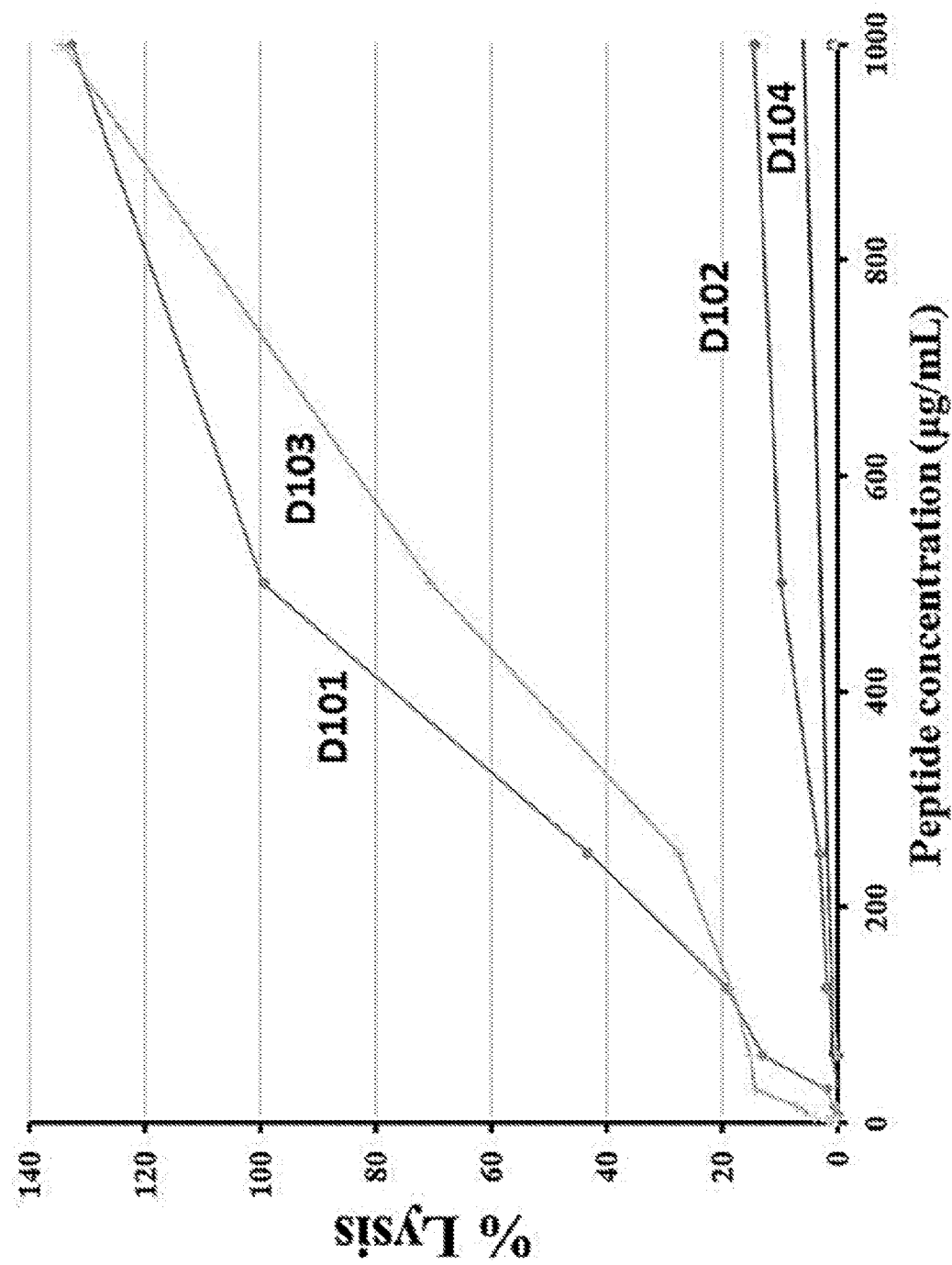
Figure 11:
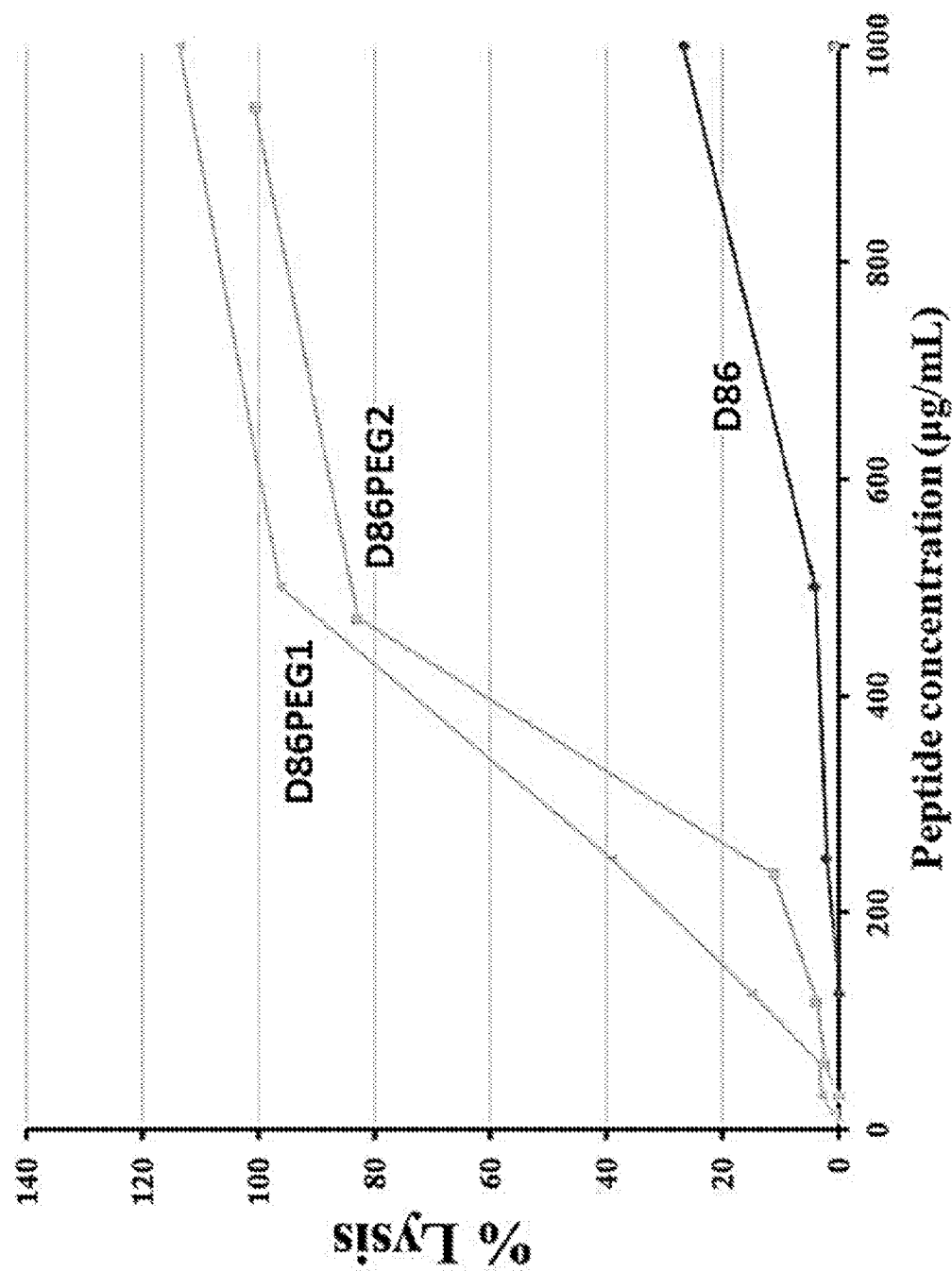
Figure 12A:
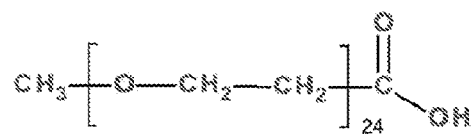
FIGS. 12A-12D show the chemical structures of polyethylene glycol (PEG) polymeric groups linked antimicrobial peptides of this disclosure.
Figure 12B:
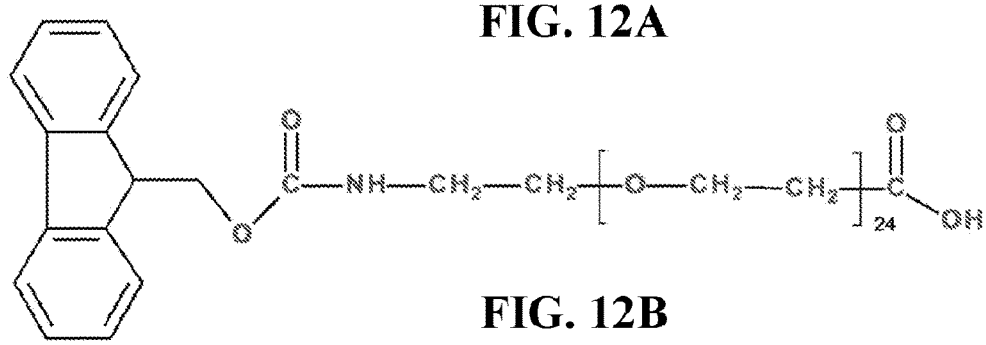
Figure 12C:
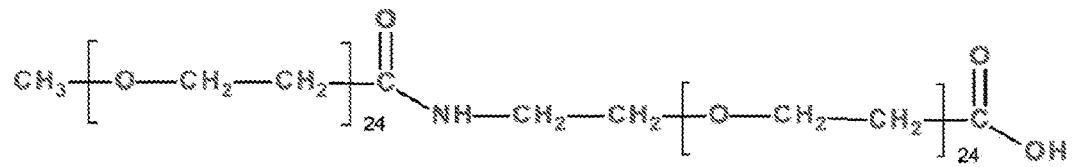
Figure 12D:
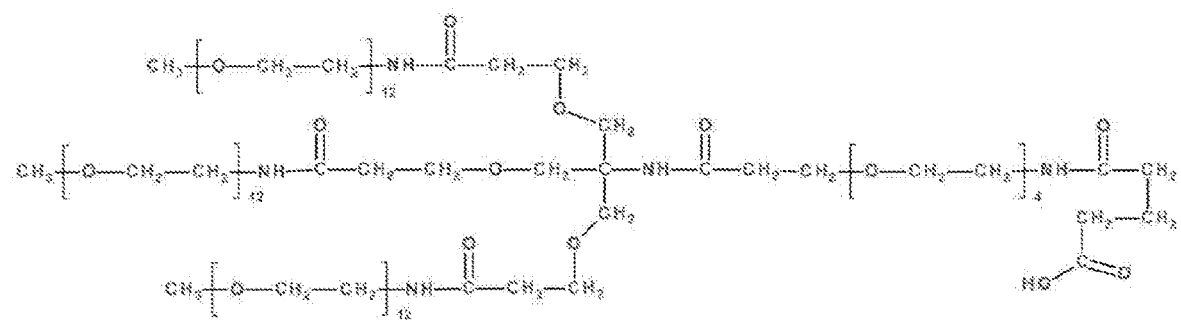
Figure 13A:
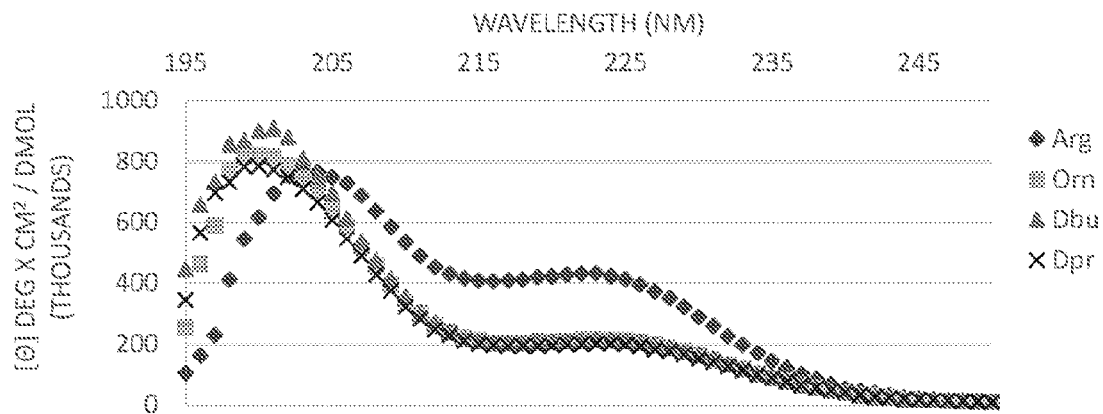
FIGS. 13A-13X show circular dichroism spectroscopy (CD) analysis results for AMPs of this disclosure. CD results for peptide D41 in aqueous media appear in FIG. 13A; for peptide D41 in 50% trifluoroethanol (TFE) media appear in FIG. 13B; for peptide D41-Arg appear in FIG. 13C; for peptide D41-Orn appear in FIG. 13D; for peptide D41-Dbu appear in FIG. 13E; for peptide D41-Dpr appear in FIG. 13F; for peptides D84, D85, D86, D87, and D105 in aqueous media appear in FIG. 13G; for peptides D84, D85, D86, D87, and D105 in 50% TFE media appear in FIG. 13H; for peptide D84 appear in FIG. 13I; for peptide D85 appear in FIG. 13J; for peptide D86 appear in FIG. 13K; for peptide D87 appear in FIG. 13L; for peptide D105 appear in FIG. 13M; for peptides D88, D89, and D106 in aqueous media appear in FIG. 13N; for peptides D88, D89, and D106 in 50% TFE media appear in FIG. 13O; for peptide D88 appear in FIG. 13P; for peptide D89 appear in FIG. 13Q; for peptide D106 appear in FIG. 13R; for two PEG-modified D86 peptides in aqueous or 50% TFE media appear in FIG. 13S; for two PEG-modified D86 peptides as well as the corresponding unmodified D86 peptide, in both aqueous or 50% TFE media, appear in FIG. 13T; for peptide D101 appear in FIG. 13U; for peptide D102 appear in FIG. 13V; for peptide D103 appear in FIG. 13W; and, for peptide D104 appear in FIG. 13X.
Figure 13B:
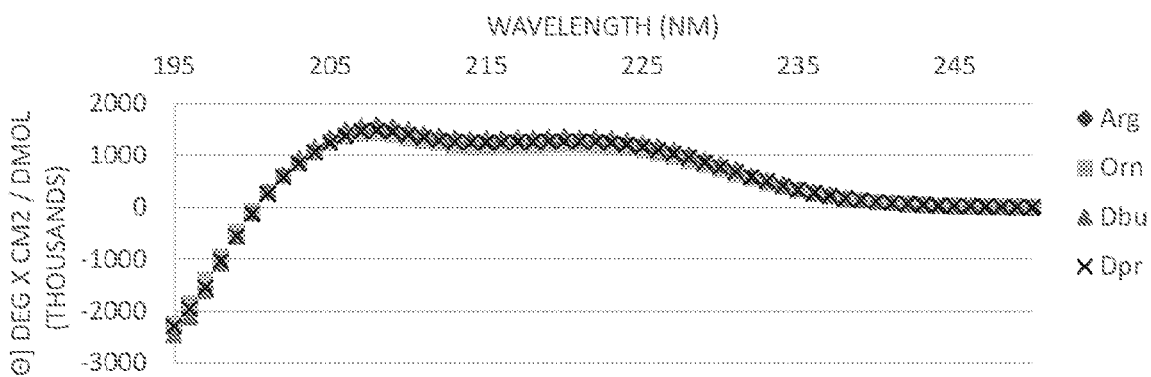
Figure 13C:
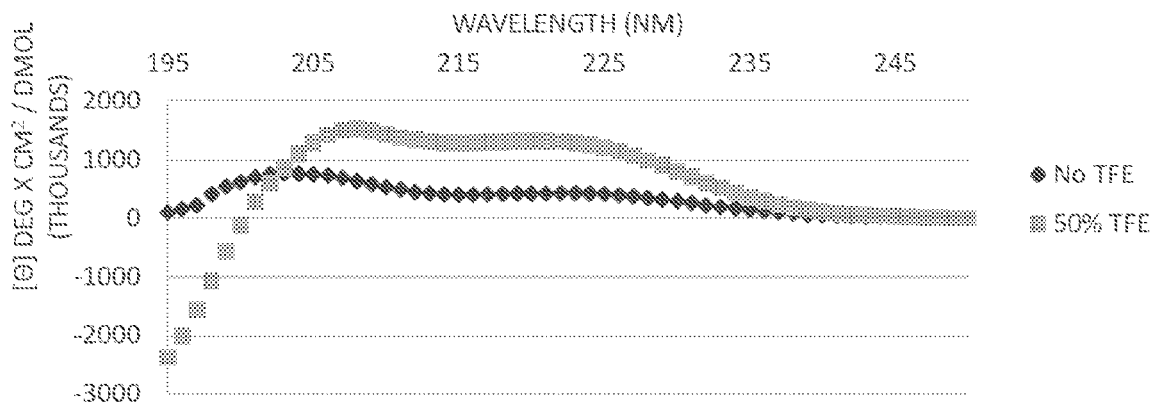
Figure 13D:
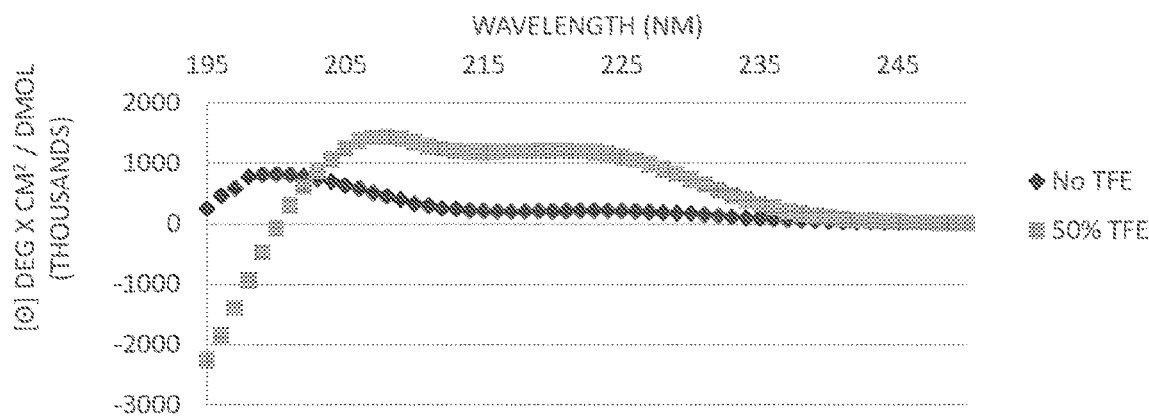
Figure 13E:
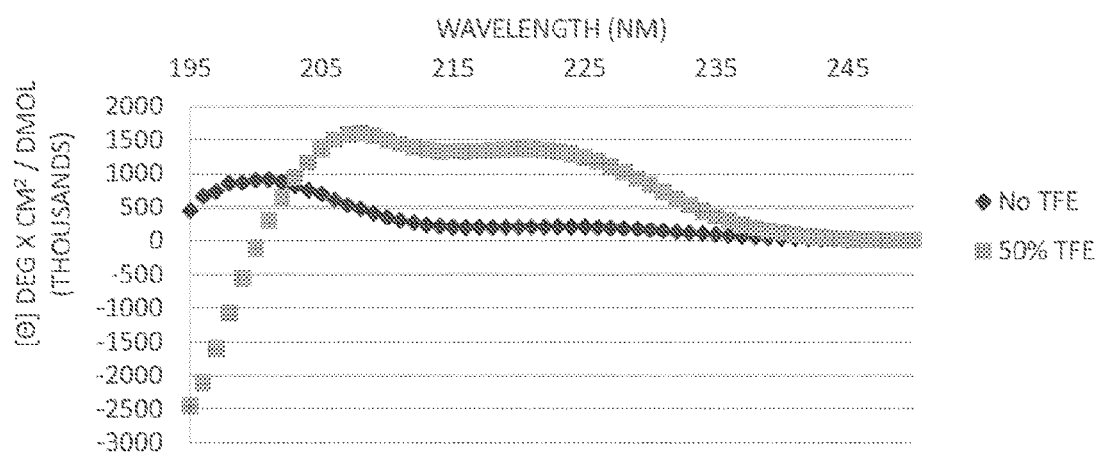
Figure 13F:
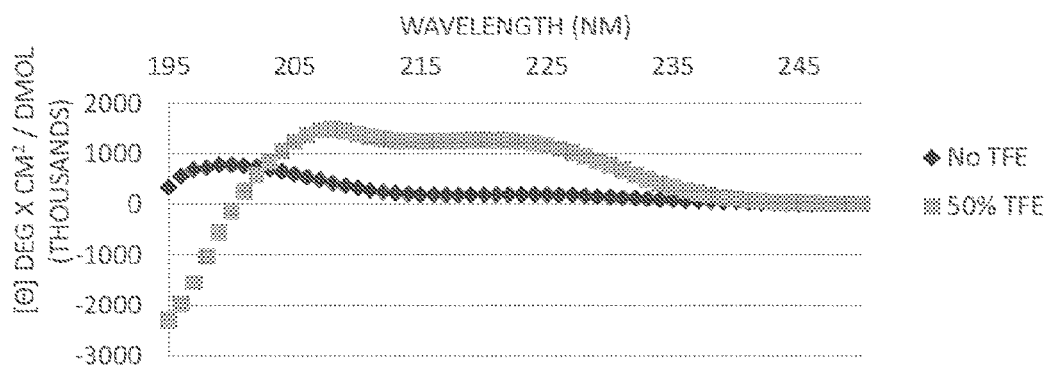
Figure 13G:
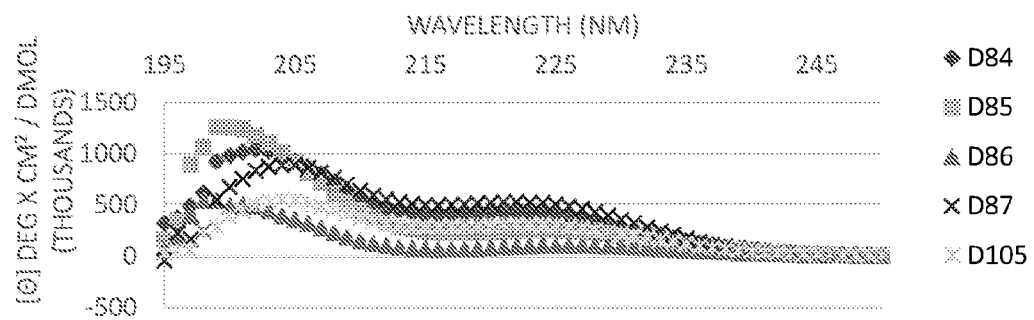
Figure 13H:
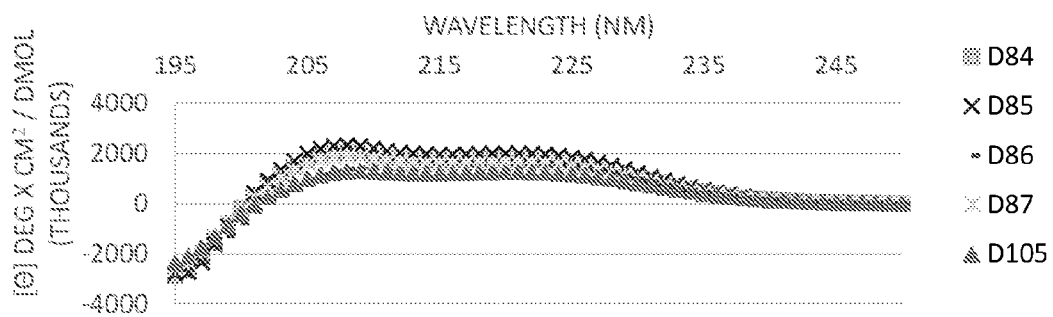
Figure 13I:
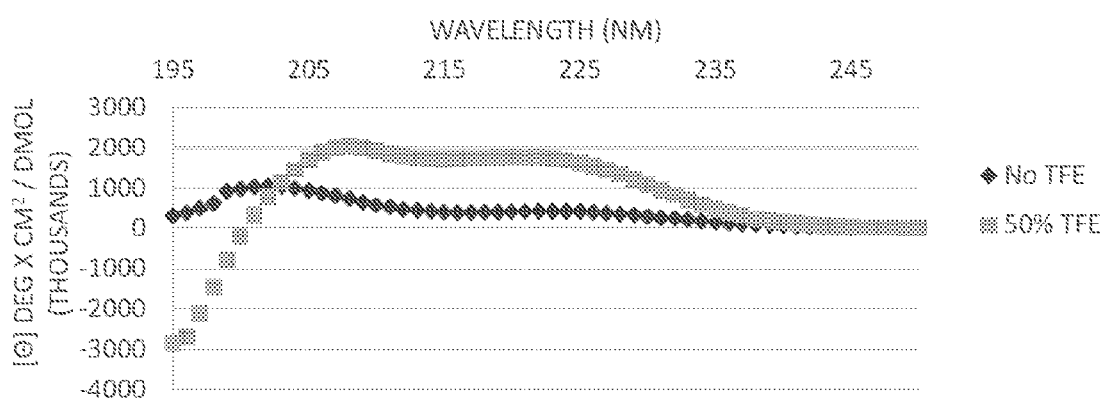
Figure 13J:
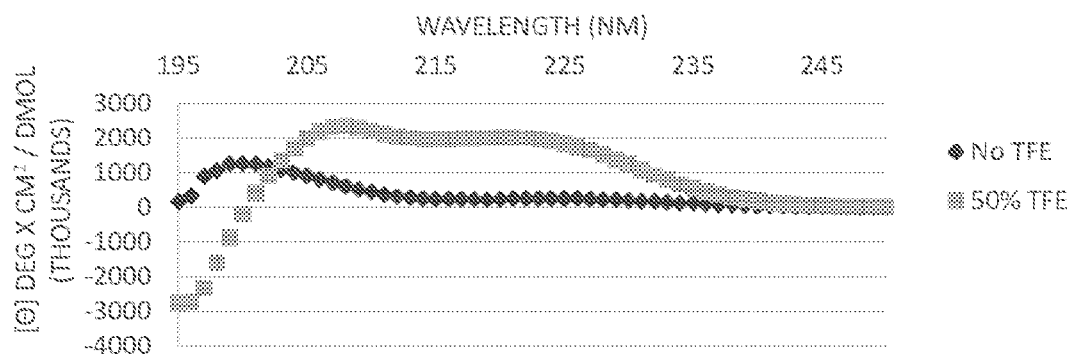
Figure 13K:
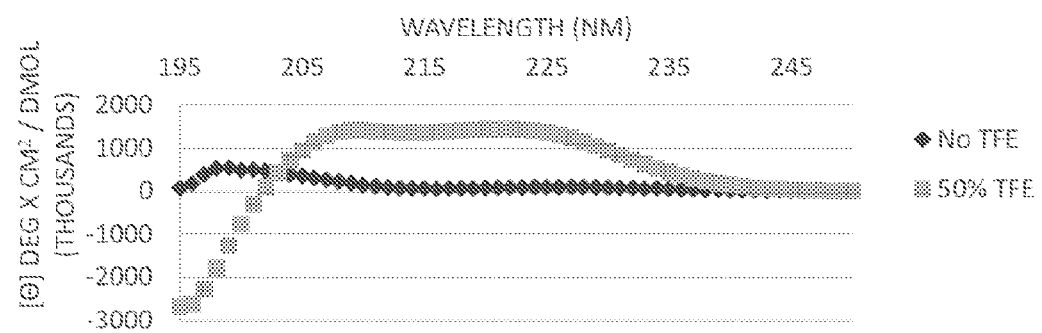
Figure 13L:
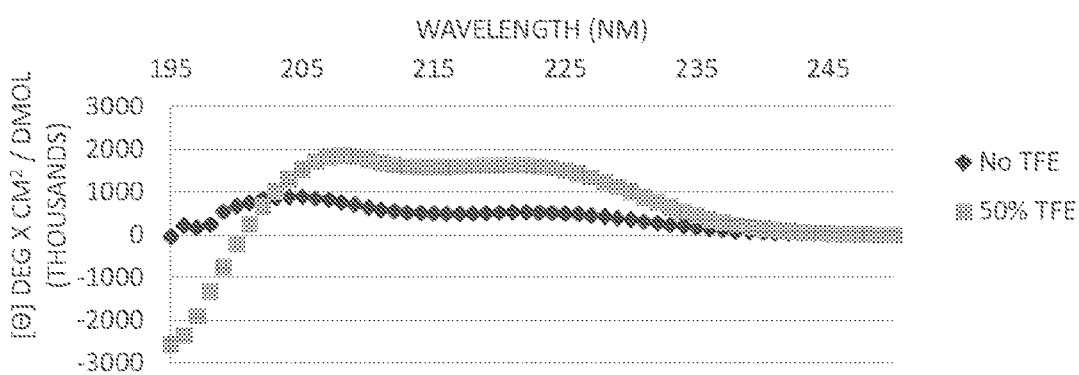
Figure 13M:
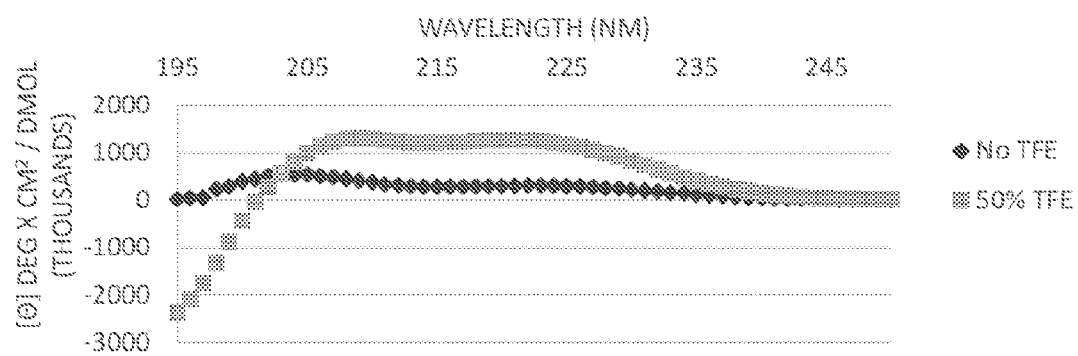
Figure 13N:
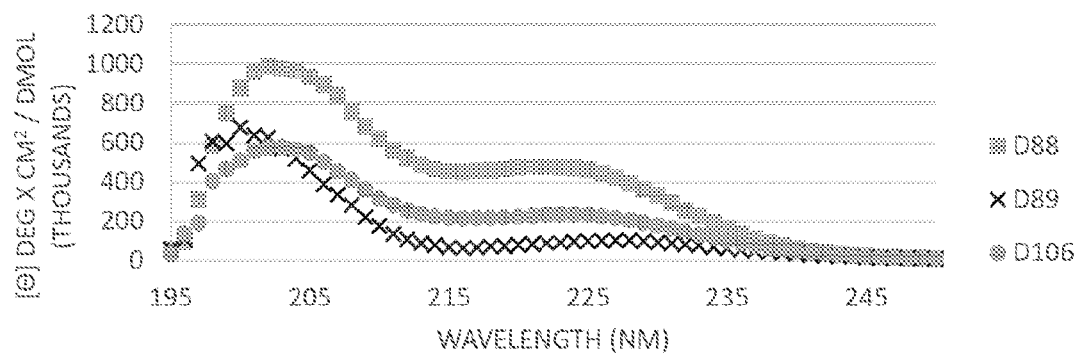
Figure 13O:
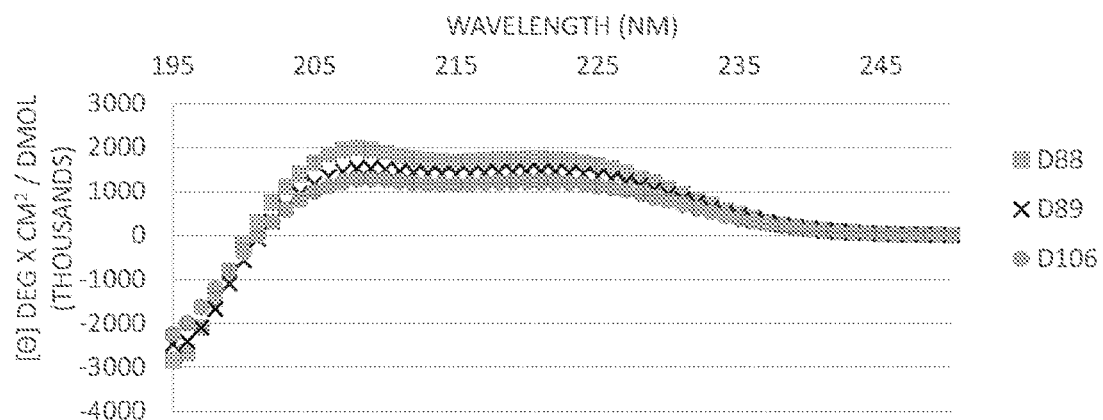
Figure 13P:
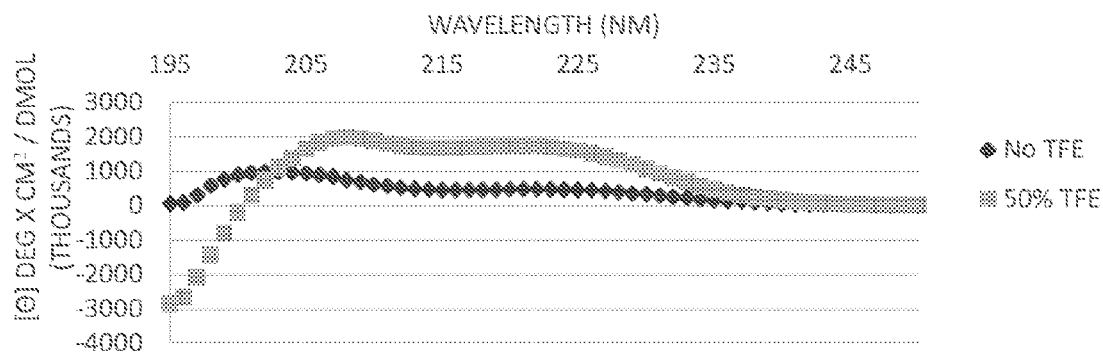
Figure 13Q:
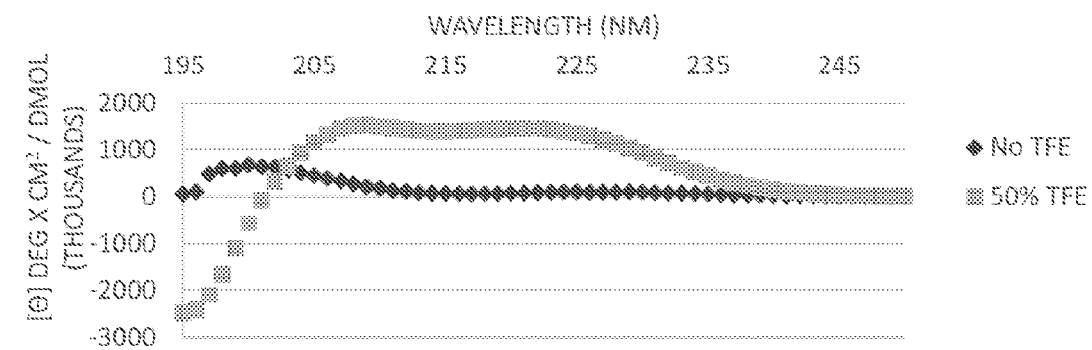
Figure 13R:
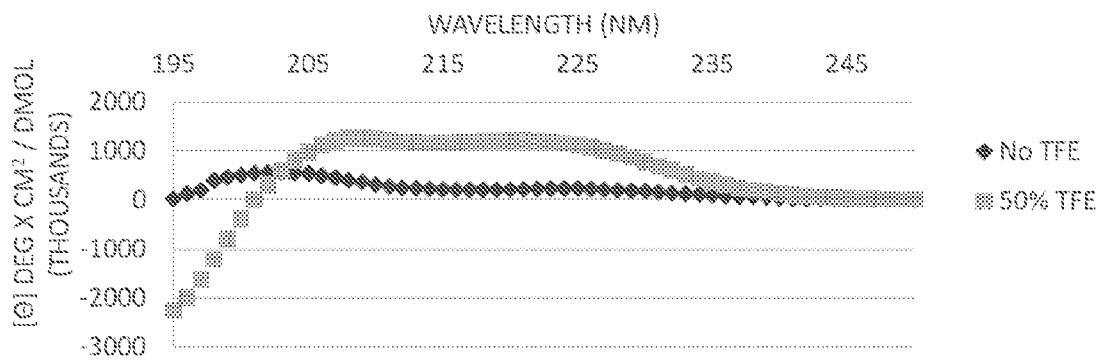
Figure 13S:
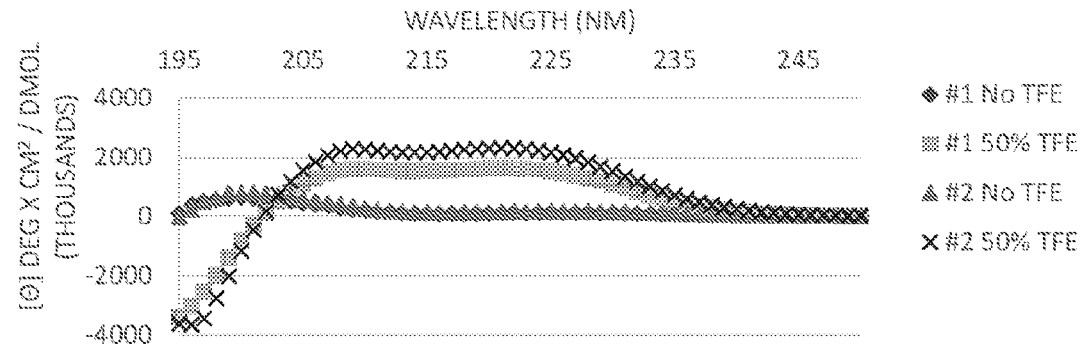
Figure 13T:
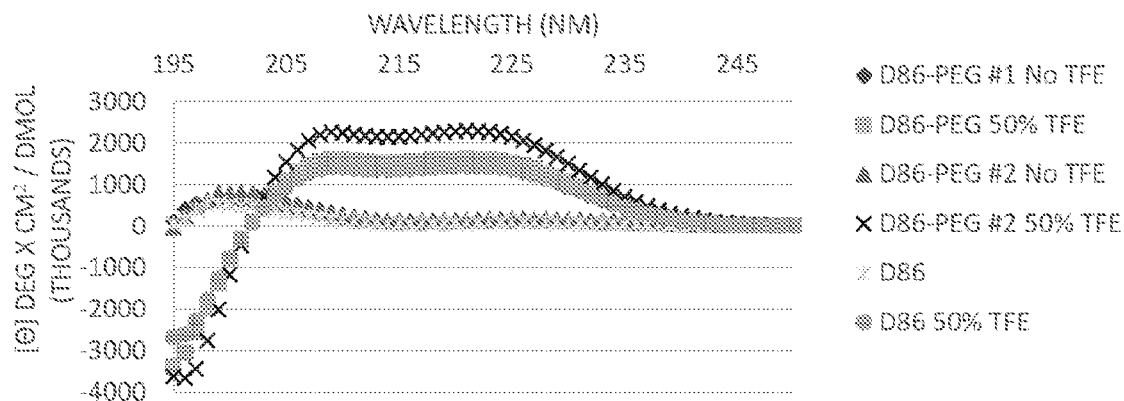
Figure 13U:
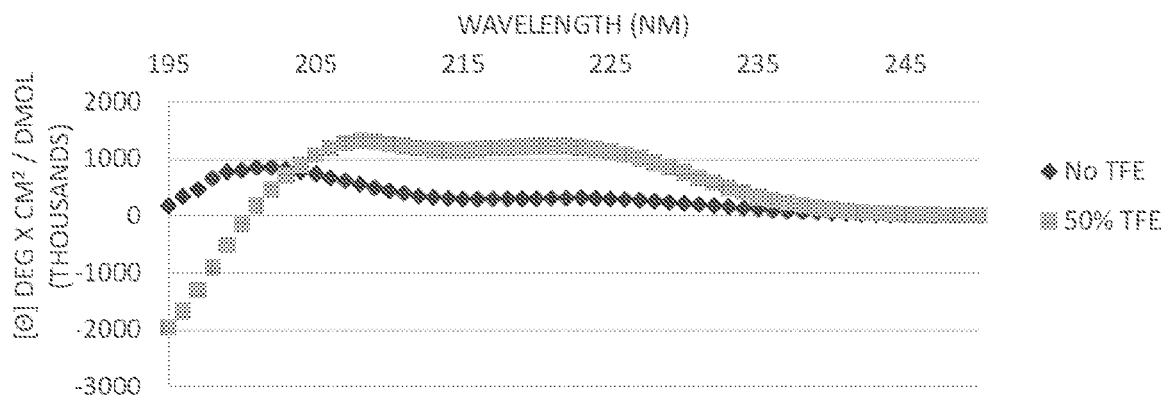
Figure 13V:
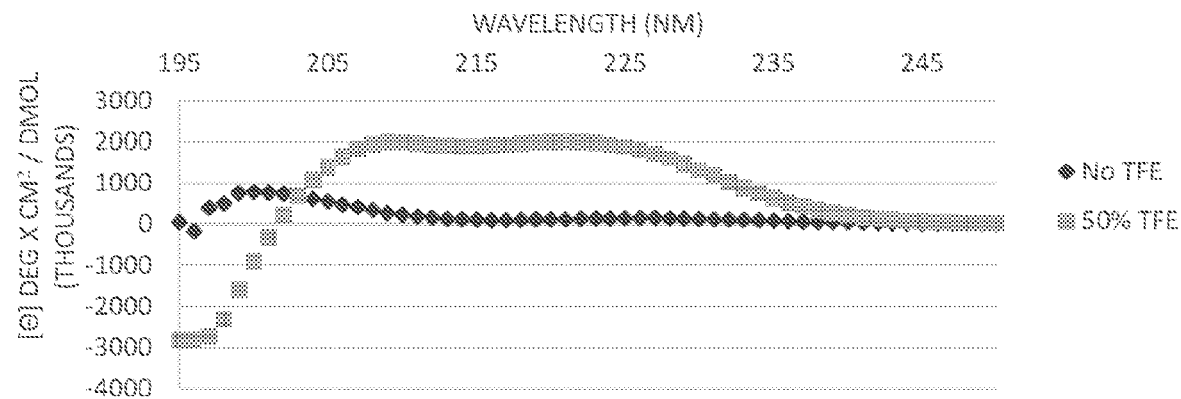
Figure 13W:
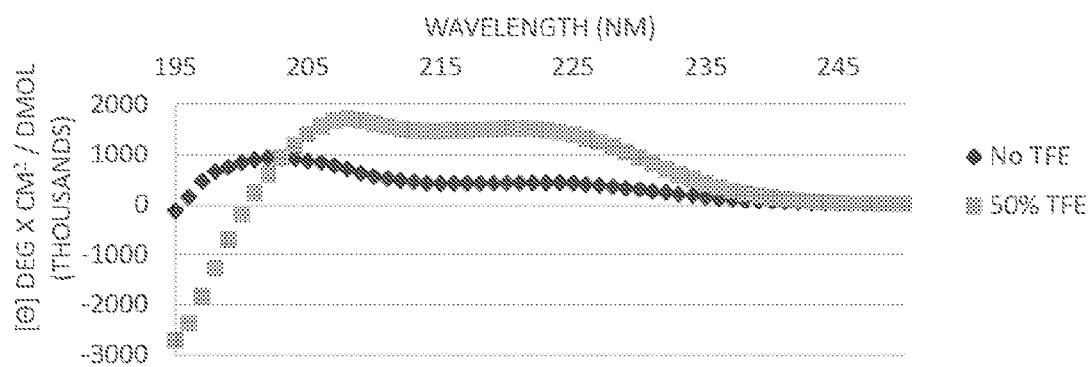
Figure 13X:
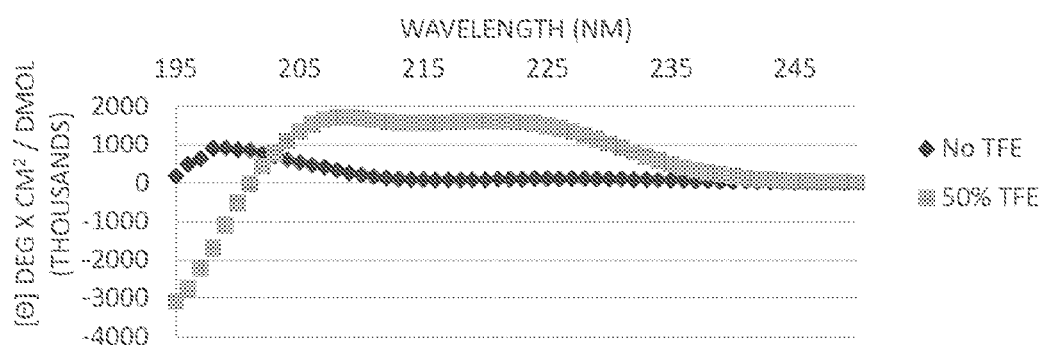

Similarly, the peptide analogs D102 and D104 showed basically no hemolysis of human red blood cells (FIG. 10). These two peptides have 5 positively charged Dbu residues on the polar face instead of six as described above. Clearly, having Dbu or Dpr residues on the polar face instead of Arg, Lys, or Orn dramatically improves the therapeutic index and preferred analogs for use as therapeutics to treat Gram-negative bacterial infections.

Example 7

Gram-Negative Pathogen Selectivity

The inventors have shown that the substitution of one or two specificity determinant(s) in broad spectrum native AMPs, Piscidin 1 and Dermaseptin S4 resulted in new AMPs that encode selectivity for Gram-negative pathogens and remove both Gram-positive activity and hemolytic activity from broad-spectrum AMPs (Jiang, Z., et al., Pharmaceuticals 2014, supra; Jiang, Z.; et al., 2015, supra). The Gram-negative selectivity factor for D-Piscidin 1 (19K) (one-specificity determinant) resulted in a 55-fold improvement in selectivity ($MIC_{GM}$, S. aureus/$MIC_{GM}$ A. baumannii) and D-Dermaseptin S4 (L7K, A14K) (two-specificity determinants) resulted in a >99-fold improvement in A. baumannii selectivity compared to S. aureus. These results suggested that amphipathic alpha-helical AMPs can be designed with selectivity for Gram-negative pathogens. As shown in Table 10, the antimicrobial activity against A. baumannii and P. aeruginosa is far superior to S. aureus. The Gram-negative selectivity factor ranges for the four peptides D33-D36 from 16 to 88 for A. baumannii and 5 to 22 for P. aeruginosa.

TABLE 10

Summary of Antimicrobial Activity and Gram-negative Pathogen Selectivity

| | Antimicrobial activity | | | Gram-negative selectivity factor[b] | |
|---|---|---|---|---|---|
| Peptide Name | *A. baumannii* $MIC_{GM}(\mu M)^a$ | *P. aeruginosa* $MIC_{GM}(\mu M)^a$ | *S. aureus* $MIC_{GM}(\mu M)^a$ | $MIC_{GM}$ (*S. aureus*) $MIC_{GM}$ (*A. baumannii*) | $MIC_{GM}$ (*S. aureus*) $MIC_{GM}$ (*P. aeruginosa*) |
| D33 | 0.2 | 1.8 | 14.6 | 73.0 | 8.1 |
| D34 | 0.3 | 1.6 | 26.4 | 88.0 | 16.5 |
| D35 | 0.4 | 0.9 | 20.2 | 50.5 | 22.4 |
| D36 | 0.4 | 1.2 | 6.3 | 15.8 | 5.3 |

[a]$MIC_{GM}$ is the geometric mean of the MIC values from 14 strains of *A. baumannii*, 7 of which are resistant to polymyxin B and colistin (antibiotics of last resort to treat Gram-negative infections); 6 diverse clinical isolates of *P. aeruginosa* and 17 strains of *S. aureus*, 8 of which are MRSA strains and 9 of which are MSSA strains.
[b]The ratio of $MIC_{GM}$ (*S. aureus*) versus $MIC_{GM}$(*A. baumannii*) or $MIC_{GM}$ (*S. aureus*) versus $MIC_{GM}$ (*P. aeruginosa*) indicates selectivity for Gram-negative versus Gram-positive bacteria where the larger the value, the greater the selectivity for *A. baumannii* or *P. aeruginosa* compared to *S. aureus*.

AMP D34 has the largest discrimination between *A. baumannii* and *S. aureus* with a selectivity factor of 88 while AMP D35 has the largest discrimination between *P. aeruginosa* and *S. aureus* with a selectivity factor of 22.4 (Table 10). These results support the concept that Gram-negative selectivity can be controlled by the number and location of the positively charged residues on the polar face of the amphipathic alpha-helix, as well as by their relative position to the specificity determinants in the center of the non-polar face.

Example 8

Antimicrobial Activity of AMPs in the Presence of Human Sera

A critical component to the systemic use of AMPs to treat bacterial infections is the extent of AMP binding to serum proteins. In addition, since only the unbound AMP is available to interact with the therapeutic target, the extent of serum binding can have significant effects on efficacy. To address this issue, the inventors determined the MIC values of these peptide candidates in the presence of Mueller Hinton (MH) medium and MH medium supplemented with human sera (25% v/v). This assay estimates the in vivo bioavailability of the AMPs. The appropriate non-specific affinity of a drug for serum proteins can significantly improve in vivo half-life and decrease clearance. An increase in MIC in serum is attributed to inhibition of antimicrobial activity due to serum protein binding. As shown in Table 11, the four AMPs without specificity determinants (D37, D38, D39 and D40) have no activity against *A. baumannii* in the presence of 25% human sera. In contrast, the four AMPs with specificity determinants (D33, D34, D35 and D36) have excellent activity against *A. baumannii*.

TABLE 11

Antimicrobial activity against *A. baumannii* strain 649 in the presence and absence of 25% human sera

| | MIC (µM) | |
|---|---|---|
| Peptide Name | No serum | 25% human serum |
| With specificity determinants | | |
| D33 | 0.1 | 0.7 |
| D34 | 0.2 | 1.4 |
| D35 | 0.4 | 1.4 |
| D36 | 0.4 | 0.7 |

TABLE 11-continued

Antimicrobial activity against *A. baumannii* strain 649 in the presence and absence of 25% human sera

| | MIC (µM) | |
|---|---|---|
| Peptide Name | No serum | 25% human serum |
| Without specificity determinants | | |
| D37 | 2.9 | >92.8 |
| D38 | 0.7 | >92.8 |
| D39 | 1.4 | >92.8 |
| D40 | 2.9 | >92.8 |

There is only a 1.8 to 7-fold loss of antimicrobial activity depending on the AMP (Table 11) which is due to weak and non-specific binding to human serum proteins, a desired behavior. High affinity binding such as that observed for AMPs (D37 to D40) eliminates these AMPs for further study. These results show the importance of specificity determinants in maintaining weak and non-specific binding to serum proteins and preventing any significant loss of antimicrobial activity. It is also interesting, that the specificity determinants enhance antimicrobial activity.

Example 9

PEGylation of Peptides

PEGylation of peptides usually involves the covalent attachment of polyethylene glycol chains to peptides. PEGylation may improve the pharmacologic properties of the peptide drug by, for example, increasing half-life, improving solubility and reducing immunogenicity and antigenicity. Chemical modification of the peptide using polyethylene glycol (PEG) can improve drug performance with minimal increase in manufacturing cost. PEG is a highly investigated polymer that is used in covalent modification of peptides and proteins. The effects of PEGylation on peptide pharmacokinetics include avoidance of reticuloendothelial clearance, mitigation of immunogenicity and reduction of enzymatic proteolysis (the all D-peptides used in this study prevent enzymatic proteolysis) and of losses by renal filtration, with potentially beneficial changes in biodistribution. These effects can dramatically increase the half-life of a peptide in vivo, with potential collateral improvement in bioavailability but without adversely affecting binding and activity of the peptide ligand.

The inventors investigated the effects of monodesperse, discrete PEG derivatives (dPEG) purchased from Peptides International. These dPEGs are not purified from a polymeric mixture and thus contain no other PEG homologues (only the one selected as the desired product), resulting in a single compound with a single molecular weight. The inventors chose three dPEGs to derivatize the N-terminal amino group of our antimicrobial peptides (FIGS. 12A-12D):
1. m-dPEG$_{24}$-acid, CH$_3$—(O—CH$_2$—CH$_2$)$_{24}$—COOH; C$_{50}$H$_{1000}$O$_{26}$: 1117.31)
2. Carboxyl-dPEG$_4$-(mdPEG$_{12}$)$_3$, (C$_{104}$H$_{203}$N$_5$O$_{50}$: 2323.72) (tribranched)
3. Fmoc-amido-dPEG$_{24}$-acid, Fmoc-NH—CH$_2$—CH$_2$(O—CH$_2$—CH$_2$)$_{24}$—COOH, (C$_{66}$H$_{113}$NO$_{28}$: 1368.59)

This allows N-terminal modification with the Fmoc-amido-dPEG$_{24}$-acid followed by removal of the Fmoc group and coupling of m-dPEG$_{24}$-acid to give a monomeric (see FIG. 12A) C$_{101}$H$_{199}$NO$_{50}$: 2727.63.

The first step in coupling dPEG monomethyl ether to a peptide was to activate m-dPEG with a functional group. Its nature depends on the available reactive groups in the peptide, such as lysine, aspartic acid, cysteine, glutamic acid, serine, threonine, the N-terminal amine and the C-terminal carboxylic acid or other specific sites. The inventors restricted these studies to PEG-derivatization of the N-terminal α-amino group (Table 12) to show the general utility of m-dPEG on antimicrobial activity, hemolytic activity and its potential to enhance the effects on peptide pharmacokinetics.

TABLE 12

PEG-derivatized AMPs synthesized and tested.

| Peptide | Mass |
|---|---|
| 1. D86 with free α-amino group | 2655.3 |
| 2. m-dPEG$_{24}$-D86 | 3754.6 |
| 3. Tribranched m-dPEG-D86 | 4961.0 |
| 4. m-dPEG$_{24}$-NH(CH$_2$)$_2$-dPEG$_{24}$-D86 | 4882.9 |

The inventors designed three N-terminal PEGylated D-86 peptides: m-dPEG$_{24}$-D86, tribranched m-dPEG-D86 and m-dPEG$_{24}$—NH(CH$_2$)$_2$-dPEG$_{24}$-D86 (FIGS. 12A-12D; Table 12). The PEGs were coupled to the N-terminal-α-amino-acid residue of the D86-peptide resin in N-methylpyrrolidone (NMP) using standard peptide coupling method with 3 equivalents HCTU/Cl-HOBt and 6 equivalents DIEA. The linear PEG couplings to the D86-peptide resin were repeated at least three or four times to complete the pegylations. The sterically hindered tribranched PEG could not be coupled to the N-terminal D86-peptide resin. However, the coupling of the second linear PEG to the to the NH$_2$-PEG-D86 peptide resin was easy and did not require re-couplings. This suggested the use of a spacer like ε-aminocaproic-(ACA) or 10-aminodecanoic- or 12-aminododecanoic-acid between the first PEG-chain and the N-terminal D86 peptide for better coupling yields. PEG couplings may also be made at a side-chain of Lys on the polar face of these AMPS.

Antimicrobial activity and hemolytic activity of these PEG-derivatized AMPS is provided in Tables 9B and 9C.

The present disclosure is not to be limited in scope by the specific embodiments described herein which are intended as single illustrations of individual aspects of this disclosure, and functionally equivalent methods and components are within the scope of this disclosure. Indeed, various modifications of this disclosure, in addition to those shown and described herein will become apparent to those skilled in the art from the foregoing description and accompanying drawings. Such modifications are intended to fall within the scope of the claims.

What is claimed is:

1. An antimicrobial peptide (AMP) comprising the amino acid sequence selected from the group consisting of:
   KL(Dbu)SLL(Dbu)TLS(Dbu)AKAAKL(Dbu)TLL(Dbu)ALS(Dbu) (SEQ ID NO:26),
   KL(Dbu)SLL(Dbu)TLSAAK(Dbu)(Dbu)KLATLL(Dbu)ALS(Dbu) (SEQ ID NO:31),
   KL(Dpr)SLL(Dpr)TLS(Dpr)AKAAKL(Dpr)TLL(Dpr)ALS(Dpr) (SEQ ID NO:28),
   KL(Dpr)SLL(Dpr)TLSAAK(Dpr)(Dpr)KLATLL(Dpr)ALS(Dpr) (SEQ ID NO:32),
   KL(Dbu)SLL(Dbu)TLS(Dbu)AKAAKL(Dbu)TLL(Dbu)ALSS (SEQ ID NO:35), and
   KL(Dbu)SLL(Dbu)TLSAAK(Dbu)(Dbu)KLATLL(Dbu)ALSS (SEQ ID NO:38)
   Wherein:
   each residue is in the D-enantiomeric form.

2. The AMP of claim 1, which is covalently linked to a moiety selected from the group consisting of a polyethylene glycol (PEG) molecule, and an Fc region of human IgG immunogloblin linked to at least one of the amino-terminus or carboxyl-terminus of the peptide.

3. The AMP of claim 1, wherein the AMP inhibits propagation of a Gram-negative bacterium that is at least one of A. baumannii and P. aeruginosa.

4. The AMPs of claim 1, wherein the therapeutic index (calculated by the ratio of hemolytic activity and antimicrobial activity (MIC)) is at least 70.

5. The AMP of claim 1, wherein the AMP exhibits about a 10-fold to 90-fold increased selectivity for Gram-negative bacteria over Gram-positive bacteria, wherein the Gram-negative bacteria is Acinetobacter baumannii, and the Gram-positive bacteria is Staphylococcus aureus.

6. The AMP of claim 1 that exhibits at least a 6-fold decrease in hemolysis of human red blood cells compared to hemolysis exhibited by any one of SEQ ID NOs:24, 30, 34, or 37.

7. The AMP of claim 1, wherein the AMP is equally effective in inhibiting the propagation of an antibiotic-resistant prokaryote and an antibiotic-sensitive prokaryote.

8. A pharmaceutical composition comprising at least one peptide of claim 1, and a pharmaceutically acceptable carrier.

9. The pharmaceutical composition of claim 8, comprising a mono-phasic pharmaceutical composition suitable for parenteral or oral administration consisting essentially of a therapeutically-effective amount of the at least one peptide, and a pharmaceutically acceptable carrier.

10. A method of preventing or treating a microbial infection comprising administering to a subject in need thereof a therapeutically effective amount of at least one peptide of claim 1 by an administration route selected from oral, topical, subcutaneous, intravenous, intraperitoneal, intramuscular, intradermal, intrasternal, intraarticular injection, intrathecal, and infusion.

11. The method of claim 10, wherein the microbial infection is a Gram-negative bacterial infection.

* * * * *

SEQUENCE LISTING

```
<160> NUMBER OF SEQ ID NOS: 38

<210> SEQ ID NO 1
<211> LENGTH: 26
<212> TYPE: PRT
<213> ORGANISM: Artificial Sequence
<220> FEATURE:
<223> OTHER INFORMATION: Synthetic Peptide of Formula (I)
<220> FEATURE:
<221> NAME/KEY: VARIANT
<222> LOCATION: (1)..(1)
<223> OTHER INFORMATION: X1 in Formula (I).  Xaa is selected from Ala,
      Ser, Thr, Lys, Arg, Orn, Dpr and Dbu
<220> FEATURE:
<221> NAME/KEY: VARIANT
<222> LOCATION: (3)..(3)
<223> OTHER INFORMATION: X2 in Formula (I).  Xaa is selected from Ala,
      Ser, Lys, Arg, Orn, Dpr and Dbu
<220> FEATURE:
<221> NAME/KEY: VARIANT
<222> LOCATION: (4)..(4)
<223> OTHER INFORMATION: X3 in Formula (I).  Xaa is selected from Ser,
      Lys, Arg, Orn, Dpr and Dbu
<220> FEATURE:
<221> NAME/KEY: VARIANT
<222> LOCATION: (7)..(7)
<223> OTHER INFORMATION: X4 in Formula (I).  Xaa is selected from Ala,
      Ser, Lys, Arg, Orn, Dpr and Dbu
<220> FEATURE:
<221> NAME/KEY: VARIANT
<222> LOCATION: (8)..(8)
<223> OTHER INFORMATION: X5 in Formula (I).  Xaa is selected from Ser,
```

```
        Thr, Lys, Arg, Orn,
        Dpr and Dbu
<220> FEATURE:
<221> NAME/KEY: VARIANT
<222> LOCATION: (11)..(11)
<223> OTHER INFORMATION: X6 in Formula (I).  Xaa is selected from Ala,
        Ser, Lys, Arg, Orn, Dpr and Dbu
<220> FEATURE:
<221> NAME/KEY: VARIANT
<222> LOCATION: (13)..(13)
<223> OTHER INFORMATION: X7 in Formula (I).  Xaa is selected from Ala,
        Lys, Arg, Orn, Dpr and Dbu
<220> FEATURE:
<221> NAME/KEY: VARIANT
<222> LOCATION: (14)..(15)
<223> OTHER INFORMATION: X8 and X9 in Formula (I).  Xaa is selected from
        Ala, Ser, Lys, Arg, Orn, Dpr and Dbu
<220> FEATURE:
<221> NAME/KEY: VARIANT
<222> LOCATION: (16)..(16)
<223> OTHER INFORMATION: X10 in Formula (I).  Xaa is selected from Ala,
        Lys, Arg, Orn, Dpr and Dbu
<220> FEATURE:
<221> NAME/KEY: VARIANT
<222> LOCATION: (18)..(18)
<223> OTHER INFORMATION: X11 in Formula (I).  Xaa is selected from Ala,
        Ser, Lys, Arg, Orn, Dpr and Dbu
<220> FEATURE:
<221> NAME/KEY: VARIANT
<222> LOCATION: (22)..(22)
<223> OTHER INFORMATION: X12 in Formula (I).  Xaa is selected from Ala,
        Ser, Lys, Arg, Orn, Dpr and Dbu
<220> FEATURE:
<221> NAME/KEY: VARIANT
<222> LOCATION: (25)..(25)
<223> OTHER INFORMATION: X13 in Formula (I).  Xaa is selected from Ser,
        Lys, Arg, Orn, Dpr and Dbu
<220> FEATURE:
<221> NAME/KEY: VARIANT
<222> LOCATION: (26)..(26)
<223> OTHER INFORMATION: X14 in Formula (I).  Xaa is selected from Ala,
        Ser, Thr, Lys, Arg, Orn, Dpr and Dbu

<400> SEQUENCE: 1

Xaa Leu Xaa Xaa Leu Leu Xaa Xaa Leu Ser Xaa Ala Xaa Xaa Xaa Xaa
1               5                   10                  15

Leu Xaa Thr Leu Leu Xaa Ala Leu Xaa Xaa
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 2

Ala Leu Lys Ser Leu Leu Lys Thr Leu Ser Lys Ala Ala Ala Ala Ala
1               5                   10                  15

Leu Lys Thr Leu Leu Lys Ala Leu Ser Lys
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 3

Ala Leu Lys Ser Leu Leu Lys Thr Leu Ser Ala Ala Ala Lys Lys Ala
1               5                   10                  15
```

Leu Ala Thr Leu Leu Lys Ala Leu Ser Lys
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 4

Ala Leu Lys Ser Leu Leu Ala Thr Leu Ser Lys Ala Ala Lys Lys Ala
1               5                   10                  15

Leu Lys Thr Leu Leu Ala Ala Leu Ser Lys
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 5

Ala Leu Ala Ser Leu Leu Lys Thr Leu Ser Lys Ala Ala Lys Lys Ala
1               5                   10                  15

Leu Lys Thr Leu Leu Lys Ala Leu Ser Ala
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 6

Ala Leu Lys Ser Leu Leu Lys Thr Leu Ser Lys Ala Lys Ala Ala Lys
1               5                   10                  15

Leu Lys Thr Leu Leu Lys Ala Leu Ser Lys
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 7

Ala Leu Lys Ser Leu Leu Lys Thr Leu Ser Ala Ala Lys Lys Lys Lys
1               5                   10                  15

Leu Ala Thr Leu Leu Lys Ala Leu Ser Lys
            20                  25

<210> SEQ ID NO 8
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 8

Ala Leu Lys Ser Leu Leu Ala Thr Leu Ser Lys Ala Lys Lys Lys Lys

Leu Lys Thr Leu Leu Ala Ala Leu Ser Lys
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 9

Ala Leu Ala Ser Leu Leu Lys Thr Leu Ser Lys Ala Lys Lys Lys Lys
1               5                   10                  15

Leu Lys Thr Leu Leu Lys Ala Leu Ser Ala
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 10

Ala Leu Lys Lys Leu Leu Lys Thr Leu Ser Lys Ala Lys Ala Ala Lys
1               5                   10                  15

Leu Lys Thr Leu Leu Lys Ala Leu Ser Lys
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 11

Ala Leu Lys Ser Leu Leu Lys Lys Leu Ser Lys Ala Lys Ala Ala Lys
1               5                   10                  15

Leu Lys Thr Leu Leu Lys Ala Leu Ser Lys
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 12

Ala Leu Lys Ser Leu Leu Lys Thr Leu Ser Lys Ala Lys Ala Ala Lys
1               5                   10                  15

Leu Lys Thr Leu Leu Lys Ala Leu Lys Lys
            20                  25

<210> SEQ ID NO 13
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 13

```
Ala Leu Lys Lys Leu Leu Lys Thr Leu Ser Lys Ala Ala Ala Ala Ala
1               5                   10                  15

Leu Lys Thr Leu Leu Lys Ala Leu Ser Lys
            20                  25
```

<210> SEQ ID NO 14
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 14

```
Ala Leu Lys Ser Leu Leu Lys Lys Leu Ser Lys Ala Ala Ala Ala Ala
1               5                   10                  15

Leu Lys Thr Leu Leu Lys Ala Leu Ser Lys
            20                  25
```

<210> SEQ ID NO 15
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 15

```
Ala Leu Lys Ser Leu Leu Lys Thr Leu Ser Lys Ala Ala Ala Ala Ala
1               5                   10                  15

Leu Lys Thr Leu Leu Lys Ala Leu Lys Lys
            20                  25
```

<210> SEQ ID NO 16
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 16

```
Glu Leu Glu Lys Gly Gly Leu Glu Gly Glu Lys Gly Gly Lys Glu Leu
1               5                   10                  15

Glu Lys
```

<210> SEQ ID NO 17
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (13)..(13)
<223> OTHER INFORMATION: Xaa is selected from Lys, Arg, Orn, Dpr and Dbu
<220> FEATURE:
<221> NAME/KEY: VARIANT
<222> LOCATION: (16)..(16)
<223> OTHER INFORMATION: Xaa is selected from Lys, Arg, Orn, Dpr and Dbu

<400> SEQUENCE: 17

```
Ala Leu Lys Lys Leu Leu Lys Thr Leu Ser Lys Ala Xaa Ala Ala Xaa
1               5                   10                  15

Leu Lys Thr Leu Leu Lys Ala Leu Ser Lys
            20                  25
```

<210> SEQ ID NO 18

```
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 18

Ala Leu Lys Lys Leu Leu Lys Thr Leu Ser Lys Ala Lys Ala Ala Lys
1               5                   10                  15

Leu Lys Thr Leu Leu Lys Ala Leu Ser Lys
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: Orn
<220> FEATURE:
<221> NAME/KEY: MOD_RES
<222> LOCATION: (16)..(16)
<223> OTHER INFORMATION: Orn

<400> SEQUENCE: 19

Ala Leu Lys Lys Leu Leu Lys Thr Leu Ser Lys Ala Xaa Ala Ala Xaa
1               5                   10                  15

Leu Lys Thr Leu Leu Lys Ala Leu Ser Lys
            20                  25

<210> SEQ ID NO 20
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: Dbu
<220> FEATURE:
<221> NAME/KEY: MOD_RES
<222> LOCATION: (16)..(16)
<223> OTHER INFORMATION: Dbu

<400> SEQUENCE: 20

Ala Leu Lys Lys Leu Leu Lys Thr Leu Ser Lys Ala Xaa Ala Ala Xaa
1               5                   10                  15

Leu Lys Thr Leu Leu Lys Ala Leu Ser Lys
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 21

Ala Leu Lys Lys Leu Leu Lys Thr Leu Ser Lys Ala Arg Ala Ala Arg
1               5                   10                  15

Leu Lys Thr Leu Leu Lys Ala Leu Ser Lys
            20                  25
```

```
<210> SEQ ID NO 22
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (13)..(13)
<223> OTHER INFORMATION: Dpr
<220> FEATURE:
<221> NAME/KEY: MOD_RES
<222> LOCATION: (16)..(16)
<223> OTHER INFORMATION: Dpr

<400> SEQUENCE: 22

Ala Leu Lys Lys Leu Leu Lys Thr Leu Ser Lys Ala Xaa Ala Ala Xaa
1               5                   10                  15

Leu Lys Thr Leu Leu Lys Ala Leu Ser Lys
            20                  25

<210> SEQ ID NO 23
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)..(3)
<223> OTHER INFORMATION: Xaa is selected from Lys, Arg, Orn, Dpr and Dbu
<220> FEATURE:
<221> NAME/KEY: VARIANT
<222> LOCATION: (7)..(7)
<223> OTHER INFORMATION: Xaa is selected from Lys, Arg, Orn, Dpr and Dbu
<220> FEATURE:
<221> NAME/KEY: VARIANT
<222> LOCATION: (11)..(11)
<223> OTHER INFORMATION: Xaa is selected from Lys, Arg, Orn, Dpr and Dbu
<220> FEATURE:
<221> NAME/KEY: VARIANT
<222> LOCATION: (18)..(18)
<223> OTHER INFORMATION: Xaa is selected from Lys, Arg, Orn, Dpr and Dbu
<220> FEATURE:
<221> NAME/KEY: VARIANT
<222> LOCATION: (22)..(22)
<223> OTHER INFORMATION: Xaa is selected from Lys, Arg, Orn, Dpr and Dbu
<220> FEATURE:
<221> NAME/KEY: VARIANT
<222> LOCATION: (26)..(26)
<223> OTHER INFORMATION: Xaa is selected from Lys, Arg, Orn, Dpr and Dbu

<400> SEQUENCE: 23

Lys Leu Xaa Ser Leu Leu Xaa Thr Leu Ser Xaa Ala Lys Ala Ala Lys
1               5                   10                  15

Leu Xaa Thr Leu Leu Xaa Ala Leu Ser Xaa
            20                  25

<210> SEQ ID NO 24
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 24

Lys Leu Lys Ser Leu Leu Lys Thr Leu Ser Lys Ala Lys Ala Ala Lys
1               5                   10                  15

Leu Lys Thr Leu Leu Lys Ala Leu Ser Lys
            20                  25
```

```
<210> SEQ ID NO 25
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (18)..(18)
<223> OTHER INFORMATION: Orn
<220> FEATURE:
<221> NAME/KEY: MOD_RES
<222> LOCATION: (22)..(22)
<223> OTHER INFORMATION: Orn
<220> FEATURE:
<221> NAME/KEY: MOD_RES
<222> LOCATION: (26)..(26)
<223> OTHER INFORMATION: Orn

<400> SEQUENCE: 25

Lys Leu Xaa Ser Leu Leu Xaa Thr Leu Ser Xaa Ala Lys Ala Ala Lys
1               5                   10                  15

Leu Xaa Thr Leu Leu Xaa Ala Leu Ser Xaa
            20                  25

<210> SEQ ID NO 26
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (7)..(7)
<223> OTHER INFORMATION: Dbu
<220> FEATURE:
<221> NAME/KEY: MOD_RES
<222> LOCATION: (11)..(11)
<223> OTHER INFORMATION: Dbu
<220> FEATURE:
<221> NAME/KEY: MOD_RES
<222> LOCATION: (18)..(18)
<223> OTHER INFORMATION: Dbu
<220> FEATURE:
<221> NAME/KEY: MOD_RES
<222> LOCATION: (22)..(22)
<223> OTHER INFORMATION: Dbu
<220> FEATURE:
<221> NAME/KEY: MOD_RES
<222> LOCATION: (26)..(26)
<223> OTHER INFORMATION: Dbu

<400> SEQUENCE: 26

Lys Leu Xaa Ser Leu Leu Xaa Thr Leu Ser Xaa Ala Lys Ala Ala Lys
1               5                   10                  15

Leu Xaa Thr Leu Leu Xaa Ala Leu Ser Xaa
            20                  25
```

<210> SEQ ID NO 27
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 27

Lys Leu Arg Ser Leu Leu Arg Thr Leu Ser Arg Ala Lys Ala Ala Lys
1               5                   10                  15

Leu Arg Thr Leu Leu Arg Ala Leu Ser Arg
            20                  25

<210> SEQ ID NO 28
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES
<222> LOCATION: (7)..(7)
<223> OTHER INFORMATION: Dpr
<220> FEATURE:
<221> NAME/KEY: MOD_RES
<222> LOCATION: (11)..(11)
<223> OTHER INFORMATION: Dpr
<220> FEATURE:
<221> NAME/KEY: MOD_RES
<222> LOCATION: (18)..(18)
<223> OTHER INFORMATION: Dpr
<220> FEATURE:
<221> NAME/KEY: MOD_RES
<222> LOCATION: (22)..(22)
<223> OTHER INFORMATION: Dpr
<220> FEATURE:
<221> NAME/KEY: MOD_RES
<222> LOCATION: (26)..(26)
<223> OTHER INFORMATION: Dpr

<400> SEQUENCE: 28

Lys Leu Xaa Ser Leu Leu Xaa Thr Leu Ser Xaa Ala Lys Ala Ala Lys
1               5                   10                  15

Leu Xaa Thr Leu Leu Xaa Ala Leu Ser Xaa
            20                  25

<210> SEQ ID NO 29
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)..(3)
<223> OTHER INFORMATION: Xaa is selected from Lys, Dpr and Dbu
<220> FEATURE:
<221> NAME/KEY: VARIANT
<222> LOCATION: (7)..(7)
<223> OTHER INFORMATION: Xaa is selected from Lys, Dpr and Dbu
<220> FEATURE:
<221> NAME/KEY: VARIANT
<222> LOCATION: (14)..(15)
<223> OTHER INFORMATION: Xaa is selected from Lys, Dpr and Dbu
<220> FEATURE:
<221> NAME/KEY: VARIANT
<222> LOCATION: (22)..(22)

<223> OTHER INFORMATION: Xaa is selected from Lys, Dpr and Dbu
<220> FEATURE:
<221> NAME/KEY: VARIANT
<222> LOCATION: (26)..(26)
<223> OTHER INFORMATION: Xaa is selected from Lys, Dpr and Dbu

<400> SEQUENCE: 29

Lys Leu Xaa Ser Leu Leu Xaa Thr Leu Ser Ala Ala Lys Xaa Xaa Lys
1               5                   10                  15

Leu Ala Thr Leu Leu Xaa Ala Leu Ser Xaa
            20                  25

<210> SEQ ID NO 30
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 30

Lys Leu Lys Ser Leu Leu Lys Thr Leu Ser Ala Ala Lys Lys Lys Lys
1               5                   10                  15

Leu Ala Thr Leu Leu Lys Ala Leu Ser Lys
            20                  25

<210> SEQ ID NO 31
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (7)..(7)
<223> OTHER INFORMATION: Dbu
<220> FEATURE:
<221> NAME/KEY: MOD_RES
<222> LOCATION: (14)..(15)
<223> OTHER INFORMATION: Dbu
<220> FEATURE:
<221> NAME/KEY: MOD_RES
<222> LOCATION: (22)..(22)
<223> OTHER INFORMATION: Dbu
<220> FEATURE:
<221> NAME/KEY: MOD_RES
<222> LOCATION: (26)..(26)
<223> OTHER INFORMATION: Dbu

<400> SEQUENCE: 31

Lys Leu Xaa Ser Leu Leu Xaa Thr Leu Ser Ala Ala Lys Xaa Xaa Lys
1               5                   10                  15

Leu Ala Thr Leu Leu Xaa Ala Leu Ser Xaa
            20                  25

<210> SEQ ID NO 32
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES

```
<222> LOCATION: (7)..(7)
<223> OTHER INFORMATION: Dpr
<220> FEATURE:
<221> NAME/KEY: MOD_RES
<222> LOCATION: (14)..(15)
<223> OTHER INFORMATION: Dpr
<220> FEATURE:
<221> NAME/KEY: MOD_RES
<222> LOCATION: (22)..(22)
<223> OTHER INFORMATION: Dpr
<220> FEATURE:
<221> NAME/KEY: MOD_RES
<222> LOCATION: (26)..(26)
<223> OTHER INFORMATION: Dpr

<400> SEQUENCE: 32

Lys Leu Xaa Ser Leu Leu Xaa Thr Leu Ser Ala Ala Lys Xaa Xaa Lys
1               5                   10                  15

Leu Ala Thr Leu Leu Xaa Ala Leu Ser Xaa
            20                  25

<210> SEQ ID NO 33
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)..(3)
<223> OTHER INFORMATION: Xaa is selected from Lys and Dbu
<220> FEATURE:
<221> NAME/KEY: VARIANT
<222> LOCATION: (7)..(7)
<223> OTHER INFORMATION: Xaa is selected from Lys and Dbu
<220> FEATURE:
<221> NAME/KEY: VARIANT
<222> LOCATION: (11)..(11)
<223> OTHER INFORMATION: Xaa is selected from Lys and Dbu
<220> FEATURE:
<221> NAME/KEY: VARIANT
<222> LOCATION: (18)..(18)
<223> OTHER INFORMATION: Xaa is selected from Lys and Dbu
<220> FEATURE:
<221> NAME/KEY: VARIANT
<222> LOCATION: (22)..(22)
<223> OTHER INFORMATION: Xaa is selected from Lys and Dbu

<400> SEQUENCE: 33

Lys Leu Xaa Ser Leu Leu Xaa Thr Leu Ser Xaa Ala Lys Ala Ala Lys
1               5                   10                  15

Leu Xaa Thr Leu Leu Xaa Ala Leu Ser Ser
            20                  25

<210> SEQ ID NO 34
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 34

Lys Leu Lys Ser Leu Leu Lys Thr Leu Ser Lys Ala Lys Ala Ala Lys
1               5                   10                  15

Leu Lys Thr Leu Leu Lys Ala Leu Ser Ser
            20                  25

<210> SEQ ID NO 35
<211> LENGTH: 26
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (7)..(7)
<223> OTHER INFORMATION: Dbu
<220> FEATURE:
<221> NAME/KEY: MOD_RES
<222> LOCATION: (11)..(11)
<223> OTHER INFORMATION: Dbu
<220> FEATURE:
<221> NAME/KEY: MOD_RES
<222> LOCATION: (18)..(18)
<223> OTHER INFORMATION: Dbu
<220> FEATURE:
<221> NAME/KEY: MOD_RES
<222> LOCATION: (22)..(22)
<223> OTHER INFORMATION: Dbu

<400> SEQUENCE: 35

Lys Leu Xaa Ser Leu Leu Xaa Thr Leu Ser Xaa Ala Lys Ala Ala Lys
1               5                   10                  15

Leu Xaa Thr Leu Leu Xaa Ala Leu Ser Ser
            20                  25

<210> SEQ ID NO 36
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (3)..(3)
<223> OTHER INFORMATION: Xaa is selected from Lys and Dbu
<220> FEATURE:
<221> NAME/KEY: VARIANT
<222> LOCATION: (7)..(7)
<223> OTHER INFORMATION: Xaa is selected from Lys and Dbu
<220> FEATURE:
<221> NAME/KEY: VARIANT
<222> LOCATION: (14)..(15)
<223> OTHER INFORMATION: Xaa is selected from Lys and Dbu
<220> FEATURE:
<221> NAME/KEY: VARIANT
<222> LOCATION: (22)..(22)
<223> OTHER INFORMATION: Xaa is selected from Lys and Dbu

<400> SEQUENCE: 36

Lys Leu Xaa Ser Leu Leu Xaa Thr Leu Ser Ala Ala Lys Xaa Xaa Lys
1               5                   10                  15

Leu Ala Thr Leu Leu Xaa Ala Leu Ser Ser
            20                  25

<210> SEQ ID NO 37
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 37

Lys Leu Lys Ser Leu Leu Lys Thr Leu Ser Ala Ala Lys Lys Lys Lys
1               5                   10                  15

Leu Ala Thr Leu Leu Lys Ala Leu Ser Ser
            20                  25
```

```
<210> SEQ ID NO 38
<211> LENGTH: 25
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (7)..(7)
<223> OTHER INFORMATION: Dbu
<220> FEATURE:
<221> NAME/KEY: MOD_RES
<222> LOCATION: (14)..(14)
<223> OTHER INFORMATION: Dbu
<220> FEATURE:
<221> NAME/KEY: MOD_RES
<222> LOCATION: (21)..(21)
<223> OTHER INFORMATION: Dbu

<400> SEQUENCE: 38

Lys Leu Xaa Ser Leu Leu Xaa Thr Leu Ser Ala Ala Lys Xaa Lys Leu
1               5                   10                  15

Ala Thr Leu Leu Xaa Ala Leu Ser Ser
            20                  25
```